United States Patent
Purohit et al.

(12) 
(10) Patent No.: US 11,760,741 B2
(45) Date of Patent: Sep. 19, 2023

(54) PRO-DRUGS OF ELIGLUSTAT

(71) Applicant: KASHIV BIOSCIENCES, LLC, Bridgewater, NJ (US)

(72) Inventors: Parva Yogeshchandra Purohit, Ahmedabad (IN); Pathik Subhashchandra Brahmkshatriya, Ahmedabad (IN)

(73) Assignee: KASHIV BIOSCIENCES, LLC, Bridgewater, NJ (US)

( * ) Notice: Subject to any disclaimer, the term of this patent is extended or adjusted under 35 U.S.C. 154(b) by 0 days.

(21) Appl. No.: 17/052,062

(22) PCT Filed: May 2, 2019

(86) PCT No.: PCT/IB2019/053579
§ 371 (c)(1),
(2) Date: Oct. 30, 2020

(87) PCT Pub. No.: WO2019/211778
PCT Pub. Date: Nov. 7, 2019

(65) Prior Publication Data
US 2021/0300887 A1 Sep. 30, 2021

(30) Foreign Application Priority Data
May 2, 2018 (IN) .............................. 201821016626

(51) Int. Cl.
*C07D 319/18* (2006.01)
*C07D 405/12* (2006.01)

(52) U.S. Cl.
CPC ......... *C07D 319/18* (2013.01); *C07D 405/12* (2013.01)

(58) Field of Classification Search
CPC ........................... C07D 319/18; C07D 405/12
See application file for complete search history.

(56) References Cited

U.S. PATENT DOCUMENTS 8,389,517 B2 * 3/2013 Ibraghimov-Beskrovnaya ........... A61K 31/4178
514/321
2013/0137743 A1 5/2013 Liu et al.
2014/0336174 A1 11/2014 Ibraghimov-Beskrovnaya et al.

FOREIGN PATENT DOCUMENTS

WO 2017/068496 A1 4/2017

OTHER PUBLICATIONS

Registry No. 2193052-06-9, File REGISTRY on STN, Mar. 16, 2018.*
International Search Report dated Nov. 1, 2019, for corresponding International Patent Application No. PCT/IB2019/53579.
Written Opinion dated Nov. 1, 2019, for corresponding International Patent Application No. PCT/IB2019/53579.

* cited by examiner

*Primary Examiner* — Rebecca L Anderson
(74) *Attorney, Agent, or Firm* — Pergament & Cepeda LLP; Milagros A. Cepeda; Edward D. Pergament

(57) ABSTRACT

The present invention is directed to pro-drugs of Eliglustat (formula A) and process for the preparation thereof. The present invention is further directed to pharmaceutical composition thereof and method of treatment using the same.

(A)

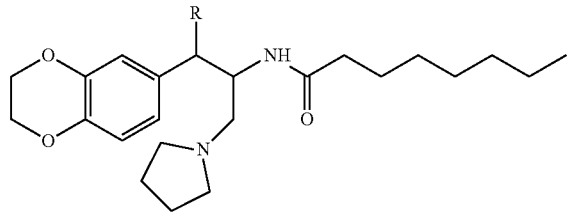

13 Claims, No Drawings

PRO-DRUGS OF ELIGLUSTAT

This application is a National Stage Application under 35 U.S.C. § 371 of PCT International Application No. PCT/IB2019/053579, filed May 2, 2019, which takes priority from Indian Provisional Application Number IN 201821016626, filed May 2, 2018.

FIELD OF INVENTION

The present invention is directed to pro-drugs of Eliglustat (formula A) and process for the preparation thereof. The present invention is further directed to pharmaceutical composition thereof and method of treatment using the same.

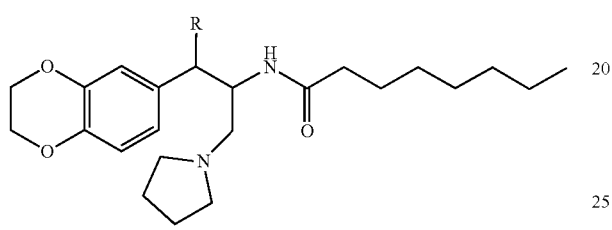

(A)

BACKGROUND OF THE INVENTION

Glucosylceramide synthase (GCS) has emerged in recent years as an attractive target for drug development both in relation to lysosomal storage disorders (in particular Gaucher disease) and type 2 diabetes. GCS catalyzes the transfer of glucose from UDP-glucose to ceramide to form glucosylceramide. Gaucher disease type 1 is a rare autosomal recessive lysosomal storage disorder in which the lipid glucosylceramide accumulates in Gaucher cells in organs including the spleen, liver and bone marrow due to insufficient production of the enzyme glucosylceramidase. This leads to clinical manifestations that include enlargement of the spleen and liver, skeletal complications, anemia and thrombocytopenia.

The current standard of care for Gaucher disease type 1 is enzyme replacement with imiglucerase (recombinant human glucosylceramidase), which can reverse or halt disease progression but is expensive and requires frequent intravenous infusions for the rest of the patient's life. Moreover, enzyme replacement therapy is associated with a potential risk of hypersensitivity reactions and, rarely, the development of antibodies to the enzyme that reduce its efficacy. Oral substrate reduction therapy with agents such as Miglustat and Eliglustat represents an alternative treatment strategy for Gaucher disease type 1.

Eliglustat is a small-molecule oral glucosylceramide analogue developed by Genzyme Corporation for the long-term treatment of Gaucher disease type 1. It is approved for the treatment of Gaucher disease type 1 in treatment-naïve and treatment-experienced adult patients. It is the first oral treatment to be approved for first-line use in patients with Gaucher disease type 1.

Eliglustat is metabolized mainly by CYP2D6 and to a lesser extent by CYP3A4. The pharmacokinetics of Eliglustat are dependent on CYP2D6 phenotype. Eliglustat is indicated for use in patients who are cytochrome P450 (CYP) 2D6 extensive, intermediate, or poor metabolizers, as identified by a genetic test approved by the US Food and Drug Administration. However, it is contraindicated in patients who are ultra-rapid CYP2D6 metabolizers and may not achieve therapeutic concentrations of Eliglustat, and those whose CYP2D6 metabolic rate is undetermined and for whom a specific dosage cannot be recommended.

The high first pass metabolism leads to very low bioavailability of Eliglustat. Therefore, there is a need to explore pro-drugs of Eliglustat having desired pharmacokinetic profile.

The present inventors have surprisingly found novel pro-drugs of Eliglustat (formula A) which meets unmet medical needs.

SUMMARY OF THE INVENTION

In one aspect the present invention relates to pro-drugs of Eliglustat (formula A) and the geometric isomers, enantiomers, diastereomers, racemates, pharmaceutically acceptable salts and solvates thereof

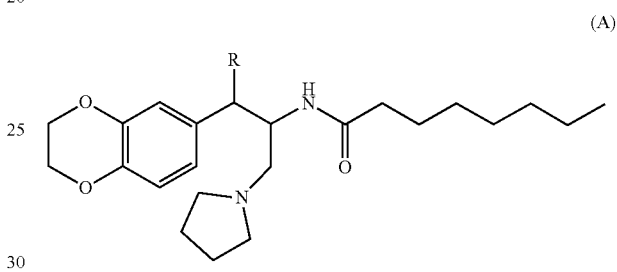

(A)

wherein, R is selected from group comprising of:
a)

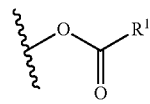

wherein, $R^1$ is selected from group comprising of optionally substituted aryl, optionally substituted heteroaryl, optionally substituted cycloalkyl, cycloheteroalkyl, alkyl, amine, alkoxy, carboxylic acid, alkyl substituted with cycloheteroalkyl; alkyl substituted amine, alkyl substituted carboxylic acid, alkene substituted carboxylic acid.
b)

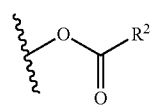

wherein, $R^2$ is

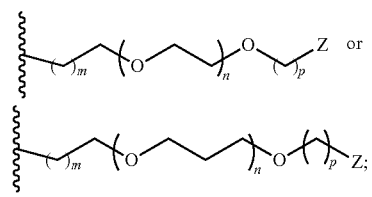

wherein m and p are independently selected from 0 to 3, n refers to degree of polymerization and Z is alkyl or amine.

c) R³ wherein, R³ is selected from group comprising of boron species.

d)

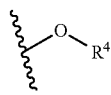

wherein, R⁴ is selected from group comprising of alkyl, alkyl substituted with cycloheteroalkyl, optionally substituted phosphoryl, alkyl substituted phosphoryl, sulfuryl, sulfonamide, with a proviso that when R⁴ is alkyl it excludes methyl.

e)

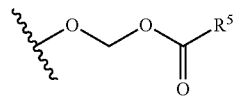

wherein, R⁵ is selected from group comprising of optionally substituted aryl, optionally substituted heteroaryl, optionally substituted cycloalkyl, cycloheteroalkyl, alkyl, amine, alkoxy, carboxylic acid, alkyl substituted with cycloheteroalkyl; alkyl substituted amine.

In one aspect the present invention relates to pro-drugs of Eliglustat (formula I) and the geometric isomers, enantiomers, diastereomers, racemates, pharmaceutically acceptable salts and solvates thereof

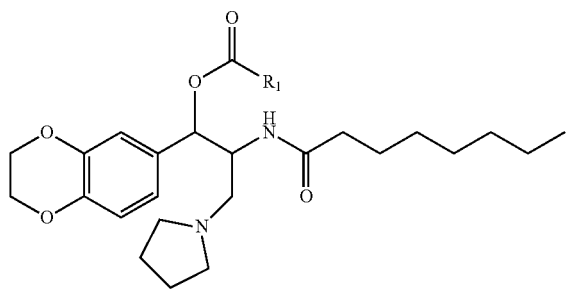

(I)

wherein, R¹ has same meaning as defined above.

In one aspect the present invention relates to pro-drugs of Eliglustat (formula II) and the geometric isomers, enantiomers, diastereomers, racemates, pharmaceutically acceptable salts and solvates thereof

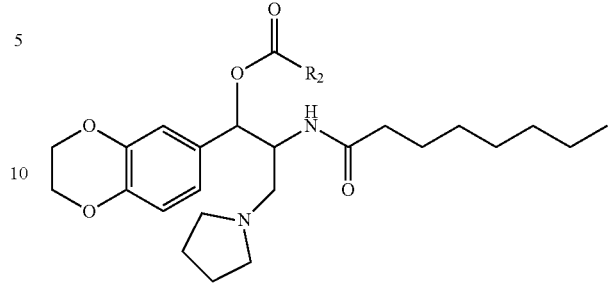

(II)

wherein, R² has same meaning as defined above.

In one aspect the present invention relates to pro-drugs of Eliglustat (formula III) and the geometric isomers, enantiomers, diastereomers, racemates, pharmaceutically acceptable salts and solvates thereof

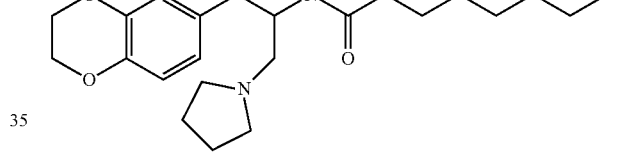

(III)

wherein, R³ has same meaning as defined above.

In one aspect the present invention relates to pro-drugs of Eliglustat (formula IV) and the geometric isomers, enantiomers, diastereomers, racemates, pharmaceutically acceptable salts and solvates thereof

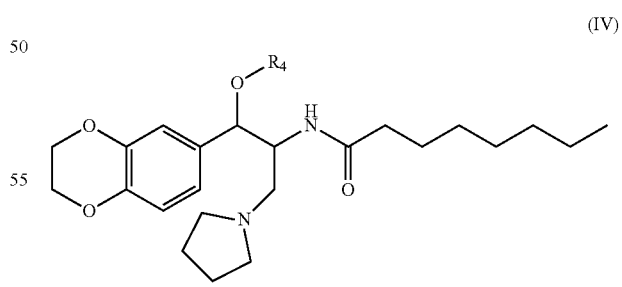

(IV)

wherein, R⁴ has same meaning as defined above.

In one aspect the present invention relates to pro-drugs of Eliglustat (formula IX) and the geometric isomers, enantiomers, diastereomers, racemates, pharmaceutically acceptable salts and solvates thereof

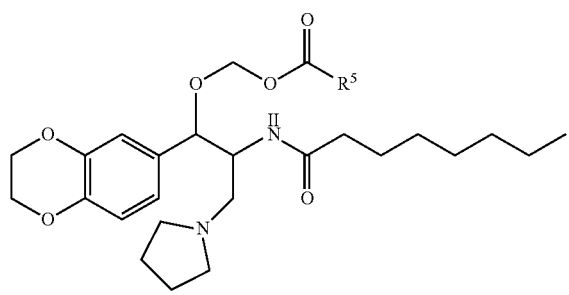

(IX)

wherein, R⁵ has same meaning as defined above.

In another aspect the present invention relates to process for the preparation of pro-drugs of Eliglustat (formula I) comprising reacting Eliglustat (V) with compound of formula (VI) or active esters (formula VI') thereof

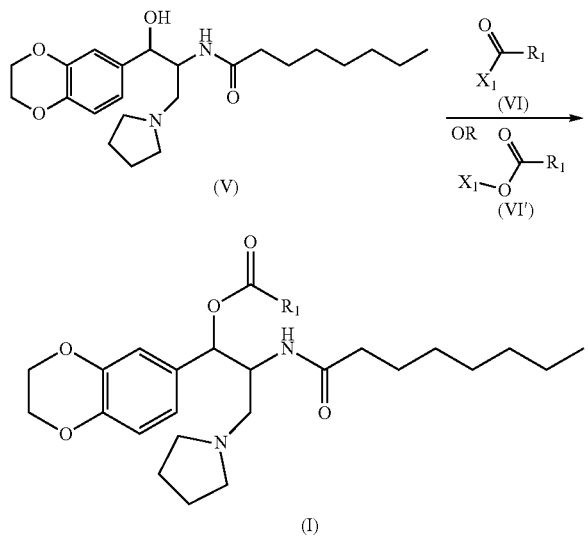

wherein, $R^1$ has same meaning as defined above and $X^1$ is selected from group comprising of halogen, hydroxyl, alkyl, cycloalkyl, cycloheteroalkyl, amine, azide, tosyl, mesyl, thiol, hydrazide, sulphonic acid, optionally substituted aryl, nitrile or $R^1$ and $X^1$ are combined together to form cycloalkyl or cycloheteroalkyl.

In another aspect the present invention relates to process for the preparation of pro-drugs of Eliglustat (formula II) comprising reacting Eliglustat (V) with compound of formula (VII) or active esters (formula VII') thereof

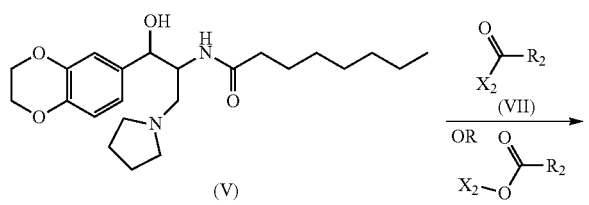

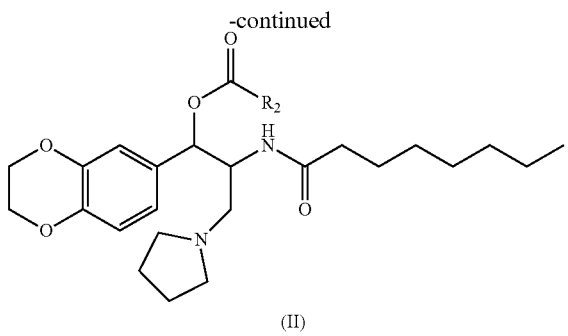

wherein, $R^2$ has same meaning as defined above and $X^2$ is selected from group comprising of halogen, hydroxyl, alkyl, cycloalkyl, cycloheteroalkyl, amine, azide, tosyl, mesyl, thiol, hydrazide, sulphonic acid, optionally substituted aryl, nitrile.

In another aspect the present invention relates to process for the preparation of pro-drugs of Eliglustat (formula III) comprising reacting Eliglustat (V) with a suitable leaving group (LG) to obtain compound of formula (III') and converting compound of formula (III') to compound of formula (III) by reacting compound of formula (III') with suitable boronating reagent in presence of a palladium catalyst.

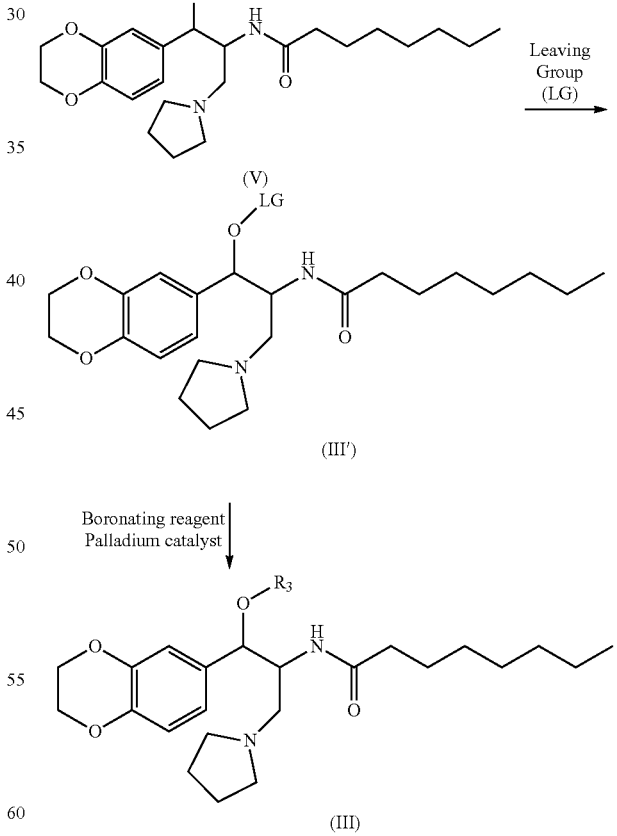

wherein, $R^3$ has same meaning as defined above.

In another aspect the present invention relates to process for the preparation of pro-drugs of Eliglustat (formula IV) comprising reacting Eliglustat (V) with compound of formula (VIII).

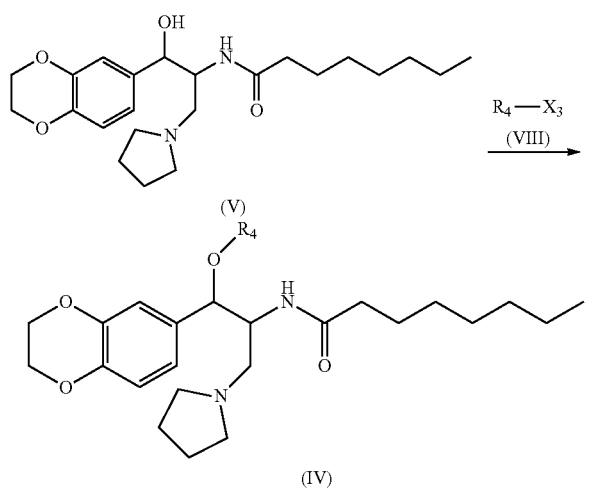

wherein, $R^4$ has same meaning as defined above and $X^3$ is selected from group comprising of halogen, hydroxyl.

In another aspect the present invention relates to process for the preparation of pro-drugs of Eliglustat (formula IX) comprising reacting Eliglustat (V) with compound of formula (X).

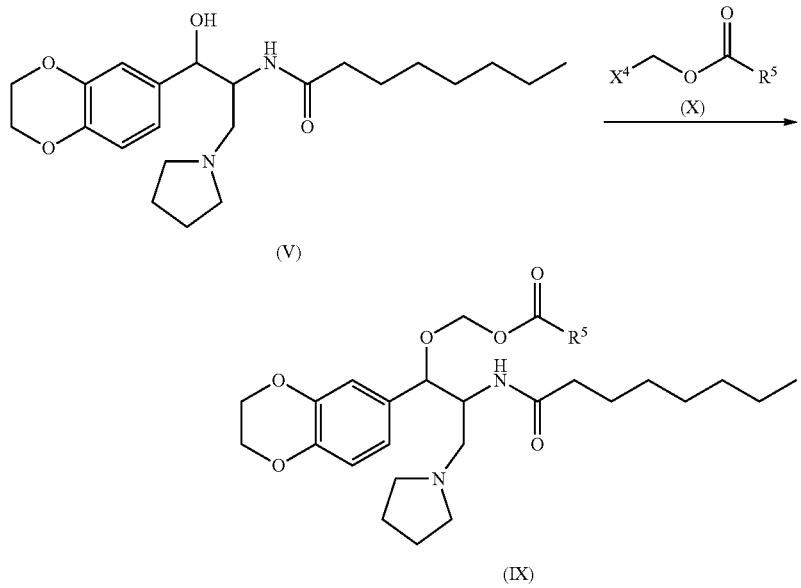

wherein, $R^5$ has same meaning as defined above and $X^4$ is selected from group comprising of halogen.

In one aspect the present invention relates to pharmaceutical composition comprising pro-drugs of Eliglustat (formula A) or pharmaceutically acceptable salts or solvates thereof and pharmaceutically acceptable excipients.

In one aspect the present invention relates to use of pro-drugs of Eliglustat (formula A) and pharmaceutically acceptable salts or solvates thereof in treatment of Gaucher disease, Fabry disease, Tay-Sachs disease, Sandhoff disease, GM1 gangliosidosis disease, glomerular disease.

DETAILED DESCRIPTION OF THE INVENTION

It is to be understood that the invention is not limited in its application to the details set forth in the following description or exemplified by the examples. The invention is capable of other embodiments or of being practiced or carried out in various ways. Also, it is to be understood that the phraseology and terminology employed herein is for the purpose of description and should not be regarded as limiting.

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to"). Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

It is to be understood that that the structures of some of the compounds of this invention include asymmetric carbon atoms. It is to be understood accordingly that the isomers arising from such asymmetry (e.g., all enantiomers and diastereomers, racemates) are included within the scope of this invention. Such isomers can be obtained in substantially pure form by classical separation techniques such as high-performance liquid chromatography (HPLC), upercritical fluid chromatography (SEC), capillary electrochromatography (CEC), chiral chromatography or other alternative techniques known to person having ordinary skill in the art and by stereochemically controlled synthesis. Furthermore, the structures and other compounds and moieties discussed in this application also include all tautomers and geometric isomers thereof.

The term "about" as used herein, when referring to a measurable value is meant to encompass variations of ±10%, preferably ±5%, more preferably ±1%, and still more preferably ±0.1% from the specified value.

The term "salt" or "pharmaceutically acceptable salt" as used herein refers to pharmaceutically acceptable acid addition salts formed with organic or inorganic acids. Exemplary of such organic salts are those but not limited to maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-toulenesulfonic acid, p-aminobenzoic, glutamic, benzenesulfonic, theophylline acetic acids and the like and their enantiomers, diastereomers and racemates. Exemplary of such inorganic salts are those but not limited to hydrochloric, hydrobromic, sulfuric, sulfamic, phosphoric, nitric acids and the like. Preferred acid addition salt is hydrochloride salt or tartrate salt.

The term "aryl" as used herein refers to groups, including 5- and 6-membered single-ring aromatic groups that can include from zero to four heteroatoms, for example, phenyl, benzyl, pyrrole, furan, thiophene, thiazole, isothiaozole, imidazole, triazole, tetrazole, pyrazole, oxazole, isoxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, me thylenedioxyphenyl, quinoline, isoquinoline, anthryl, phenanthryl, napthridine, indole, benzofuran, purine, benzofuran, deazapurine, or indolizine. Those aryl groups having heteroatoms in the ring structure can also be referred to as "aryl heterocycles", "heterocycles," "heteroaryls" or "heteroaromatics."

The term "optionally substituted aryl" as used herein refers to aryl compounds having zero, one, two, three or four substituents, and a substituted aryl includes aryl compounds having one, two, three or four substituents, wherein the substituents include groups such as, for example, alkyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be substituted with a fused or bridged alicyclic or heterocyclic rings which are not aromatic so as to form a polycycle (e.g., tetralin).

The term "optionally substituted heteroaryl" as used herein refers to a heteroaryl compounds having zero, one, two, three or four substituents, and a substituted heteroaryl includes heteroaryl compounds having one, two, three or four substituents, wherein the substituents include groups such as, for example, alkyl, halo, amino substituents or the like.

The term "optionally substituted cycloalkyl" as used herein refers to a cycloalkyl compounds having zero, one, two, three or four substituents, and a substituted cycloalkyl includes cycloalkyl compounds having one, two, three or four substituents, wherein the substituents include groups such as, for example, alkyl, halo, amino substituents or the like. The cycloalkyl groups can also be substituted with a fused or bridged alicyclic or heterocyclic rings to form saturated or unsaturated multicyclic ring system, e.g., bicyclic, tricyclic.

The term "cycloheteroalkyl" as used herein refers to substituted or unsubstituted a five to seven-membered saturated or unsaturated cycloalkyl ring system containing one or more heteroatoms, which may be the same or different, selected from N, O, or S. The cycloheteroalkyl groups can also be substituted with a fused or bridged alicyclic or heterocyclic rings to form saturated or unsaturated multicyclic ring system, e.g., bicyclic, tricyclic.

The term "alkyl," as used herein refers to a straight or branched chain, or cyclic hydrocarbon radical, or combination thereof, which may be fully saturated, mono- or poly-unsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkene" as used herein refers to branched and straight-chain groups of the formula $C_nH_{2n-1}$, specifically includes vinyl and allyl.

The term "amine" or "amino" should be understood as being broadly applied to both a molecule, or a moiety or functional group, as generally understood in the art, and can be primary, secondary, or tertiary. The term "amine" or "amino" includes compounds where a nitrogen atom is covalently bonded to at least one carbon, hydrogen or heteroatom. The terms include, for example, but are not limited to, "alkyl amino," "arylamino," "diarylamino," "alkylarylamino," "alkylaminoaryl," "arylaminoalkyl," "alkaminoalkyl," "amide," "amido," and "aminocarbonyl." The term "alkyl amino" comprises groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "carboxylic acid" as used herein refers to saturated or unsaturated aliphatic, cyclic, alicyclic and heterocyclic, mono-, di-, tri-, tetra- and other polycarboxylic acids. The carboxylic acids of the present invention are not particularly limited and any of those which can be converted into the corresponding anhydrides by the exchange reaction with the acid anhydride may be used.

The term "optionally substituted phosphoryl" as used herein refers to unsubstituted phosphoryl group, a ($C_{1-6}$ alkoxy)phosphoryl group such as, a di-($C_{1-6}$alkoxy)phosphoryl group such as diethoxyphosphoryl, a lower ($C_{1-6}$) alkyl group substituted with an optionally esterified phosphono group such as a phosphono-$C_{1-6}$ alkyl group, a $C_{1-6}$ alkoxyphosphoryl-$C_{1-6}$ alkyl group, a di-($C_{1-6}$ alkoxy) phosphoryl-$C_{1-6}$ alkyl group such as diethoxyphosphorylmethyl, and the like.

The term "sulfonamide" as used herein refers to optionally substituted S-sulfonamide groups, i.e., —$SO_2N$— and optionally substituted N-sulfonamide groups, i.e., —$NSO_2$—.

The tem "alkoxy" refers to the group —O-alkyl.

The term "halogen" as used herein means fluorine, chlorine, bromine and iodine.

The term "sulfuryl" refers to the group —$S(O)_2$—.

The term "azide" refers to the group —$N_3$.

The term "tosyl" is an abbreviation for p-toluene sulfonyl.

The term "mesyl" means the group $CH_3$—$SO_2$—

The term "thiol" means the group —SH.

The term "hydrazide" means the group —NH—$NH_2$.

The term "sulphonic acid" means the group —$S(O)_2$—OH.

The term "nitrile" means the group —CN.

The tem "phosphoryl" refers to the group —$PO_3^-$.

The term "degree of polymerization" refers to a number of repeating polyethylene glycol (PEG) or polypropylene glycol moieties in a single Eliglustat molecule. The pro-drugs of Eliglustat (formula II) of present invention have degree of polymerization comprising of less than 10 repeating polyethylene glycol (PEG) or polypropylene glycol moieties, about 50 repeating polyethylene glycol (PEG) or polypropylene glycol moieties, about 100 repeating polyethylene glycol (PEG) or polypropylene glycol moieties, about 150 repeating polyethylene glycol (PEG) or polypropylene glycol moieties and about 200 repeating polyethylene glycol (PEG) or polypropylene glycol moieties. In one preferred embodiment, pro-drugs of Eliglustat (formula II) of present invention have degree of polymerization about 150 repeating polyethylene glycol (PEG) or polypropylene glycol moieties.

The pro-drugs of Eliglustat (formula II) of present invention comprises polyethylene glycol (PEG) or polypropylene glycol moieties having molecular weight of less than 2000 Da, about 2000 Da, about 5000 Da, about 10,000 Da, about 20,000 Da and about 30,000 Da. In one preferred embodiment, the pro-drugs of Eliglustat (formula II) of present invention comprises polyethylene glycol (PEG) or polypropylene glycol moieties having molecular weight of about 5000 Da.

The term 'boron species' refers to compounds containing boron, for example, substituted or unsubstituted borane, substituted or unsubstituted perhaloborane, substituted or unsubstituted boronic acid, substituted or unsubstituted borinic acid, substituted or unsubstituted borinate ester, substituted or unsubstituted boronate ester, for example substituted or unsubstituted dioxaborolane and the like. Substitutions can be selected from group comprising of alkyl, amine, moiety derived from a sugar and the like, wherein when substitution is sugar, the atom attached to boron in each case is an oxygen atom. As used herein, the term "moiety derived from a sugar" refers to a moiety formed by removing the hydrogen atoms from two hydroxyl groups of any sugar moiety. The moiety derived from a sugar may be attached to boron by any two of the hydroxyl groups of the sugar. For example, in various embodiments, the boronate ester forms a 5-, 6-, 7-, 8-, or 9-membered ring. In some preferred embodiments, the boronate ester forms a 5- or 6-membered ring. The sugar is preferably a monosaccharide or disaccharide. Non-limiting examples of suitable sugars include but not limited to glucose, sucrose, fructose, trehalose, xylitol, mannitol, and sorbitol and the like.

The term "pharmaceutically acceptable excipient" as used herein includes vehicles, adjuvants, or diluents or other auxiliary substances, such as those conventional in the art, which are readily available to the public. For example, pharmaceutically acceptable excipients include pH adjusting and buffering agents, tonicity adjusting agents, stabilizers, wetting agents and the like.

The term "leaving group" or "LG" as used herein refers to a group which is part of and attached to a substrate molecule; in a reaction where the substrate molecule undergoes a displacement reaction, the group is then displaced. Examples of leaving groups include, but are not limited to: halogen (F, Cl, Br, and I), tosylate, mesylate, triflate, acetate, camphorsulfonate, aryloxide, and aryloxide substituted with at least one electron withdrawing group like, p-nitrophenoxide, 2-chlorophenoxide, 4-chlorophenoxide, 2,4-dinitrophenoxide, pentafluorophenoxide and like.

The term "boronating reagent" as used herein includes but not limited to 9-borabicyclo[3.3.1]nonane (9-BBN), disiamylborane, thexylborane; catecholborane, pinacolborane, bis(pinacolato)diboron or pinacolatoborane; borane-tetrahydrofuran, borane dimethylsulfide (BMS), diborane, diisopinocampheylborane, HB(Cyclohexyl)$_2$, and the like.

The term "palladium catalyst" as used herein includes but not limited to palladium acetate Pd(OAc)$_2$, tetrakis(triphenylphosphine)palladium(0), Pd(PPh$_3$)$_4$, bis(triphenylphosphine)palladium(II) dichloride, PdCl$_2$(PPh$_3$)$_2$, transdichlorobis (di-tert-butylphosphine)palladium(II) PdCl$_2$[P(tBu)$_2$Ph]$_2$, [1,1-Bis-(diphenyl-phosphino)ferrocene]dichloropalladium(II) Pd(dppf)Cl$_2$, Bis[di-(tert-butyl)(4-trifluoromethylphenyl)phosphine]palladium(II) chloride, Bis(di-tert-butyl(4-dimethylamino-phenyl)phosphine)dichloropalladium(II) Pd(amphos)Cl$_2$ and the like.

The term "coupling agent" as used herein includes but not limited to O-benzotriazole-N,N,N',N'-tetramethyl-uronium-hexafluoro-phosphate (HBTU), 2-(7-Aza-1H-benzotriazole-1-yl)-1,1,3,3-tetramethyluroniumhexafluorophosphate (HATU), acid halide, 1-hydroxybenzotriazole (HOBt), 1-Hydroxy-7-aza-1H-benzotriazole (HOAt), diisopropylcarbodiimide (DIC), dicyclohexylcarbodiimide (DCC), N-(3-Dimethylaminopropyl)-N-ethylcarbodiimide hydrochloride (EDC), 2-(6-Chloro-1H-benzotriazol-1-yl)-N,N,N',N'-tetramethylaminium hexafluoro-phosphate (HCTU), 1-[1-(Cyano-2-ethoxy-2-oxoethylideneaminooxy) dimethyl-aminomorpholino]-uroniumhexa-fluorophosphate (COMU) and the like.

The term "base" as used herein includes but not limited to inorganic base such as ammonia or hydroxide, carbonate, or bicarbonate of a metal cation or ammonia or organic bases such as organic primary, secondary, or tertiary amine. The base may be chosen as appropriate depending on various reaction conditions known to those skilled in the art.

The term "conventional techniques" as used herein includes but not limited to distillation, distillation under reduced pressure or vacuum, evaporation, solvent, anti-solvent, spray drying, lyophilization or freeze drying.

The term "organic solvent" or "solvent" or "anti-solvent" as used herein includes but not limited to polar protic and aprotic solvents as well as non-polar solvents selected from water, hydrocarbons, ketones, alcohols, ethers, esters, halogenated solvents, dimethyl sulfoxide (DMSO) and dimethylformamide (DMF), pyridine, phenol, DMA, carbon disulphide, acetic acid, acetonitrile and mixtures thereof. Hydrocarbons include but not limited to such as benzene, toluene, xylene, pentane, hexane, heptane, cyclo hexane and tetraline. Ketones include but not limited to such as acetone, methyl ethyl ketone, cyclohexanone and methyl isobutyl ketone. Alcohols include but not limited to such as methanol, ethanol, propanol, butanol, octanol, ethanediol, 1,2-propane diol and S (+)-1,2-propane diol. Ethers include but not limited to such as diethyl ether, di isopropyl ether, di butyl ether, methyl tert-butyl ether, 1,4-dioxane, tetrahydrofuran and cyclo pentyl methyl ether. Halogenated solvents include but not limited to such as chloroform, carbon tetrachloride, methylene chloride and 1,2-dichloro ethane. Esters include but not limited to such as methyl acetate, ethyl acetate, isopropyl acetate, n-butyl acetate and n-propyl acetate.

The term "solvate" as used herein refers to a compound which contains a stoichiometric or non-stoichiometric amount of solvent bound by non-covalent intermolecular forces. When the solvent is water, hydrate is formed. The term "hydrate" as used herein refers to a compound which is formed by the union of water with the parent compound.

The starting material, Eliglustat, used for the preparation of pro-drugs of Eliglustat (formula I or formula III or formula IV or formula IX) and pro-drugs of Eliglustat (formula II), was prepared according to process disclosed in prior-art and known to person having ordinary skills in the art.

In one embodiment, the present invention is directed to pro-drugs of Eliglustat (formula A) and the geometric isomers, enantiomers, diastereomers, racemates, pharmaceutically acceptable salts and solvates thereof

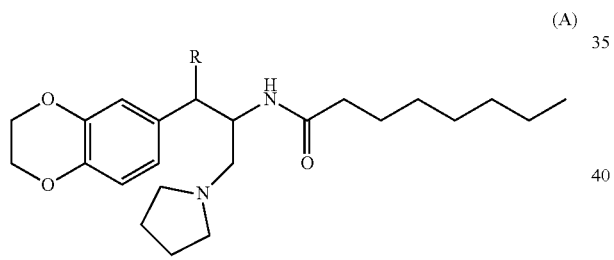

(A)

wherein, R is selected from group comprising of:
a)

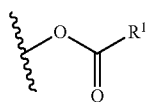

wherein, $R^1$ is selected from group comprising of optionally substituted aryl, optionally substituted heteroaryl, optionally substituted cycloalkyl, cycloheteroalkyl, alkyl, amine, alkoxy, carboxylic acid, alkyl substituted with cycloheteroalkyl; alkyl substituted amine, alkyl substituted carboxylic acid, alkene substituted carboxylic acid.

b)

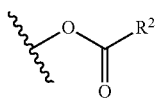

wherein, $R^2$ is

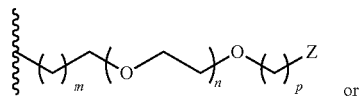

or

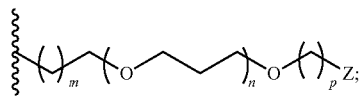

wherein m and p are independently selected from 0 to 3, n refers to degree of polymerization and Z is alkyl or amine.

c) $R^3$ wherein, $R^3$ is selected from group comprising of boron species.

d)

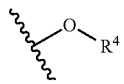

wherein, $R^4$ is selected from group comprising of alkyl, alkyl substituted with cycloheteroalkyl, optionally substituted phosphoryl, alkyl substituted phosphoryl, sulfuryl, sulfonamide, with a proviso that when $R^4$ is alkyl it excludes methyl.

e)

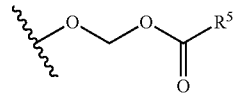

wherein, $R^5$ is selected from group comprising of optionally substituted aryl, optionally substituted heteroaryl, optionally substituted cycloalkyl, cycloheteroalkyl, alkyl, amine, alkoxy, carboxylic acid, alkyl substituted with cycloheteroalkyl; alkyl substituted amine.

In one embodiment, the present invention is directed to pro-drugs of Eliglustat (formula I) and the geometric isomers, enantiomers, diastereomers, racemates, pharmaceutically acceptable salts and solvates thereof

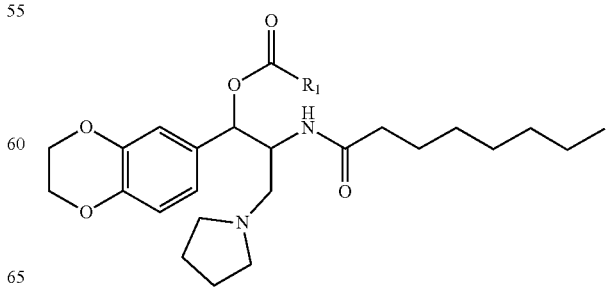

(I)

wherein, $R^1$ has same meaning as defined above.

In one embodiment, the present invention is directed to pro-drugs of Eliglustat (formula II) and the geometric isomers, enantiomers, diastereomers, racemates, pharmaceutically acceptable salts and solvates thereof

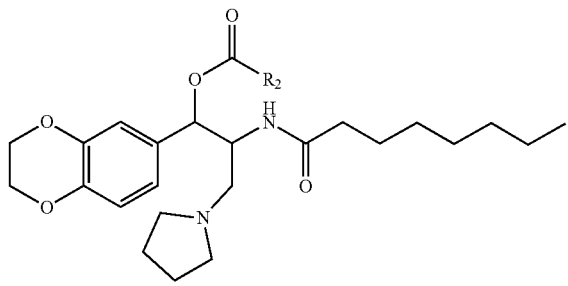

(II)

wherein, $R^2$ has same meaning as defined above.

In one embodiment, the present invention is directed to pro-drugs of Eliglustat (formula III) and the geometric isomers, enantiomers, diastereomers, racemates, pharmaceutically acceptable salts and solvates thereof

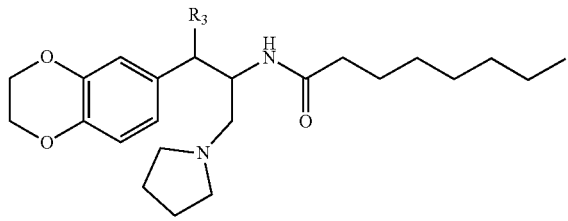

(III)

wherein, $R^3$ has same meaning as defined above.

In one embodiment, the present invention is directed to pro-drugs of Eliglustat (formula IV) and the geometric isomers, enantiomers, diastereomers, racemates, pharmaceutically acceptable salts and solvates thereof

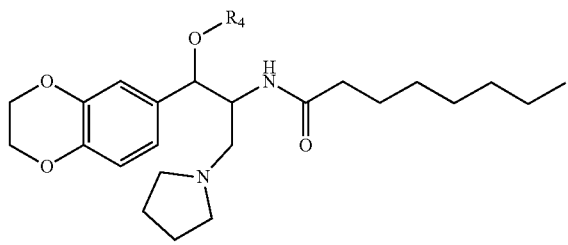

(IV)

wherein, $R^4$ has same meaning as defined above.

In one embodiment, the present invention is directed to pro-drugs of Eliglustat (formula IX) and the geometric isomers, enantiomers, diastereomers, racemates, pharmaceutically acceptable salts and solvates thereof

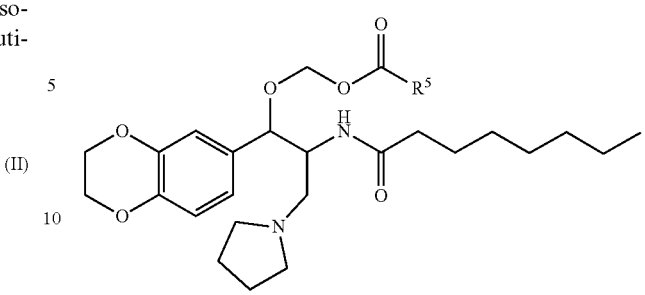

(IX)

wherein, $R^5$ has same meaning as defined above.

In one embodiment, the present invention is directed to process for the preparation of pro-drugs of Eliglustat (formula I) comprising reacting Eliglustat (V) with compound of formula (VI) or active esters (formula VI') thereof

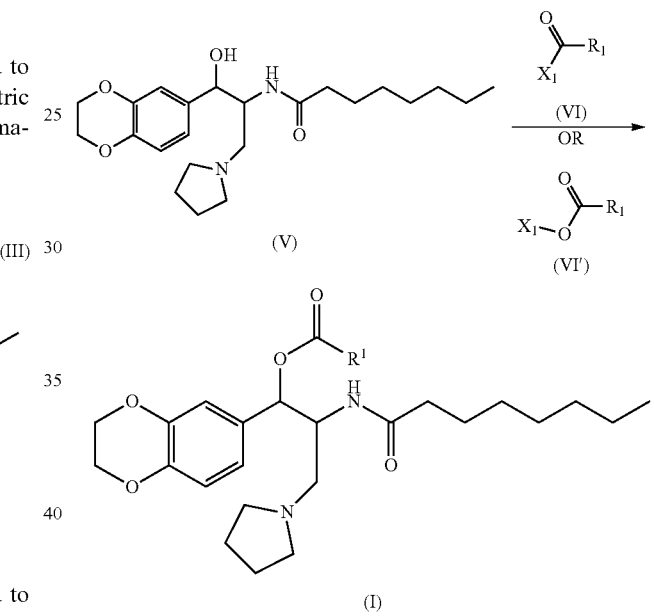

(V)

(VI)

OR (VI')

(I)

wherein, $R^1$ has same meaning as defined above and $X^1$ is selected from group comprising of halogen, hydroxyl, alkyl, cycloalkyl, cycloheteroalkyl, amine, azide, tosyl, mesyl, thiol, hydrazide, sulphonic acid, optionally substituted aryl, nitrile or R1 and X1 are combined together to form cycloalkyl or cycloheteroalkyl.

In another embodiment, the process for the preparation of pro-drugs of Eliglustat (formula I) as referred herein can be carried out in presence of a base, selected from group comprising of sodium hydride or triethylamine (TEA) or pyridine or 4-Dimethylaminopyridine (DMAP) or combination thereof.

In another embodiment, the process for the preparation of pro-drugs of Eliglustat (formula I) as referred herein can be carried out in presence of a coupling agent, selected from group comprising of EDC, HOBt, HBTU.

In one embodiment, the present invention is directed to pro-drugs of Eliglustat (formula II) comprising reacting Eliglustat (V) with compound of formula (VII) or active esters (formula VII') thereof

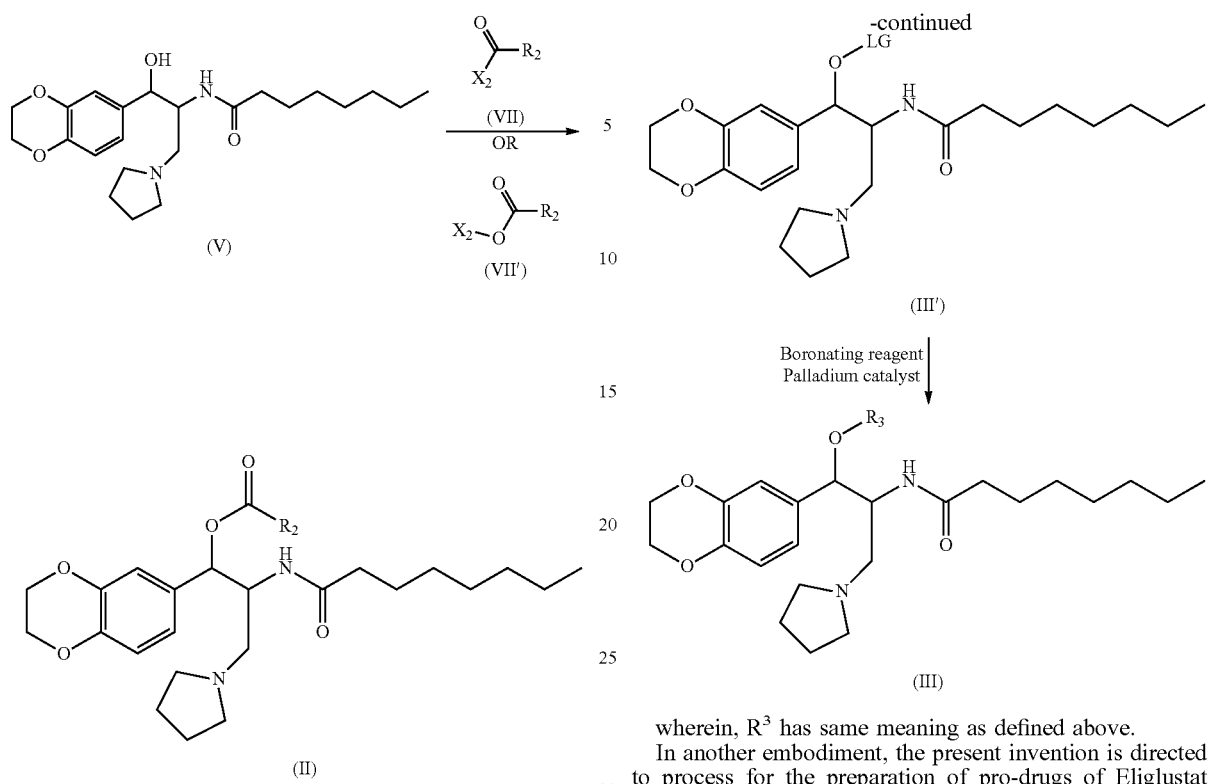

wherein, $R^2$ has same meaning as defined above and $X^2$ is selected from group comprising of halogen, hydroxyl, alkyl, cycloalkyl, cycloheteroalkyl, amine, azide, tosyl, mesyl, thiol, hydrazide, sulphonic acid, optionally substituted aryl, nitrile.

In another embodiment, the process for the preparation of pro-drugs of Eliglustat (formula II) as referred herein can be carried out in presence of a base, selected from group comprising of sodium hydride or triethylamine (TEA) or pyridine or 4-Dimethylaminopyridine (DMAP) or combination thereof.

In another embodiment, the process for the preparation of pro-drugs of Eliglustat (formula II) as referred herein can be carried out in presence of a coupling agent, selected from group comprising of EDC, HOBt, HBTU.

In one embodiment, the present invention is directed to process for the preparation of pro-drugs of Eliglustat (formula III) comprising reacting Eliglustat (V) with a suitable leaving group (LG) to obtain compound of formula (III') and converting compound of formula (III') to compound of formula (III) by reacting compound of formula (III') with suitable boronating reagent in presence of a palladium catalyst

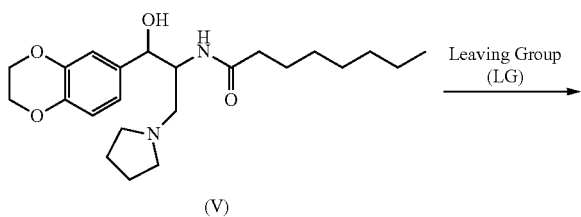

wherein, $R^3$ has same meaning as defined above.

In another embodiment, the present invention is directed to process for the preparation of pro-drugs of Eliglustat (formula IV) comprising reacting Eliglustat (V) with compound of formula (VIII)

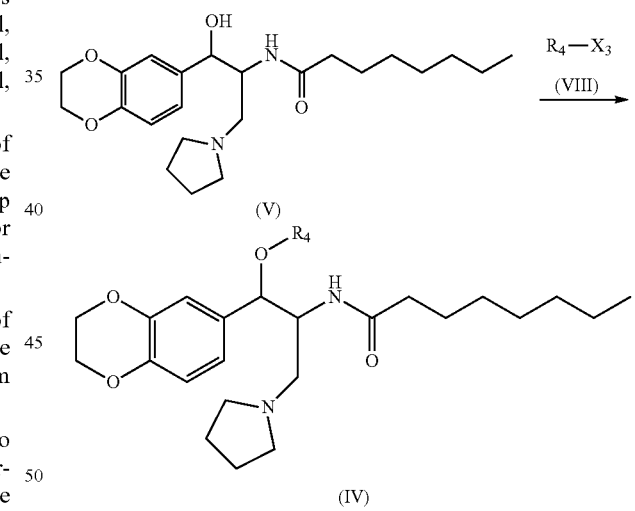

wherein, $R^4$ has same meaning as defined above and $X^3$ is selected from group comprising of halogen, hydroxyl.

In another embodiment, the process for the preparation of pro-drugs of Eliglustat (formula IV) as referred herein can be carried out in presence of a base, selected from group comprising of potassium carbonate, sodium hydride or triethylamine (TEA) or pyridine or 4-Dimethylaminopyridine (DMAP) or combination thereof.

In another embodiment, the process for the preparation of pro-drugs of Eliglustat (formula IV) as referred herein can be carried out in presence of a coupling agent, selected from group comprising of EDC, HOBt, HBTU.

In one embodiment, the present invention is directed to process for the preparation of pro-drugs of Eliglustat (formula IX) comprising reacting Eliglustat (V) with compound of formula (X).

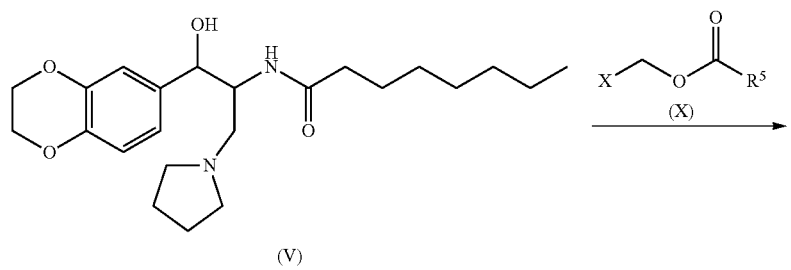

(V)

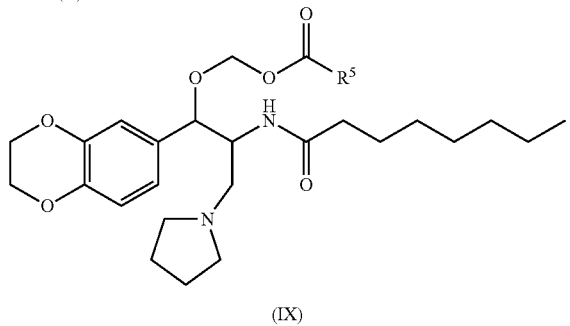

(IX)

wherein, $R^5$ has same meaning as defined above and $X^4$ is selected from group comprising of halogen.

In another embodiment, the process for the preparation of pro-drugs of Eliglustat (formula IX) as referred herein can be carried out in presence of a base, selected from group comprising of potassium carbonate, sodium hydride or triethylamine (TEA) or pyridine or 4-Dimethylaminopyridine (DMAP) or combination thereof.

In another embodiment, the present invention comprises isolation of pro-drugs of Eliglustat (formula I, III, IV, IX) or pro-drugs of Eliglustat (formula II) or pharmaceutically acceptable salt as referred herein by conventional techniques.

In one embodiment, the present invention is directed to pro-drugs of Eliglustat (formula I) and the geometric isomers, enantiomers, diastereomers, racemates, pharmaceutically acceptable salts and solvates thereof (I)

wherein, $R^1$ is selected from group comprising of:

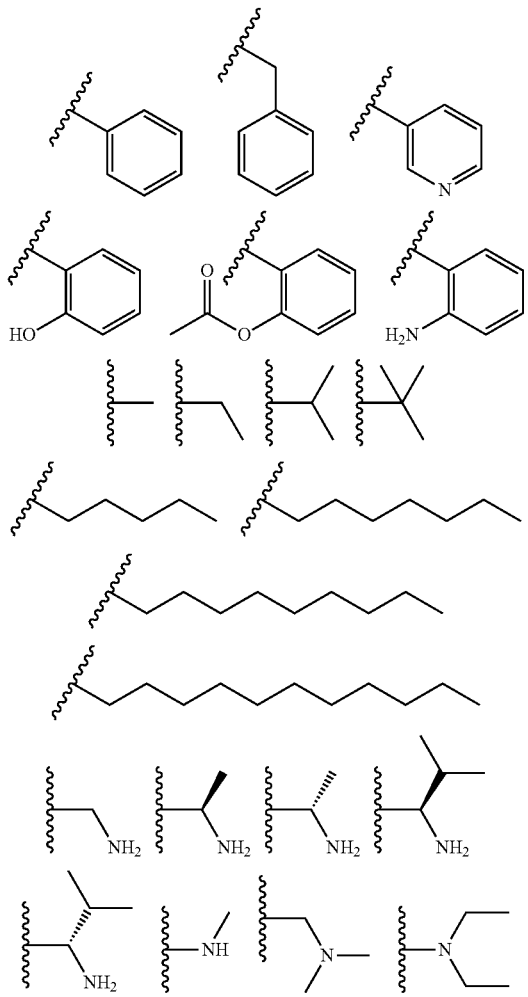

-continued

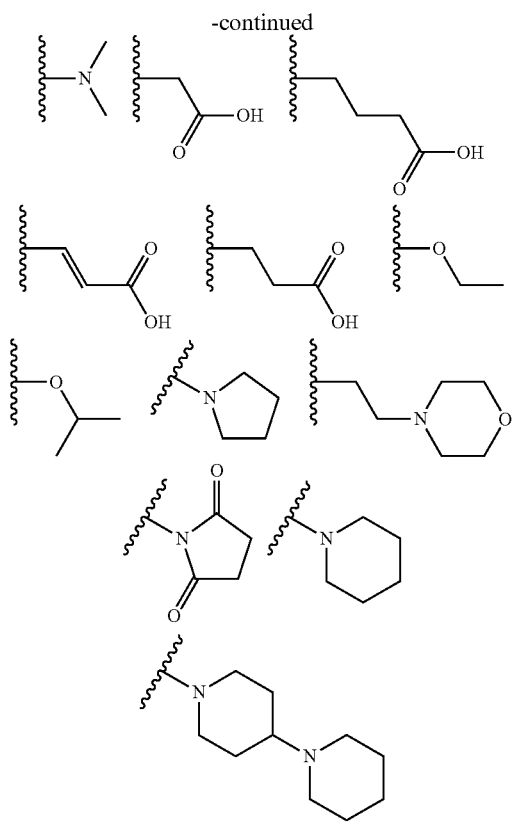

In one embodiment, the present invention is directed to pro-drugs of Eliglustat (formula III) and the geometric isomers, enantiomers, diastereomers, racemates, pharmaceutically acceptable salts and solvates thereof

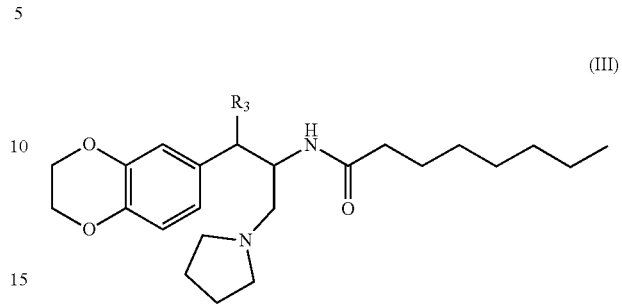

(III)

wherein, $R^3$ is selected from group comprising of:

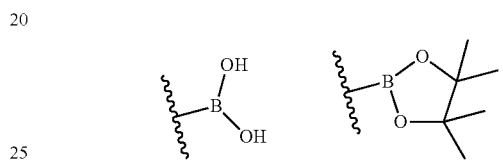

In one embodiment, the present invention is directed to pro-drugs of Eliglustat (formula IV) and the geometric isomers, enantiomers, diastereomers, racemates, pharmaceutically acceptable salts and solvates thereof

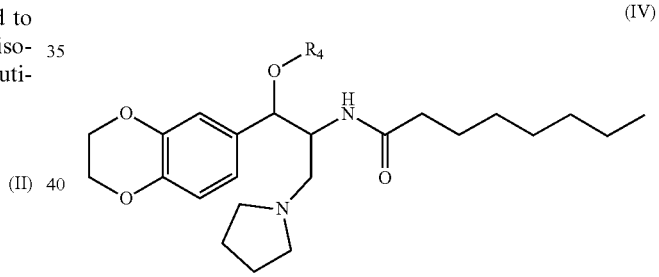

(IV)

wherein, $R^4$ is selected from group comprising of:

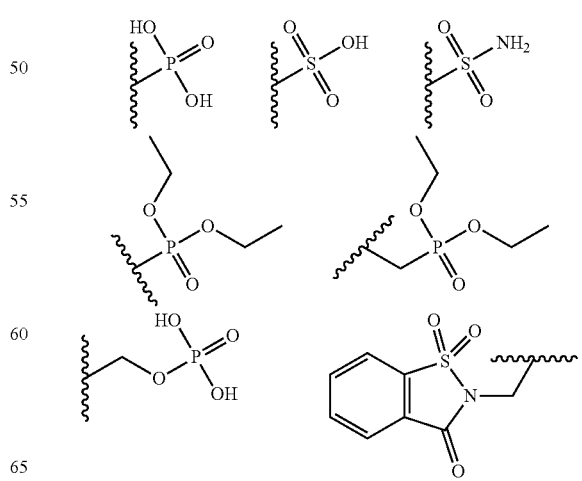

In one embodiment, the present invention is directed to pro-drugs of Eliglustat (formula II) and the geometric isomers, enantiomers, diastereomers, racemates, pharmaceutically acceptable salts and solvates thereof (II)

wherein, $R^2$ is selected from group comprising of:

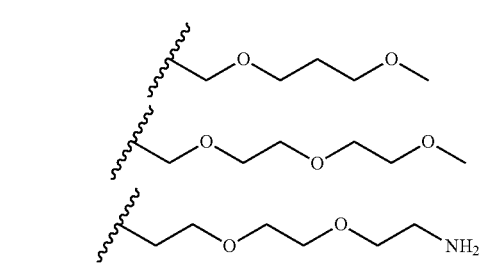

In one embodiment, the present invention is directed to pro-drugs of Eliglustat (formula IX) and the geometric isomers, enantiomers, diastereomers, racemates, pharmaceutically acceptable salts and solvates thereof

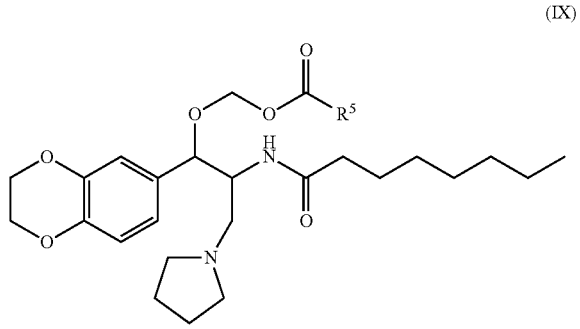

(IX)

wherein, R⁵ is selected from group comprising of:

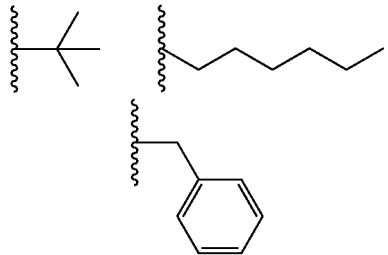

In one embodiment, the present invention is directed to pharmaceutical composition comprising pro-drugs of Eliglustat (formula A) or pharmaceutically acceptable salts or solvates thereof and pharmaceutically acceptable excipients.

In one embodiment, the present invention is directed to use of pro-drugs of Eliglustat (formula A) and pharmaceutically acceptable salts or solvates thereof in treatment of Gaucher disease, Fabry disease, Tay-Sachs disease, Sandhoff disease, GM1 gangliosidosis disease, glomerular disease.

The pro-drugs of Eliglustat (formula A) and pharmaceutically acceptable salts or solvates thereof of the present invention may be administered by a variety of methods. Thus, pro-drugs of Eliglustat (formula A) and pharmaceutically acceptable salts or solvates thereof are active by the oral route and may be administered in solutions, suspensions, emulsions, tablets, including sublingual and intrabuccal tablets, soft gelatin capsules, including solutions used in soft gelatin capsules, aqueous or oil suspensions, emulsions, pills, lozenges, troches, tablets, syrups or elixirs and the like. The pro-drugs of Eliglustat (formula A) and pharmaceutically acceptable salts or solvates thereof are active by parenteral administration and may be administered by depot injection, implants including biodegradable implants, intramuscular and intravenous injections.

Compositions may be prepared according to any method known to the art for the manufacture of pharmaceutical compositions and such compositions may contain one or more agents selected from the group consisting of sweetening agents, flavoring agents, coloring agents and preserving agents. Tablets containing the active ingredient in admixture with nontoxic pharmaceutically acceptable excipients which are suitable for manufacture of tablets are acceptable. These excipients may be, for example, inert diluents, such as calcium carbonate, sodium carbonate, lactose, calcium phosphate or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylmethyl-cellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension may also contain one or more preservatives such as ethyl or n-propyl p-hydroxybenzoate, one or more coloring agents, one or more flavoring agents and one or more sweetening agents, such as sucrose, aspartame or saccharin. Ophthalmic formulations, as is known in the art, will be adjusted for osmotic pressure.

Oil suspensions may be formulated by suspending the active ingredient in a vegetable oil, such as *arachis* oil, olive oil, sesame oil or coconut oil, or in a mineral oil such as liquid paraffin. The oil suspensions may contain a thickening agent, such as beeswax, hard paraffin or cetyl alcohol. Sweetening agents may be added to provide a palatable oral preparation. These compositions may be preserved by the addition of an antioxidant such as ascorbic acid.

Dispersible powders and granules of the invention suitable for preparation of an aqueous suspension by the addition of water may be formulated from the active ingredients in admixture with a dispersing, suspending and/or wetting agent, and one or more preservatives. Suitable dispersing or wetting agents and suspending agents are exemplified by those disclosed above. Additional excipients, for example sweetening, flavoring and coloring agents, may also be present. The pharmaceutical compositions of the invention may also be in the form of oil-in-water emulsions. The oily phase may be a vegetable oil, such as olive oil or *arachis* oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a nontoxic parenterally acceptable diluent or solvent, such as a solution of 1,3-butanediol. Among the acceptable vehicles and solvents that may be employed are water and Ringer's solution, an isotonic sodium chloride. In addition, sterile fixed oils may conventionally be employed as a solvent or suspending medium. For this purpose, any bland fixed oil may be employed including synthetic mono- or diglycerides. In addition, fatty acids such as oleic acid may likewise be used in the preparation of injectables.

The pro-drugs of Eliglustat (formula A) and pharmaceutically acceptable salts or solvates thereof of the present invention may also be administered in the form of suppositories for rectal administration of the drug. These compositions can be prepared by mixing the drug with a suitable nonirritating excipient which is solid at ordinary temperatures but liquid at the rectal temperatures and will therefore melt in the rectum to release the drug. Such materials are cocoa butter and polyethylene glycols.

The pro-drugs of Eliglustat (formula A) and pharmaceutically acceptable salts or solvates thereof of the present invention may be administered by intranasal, intraocular, intravaginal, and intrarectal routes including suppositories, insufflation, powders and aerosol formulations.

The pro-drugs of Eliglustat (formula A) and pharmaceutically acceptable salts or solvates thereof of the present invention may be administered by the topical route and may be administered as applicator sticks, solutions, suspensions, emulsions, gels, creams, ointments, pastes, jellies, paints, powders, and aerosols.

The pro-drugs of Eliglustat (formula A) and pharmaceutically acceptable salts or solvates thereof of the present invention may be administered to any warm-blooded mammal such as humans, domestic pets, and farm animals. The amount of active ingredient that may be combined with a carrier material to produce a single dosage form will vary depending upon the disease treated, the mammalian species, and the particular mode of administration. For example, a unit dose may preferably contain between 0.1 milligram and 1 gram of the active ingredient. A more preferred unit dose is between 0.001 and 0.5 grams. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those of skill in the art.

EXAMPLES

The following examples are provided here to enable one skilled in the art to practice the invention and merely illustrate the process of the present invention. However, it is not intended in any way to limit the scope of the present invention.

1-H NMR spectra are recorded at 400 MHz on a Brucker Avance-III HD. Dimethyl sulfoxide-d6 is used as solvent, and tetramethylsilane (TMS) is used as internal reference standard.

Mass spectra was recorded on a Waters SQD mass spectrometer equipped with an electrospray interface (LC-MS) connected with Acquity H-class system.

Example-1: Preparation of Hemitartrate Salt of Compound of Formula I-a

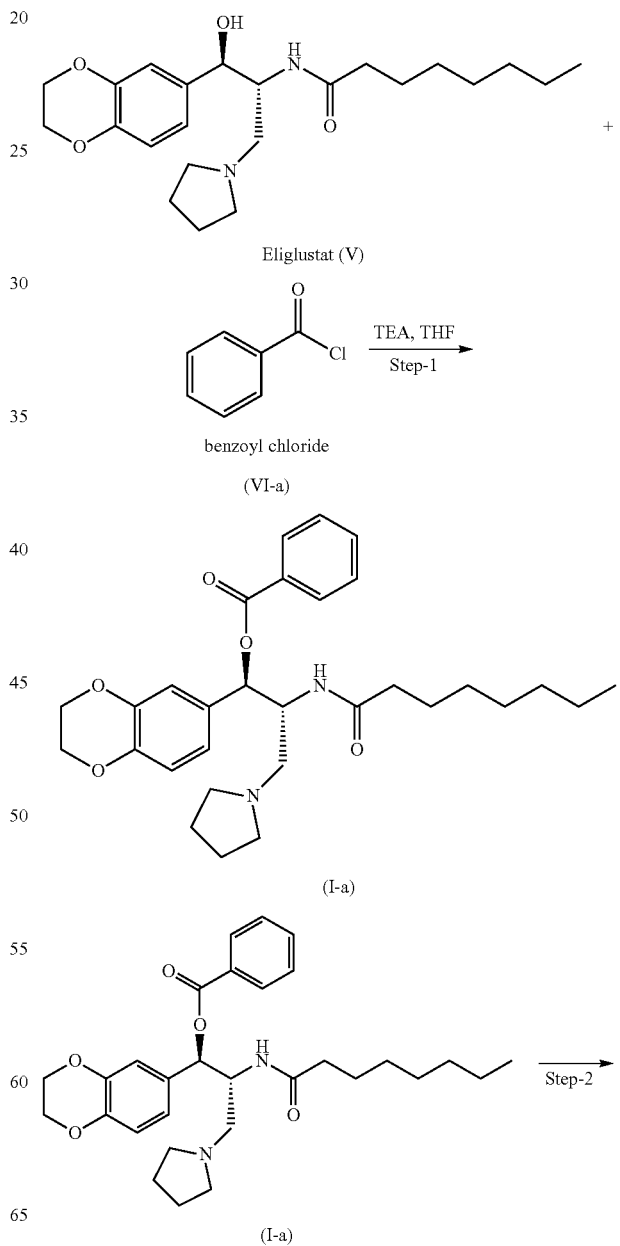

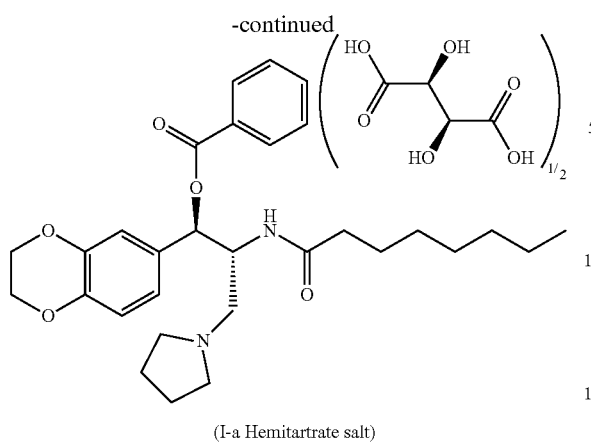

(I-a Hemitartrate salt)

Step-1: Preparation of Compound of formula (I-a) ((1R,2R)-1-(2,3-dihydrobenzo[b][1,4]dioxin-6-yl)-2-octanamido-3-(pyrrolidin-1-yl)propyl benzoate)

Eliglustat (0.300 g) was dissolved in THF (6 ml) at room temperature under nitrogen atmosphere. TEA (0.186 g) was added and the reaction mass was cooled to 5-10° C. under nitrogen atmosphere. Benzyl chloride (0.114 g) in THF (1 ml) was drop wise added at 5-10° C., within 5-10 min light yellow colored suspension formed after completion of addition. The reaction mass was stirred at room temperature for 16-18 hrs. After completion of the reaction, the reaction mass was poured into water (20 ml) and product was extracted by dichloromethane (10 ml×2). The organic layer was separated, washed with saturated NaHCO₃ solution (10 ml×2). The organic layer was separated, dried over sodium sulphate and dried under vacuum at 40° C. to afford the crude product. The crude product was purified by column chromatography using silica gel (100-200 mesh) with elution of 3-5% MeOH in dichloromethane to get pure product (0.20 g). Mass (m/z): 509.4 [M+H]. Yield: 53%

Step-2: Preparation of Hemitartrate Salt of Compound of Formula (I-a)

Step-1 product (I-a, free base) (0.180 g) was dissolved in Acetone (2.16 ml) at room temperature under nitrogen atmosphere. L (+) tartaric acid (0.027 g) was dissolved in Acetone (0.9 ml) and drop wise added to the reaction mass at room temperature under nitrogen atmosphere. The reaction mass was stirred at 40° C. for 2 hrs and at room temperature for overnight. The reaction mass was concentrated and product was triturated with n-pentane. The solvent was decanted, solid product was dried under vacuum to get pure product as hemi-tartrate salt (0.102 g). ¹H NMR (400 MHz, DMSO-d6) δ 8.115-8.137 (d, 2H), 7.980-8.003 (d, 1H), 7.674-7.711 (t, 1H), 574, 7.536-7.574 (t, 2H), 6.791-6.861 (m, 3H), 5.883-5.897 (d, 1H), 4.51-4.61 (m, 1H), 4.222 (s, 1H), 4.198 (s, 4H), 2.82-3.14 (m, 6H), 2.074-2.111 (t, 2H), 1.794 (m, 4H), 1.069-1.348 (m, 10H), 0.808-0.853 (t, 3H). Yield: 44%

Example-2: Preparation of Hemitartrate Salt Compound of Formula (I-b)

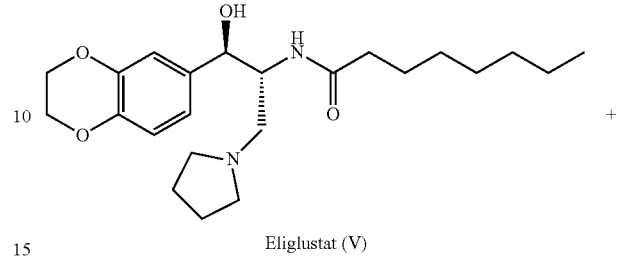

Eliglustat (V)

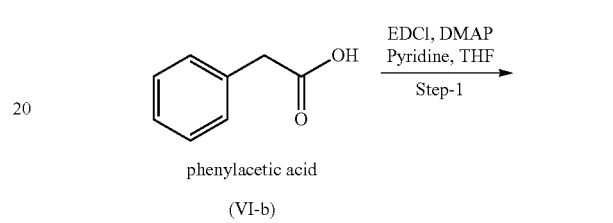

phenylacetic acid
(VI-b)

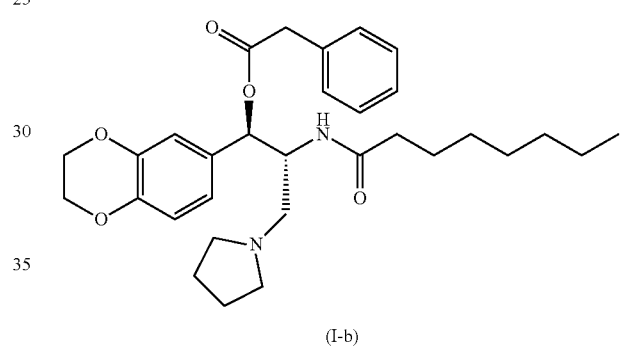

(I-b)

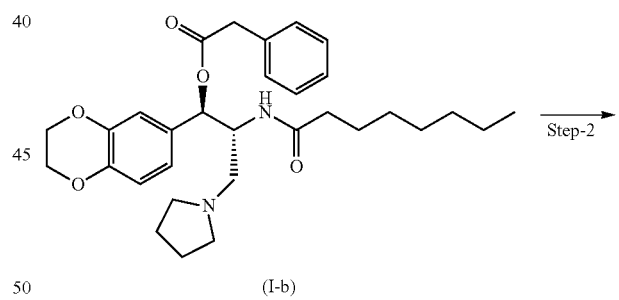

(I-b)

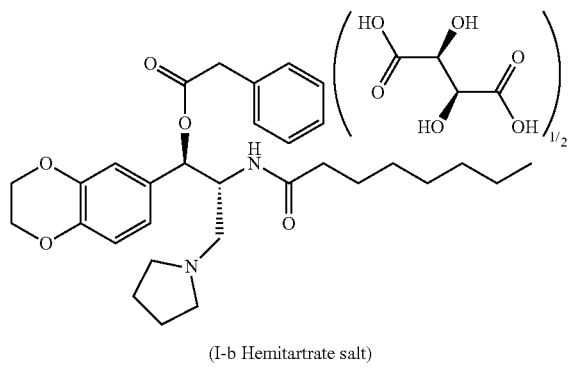

(I-b Hemitartrate salt)

Step-1: Preparation of Compound of Formula (I-b) ((1R,2R)-1-(2,3-dihydrobenzo[b][1,4]dioxin-6-yl)-2-octanamido-3-(pyrrolidin-1-yl)propyl 2-phenylacetate)

Eliglustate (0.250 g) was dissolved in THF (3 mL) at room temperature under nitrogen atmosphere. Pyridine (0.0733 g) and DMAP (0.076 g) were added to the reaction mass at room temperature under nitrogen atmosphere. Phenyl acetic acid (0.251 g) and EDC.HCl (0.14 g) were added to the reaction mass to get off-white solid suspension. The reaction mass was stirred at room temperature under nitrogen atmosphere for 16-18 hrs. After completion of the reaction, the reaction mass was poured into water (10 ml) and product was extracted by dichloromethane (5 ml×2). The organic layer was separated, washed with saturated NaHCO₃ solution (5 ml×2). The organic layer was separated, dried over sodium sulphate and dried under vacuum at 40° C. to afford the crude product. The crude product was purified by column chromatography using silica gel (100-200 mesh) with elution of 4-5% MeOH in dichloromethane to get pure product (0.080 g) Mass (m/z): 523.3[M+H]. Yield: 24%

Step-2: Preparation of Hemitartrate Salt of Compound of Formula (I-b)

Step-1 product (I-b, free base) (0.080 g) was dissolved in Acetone (1.0 ml) at room temperature under nitrogen atmosphere. L (+) tartaric acid (0.011 g) was dissolved in Acetone (0.3 ml) was drop wise added to the reaction mass at room temperature under nitrogen atmosphere. The reaction mass was stirred at 40° C. for 2 hrs and at room temperature for overnight. The reaction mass was concentrated and product was triturated with n-pentane. The solvent was decanted, solid product was dried under vacuum to get pure product as hemi-tartrate salt (0.035 g). ¹H NMR (400 MHz, DMSO-d6) δ 7.763 (d, 1H), 7.244-7.325 (m, 5H), 6.688-6.768 (m, 3H), 5.656 (d, 1H), 4.35 (s, 1H), 4.229 (s, 1H), 4.201 (s, 4H), 3.725 (s, 2H), 3.560 (s, 2H), 2.7-2.9 (m, 6H), 2.074-2.111 (t, 2H), 1.62-1.72 (m, 4H), 1.14-1.41 (m, 10H), 0.843-0.876 (t, 3H). Yield: 38%

Example-3: Preparation of Hemitartrate Salt Compound of Formula (I-c)

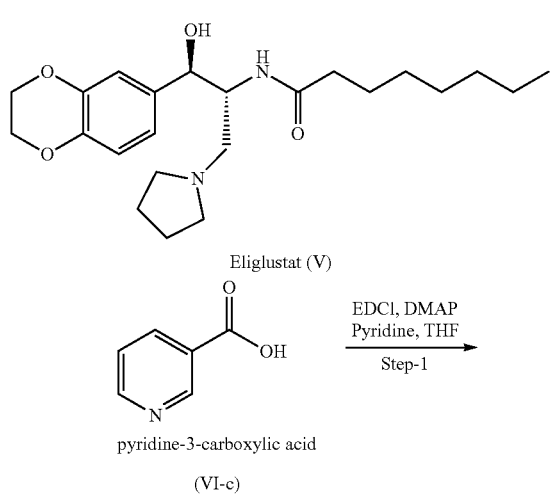

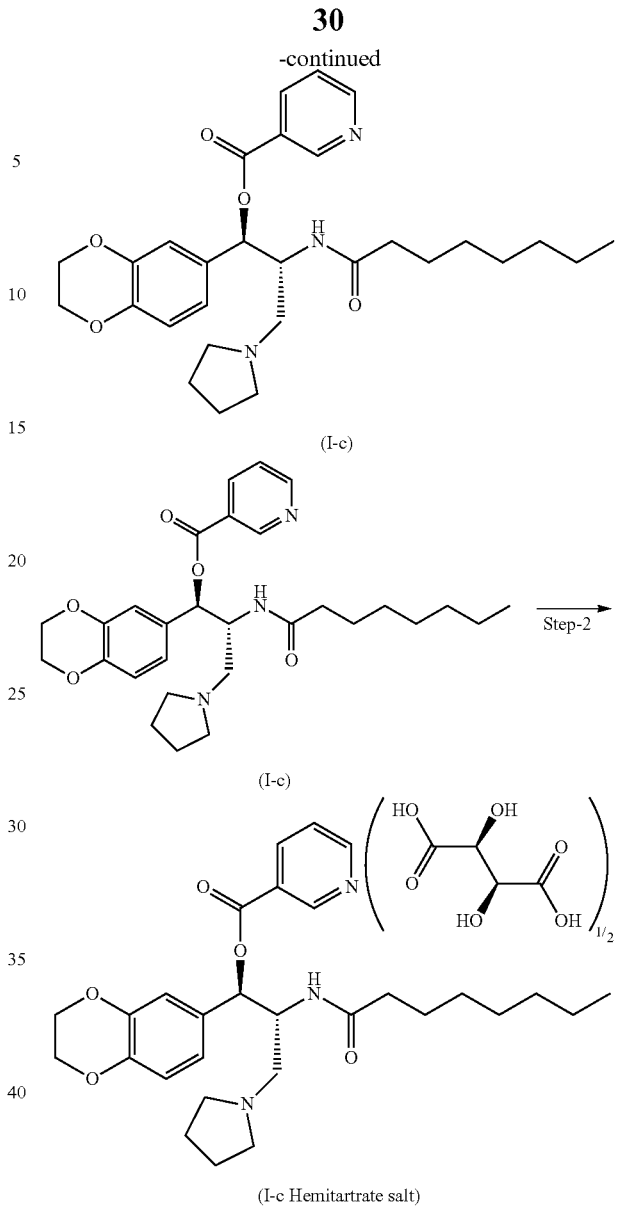

Step-1: Preparation of Compound of Formula (I-c) ((1R,2R)-1-(2,3-dihydrobenzo[b][1,4]dioxin-6-yl)-2-octanamido-3-(pyrrolidin-1-yl)propyl nicotinate)

Eliglustate (0.200 g) was dissolved in THF (2 ml) at room temperature under nitrogen atmosphere. Pyridine (0.056 g) and DMAP (0.011 g) were added to the reaction mass at room temperature under nitrogen atmosphere. Pyridine-3-carboxylic acid (0.181 g) and EDC.HCl (0.108 g) were added to the reaction mass to get light brown solid suspension. The reaction mass was stirred at room temperature for 16-18 hours under nitrogen atmosphere. After completion of the reaction, the reaction mass was poured into water (10 ml) and product was extracted by dichloromethane (10 ml×2). The organic layer was separated, washed with saturated NaHCO₃ solution (5 ml×2). The organic layer was separated, dried over sodium sulphate and dried under vacuum at 40° C. to afford the crude product. The crude product was purified by column chromatography using silica gel (100-

200 mesh) with elution of 4-5% MeOH in dichloromethane to get pure product (0.100 g). Mass (m/z): 510.3[M+H]. Yield: 39%

Step-2: Preparation of Hemitartrate Salt of Compound of Formula (I-c)

Step-1 product (I-c, free base) (0.080 g) was dissolved in Acetone (0.8 ml) at room temperature under nitrogen atmosphere. L (+) tartaric acid (0.011 g) was dissolved in Acetone (0.24 ml) was drop wise added to the reaction mass at room temperature under nitrogen atmosphere. The reaction mass was stirred at 40° C. for 2 hrs and at room temperature for overnight. The reaction mass was concentrated and product was triturated with n-pentane. The solvent was decanted, solid product was dried under vacuum to get pure product as hemi-tartrate salt (0.050 g). $^1$H NMR (400 MHz, DMSO-d6) δ 7.763 (d, 1H), 7.244-7.325 (m, 5H), 6.688-6.768 (m, 3H), 5.656 (d, 1H), 4.35 (s, 1H), 4.229 (s, 1H), 4.201 (s, 4H), 3.725 (s, 2H), 3.560 (s, 2H), 2.7-2.9 (m, 6H), 2.063-2.102 (t, 2H), 1.75-1.85 (m, 4H), 1.10-1.41 (m, 10H), 0.811-0.848 (t, 3H). Yield: 54%

Example-4: Preparation of Hemitartrate Salt Compound of Formula (I-d)

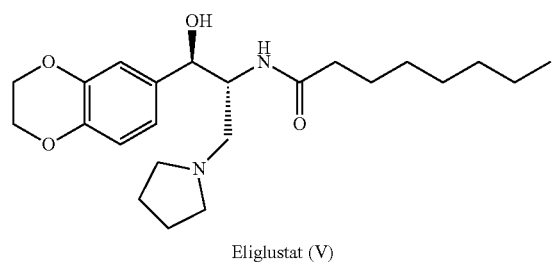

Eliglustat (V)

+

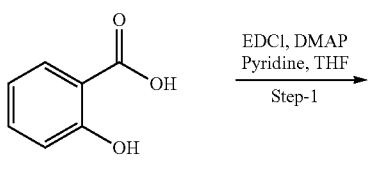

2-hydroxybenzoic acid
(VI-d)

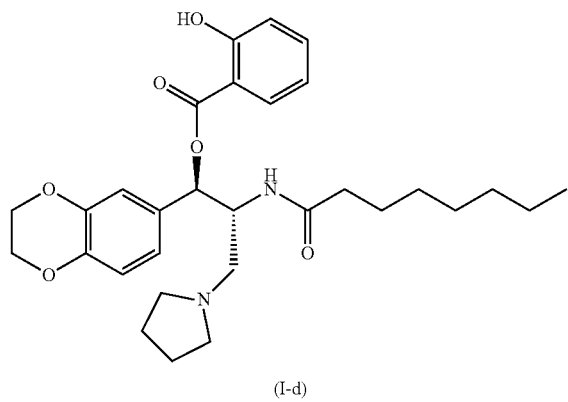

(I-d)

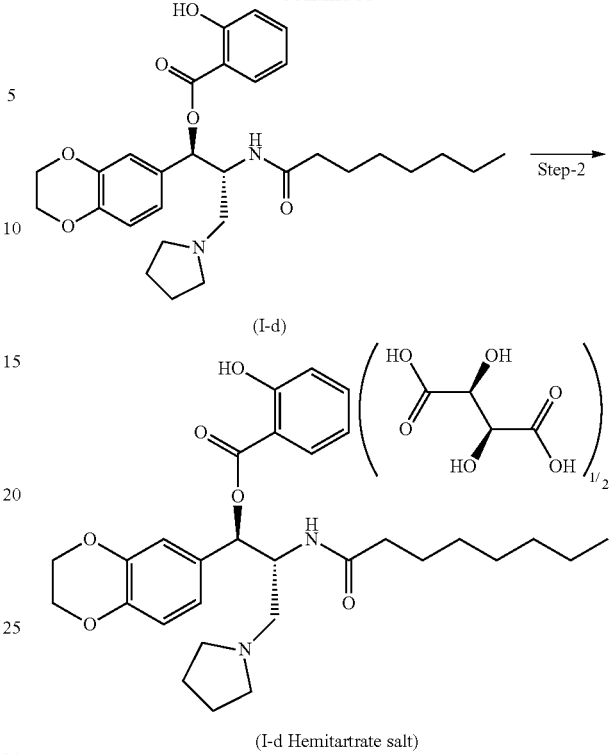

Step-1: Preparation of Compound of Formula (I-d) ((1R,2R)-1-(2,3-dihydrobenzo[b][1,4]dioxin-6-yl)-2-octanamido-3-(pyrrolidin-1-yl)propyl 2-hydroxybenzoate)

Eliglustat (0.200 g) was dissolved in THF (2 ml) at room temperature under nitrogen atmosphere. Pyridine (0.0586 g) and DMAP (0.012 g) were added to the reaction mass at room temperature under nitrogen atmosphere. Salicylic acid (0.200 g) and EDC.HCl (0.108 g) were added to the reaction mass to get light yellow solid suspension. The reaction mass was stirred at room temperature for 16-18 hours under nitrogen atmosphere. After completion of the reaction, the reaction mass was poured into water (10 ml) and product was extracted by dichloromethane (10 ml×2). The organic layer was separated, washed with saturated NaHCO$_3$ solution (5 ml×2). The organic layer was separated, dried over sodium sulphate and dried under vacuum at 40° C. to afford the crude product. The crude product was purified by column chromatography using silica gel (100-200 mesh) with elution of 4-5% MeOH in dichloromethane to get pure product (0.080 g). Mass (m/z): 525.2 [M+H]. Yield: 30%

Step-2: Preparation of Hemitartrate Salt of Compound of Formula (I-d)

Step-1 product (I-d, free base) (0.050 g) was dissolved in Acetone (0.6 ml) at room temperature under nitrogen atmosphere. L (+) tartaric acid (0.007 g) was dissolved in Acetone (0.3 ml) and drop wise added to the reaction mass at room temperature under nitrogen atmosphere. The reaction mass was stirred at 40° C. for 2 hrs and at room temperature for overnight. The reaction mass was concentrated and product was triturated with n-pentane. The solvent was decanted, solid product was dried under vacuum to get pure product as hemi-tartrate salt (0.037 g). ¹H NMR (400 MHz, DMSO-d6) δ 8.128-8.152 (d, 1H), 7.895-8.008 (d, 1H), 7.536-7.579 (t, 1H), 6.968-7.019 (m, 2H), 6.804-6.876 (m, 3H), 5.918-5.932 (d, 1H), 4.55 (s, 1H), 4.232 (s, 1H), 4.194 (s, 4H), 3.560 (s, 2H), 2.7-2.9 (m, 6H), 2.058-2.094 (t, 2H), 1.75-1.85 (m, 4H), 1.10-1.41 (m, 10H), 0.811-0.848 (t, 3H).

Yield: 64%

Example-5: Preparation of Hemitartrate Salt Compound of Formula (I-e)

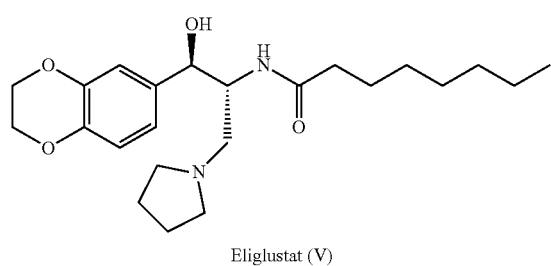

Eliglustat (V)

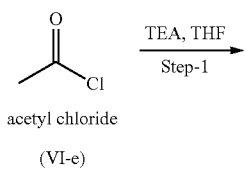

acetyl chloride
(VI-e)

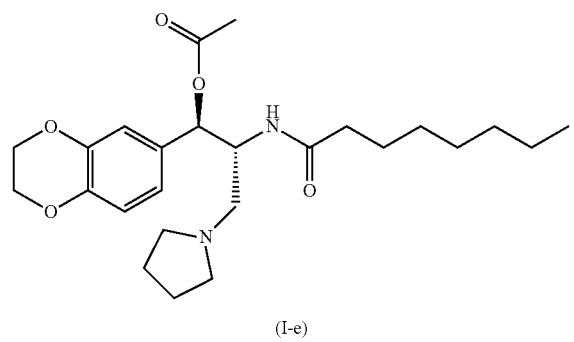

(I-e)

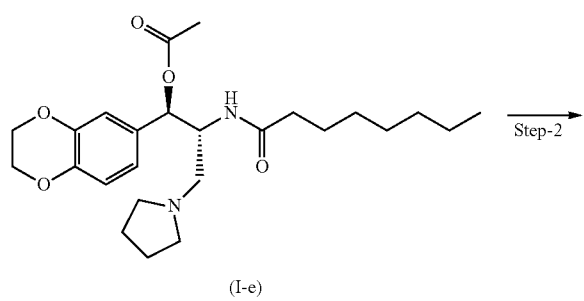

(I-e)

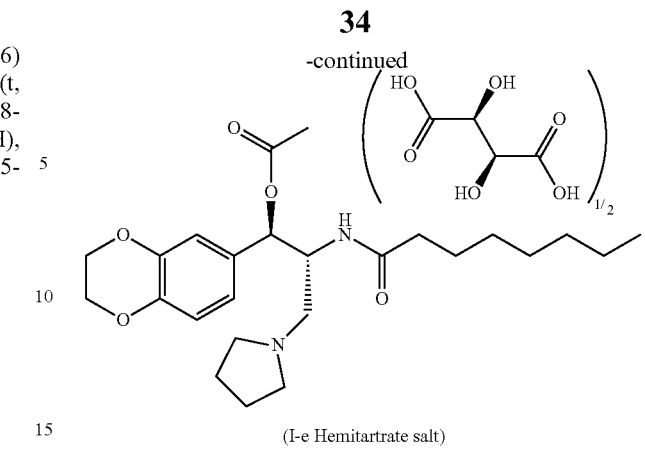

(I-e Hemitartrate salt)

Step-1: Preparation of Compound of Formula (I-e) ((1R,2R)-1-(2,3-dihydrobenzo[b][1,4]dioxin-6-yl)-2-octanamido-3-(pyrrolidin-1-yl)propyl acetate)

Eliglustat (0.400 g) was dissolved in THF (8 mL) at room temperature under nitrogen atmosphere. TEA (0.249 g) was added and the reaction mass was cooled to 5-10° C. under nitrogen atmosphere. Acetyl chloride (0.084 g) in THF (1 ml) was drop wise added at 5-10° C., within 5-10 min light grey colored suspension formed after completion of addition. The reaction mass was stirred at room temperature for 16-18 hrs. After completion of the reaction, the reaction mass was poured into water (20 ml) and product was extracted by dichloromethane (10 ml×2). The organic layer was separated, washed with saturated NaHCO₃ solution (10 ml×2). The organic layer was separated, dried over sodium sulphate and dried under vacuum at 40° C. to afford the crude product. The crude product was purified by column chromatography using silica gel (100-200 mesh) with elution of 3-4% MeOH in dichloromethane to get pure product (0.350 g). Mass (m/z): 447.4 [M+H]. Yield: 79%

Step-2: Preparation of Hemitartrate Salt of Compound of Formula (I-e)

Step-1 product (I-e, free base) (0.350 g) was dissolved in Acetone (3.78 ml) at room temperature under nitrogen atmosphere. L (+) tartaric acid (0.053 g) was dissolved in Acetone (1.7 ml) and drop wise added to the reaction mass at room temperature under nitrogen atmosphere. The reaction mass was stirred at 40° C. for 2 hrs and at room temperature for overnight. The reaction mass was concentrated and product was triturated with n-pentane. The solvent was decanted, solid product was dried under vacuum to get pure product (0.340 g). ¹H NMR (400 MHz, DMSO-d6) δ 7.894-7.917 (d, 1H), 6.743-6.782 (m, 3H), 5.656-5.667 (d, 1H), 4.416 (s, 1H), 4.205 (s, 4H), 4.165 (s, 1H), 2.88-3.18 (m, 5H), 2.511-2.065 (s, 5H), 1.71-1.84 (m, 4H), 1.15-1.41 (m, 10H), 0.842-0.876 (t, 3H). Yield: 84%

Example-6: Preparation of Hemitartrate Salt Compound of Formula (I-f)

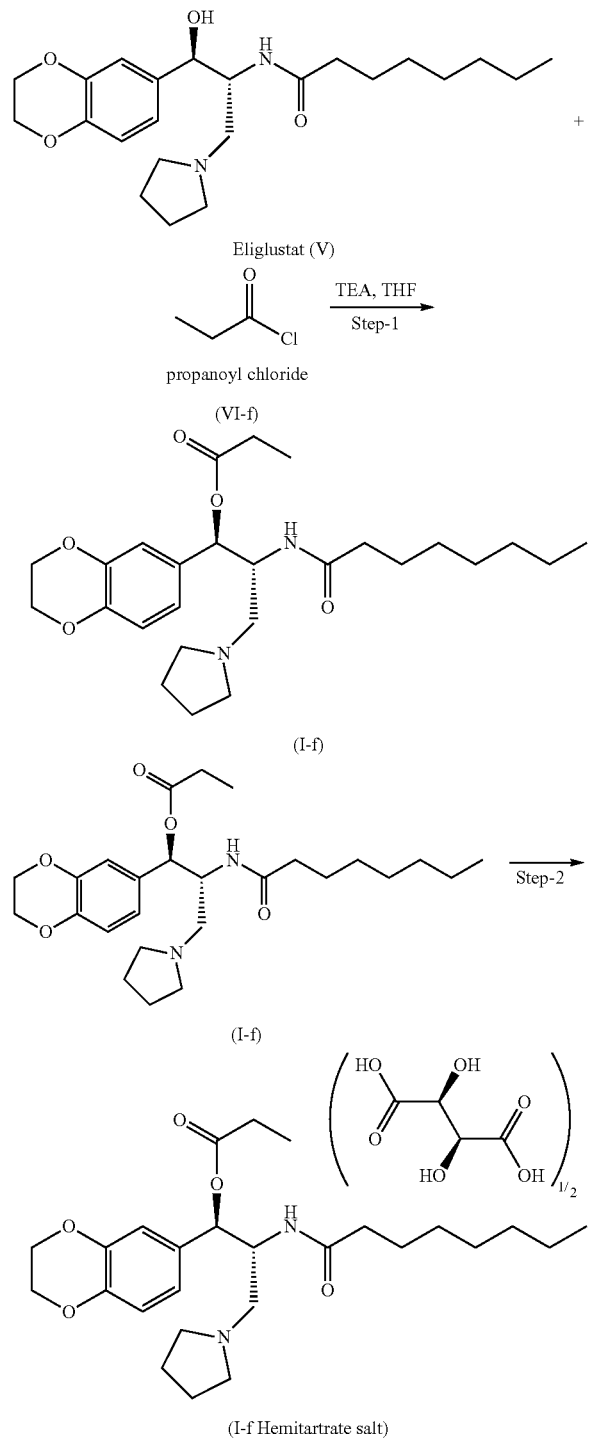

Step-1: Preparation of Compound of Formula (I-f) ((1R,2R)-1-(2,3-dihydrobenzo[b][1,4]dioxin-6-yl)-2-octanamido-3-(pyrrolidin-1-yl)propyl propionate)

Eliglustat (0.300 g) was dissolved in THF (6 ml) at room temperature under nitrogen atmosphere. TEA (0.186 g) was added and the reaction mass was cooled to 5-10° C. under nitrogen atmosphere. Propanoyl chloride (0.100 g) in THF (1 ml) was drop wise added at 5-10° C., within 5-10 min off-white colored suspension formed after completion of addition. The reaction mass was stirred at room temperature for 16-18 hrs. After completion of the reaction, the reaction mass was poured into water (20 ml) and product was extracted by dichloromethane (10 ml×2). The organic layer was separated, washed with saturated $NaHCO_3$ solution (10 ml×2). The organic layer was separated, dried over sodium sulphate and dried under vacuum at 40° C. to afford the crude product. The crude product was purified by column chromatography using silica gel (100-200 mesh) with elution of 3-4% MeOH in dichloromethane to get pure product (0.230 g). Mass (m/z): 461.3 [M+H]. Yield: 67%

Step-2: Preparation of Hemitartrate Salt of Compound of Formula (I-f)

Step-1 product (I-f, free base) (0.090 g) was dissolved in Acetone (1.08 ml) at room temperature under nitrogen atmosphere. L (+) tartaric acid (0.014 g) was dissolved in Acetone (0.5 ml) and drop wise added to the reaction mass at room temperature under nitrogen atmosphere. The reaction mass was stirred at 40° C. for 2 hrs and at room temperature for overnight. The reaction mass was concentrated and product was triturated with n-pentane. The solvent was decanted, solid product was dried under vacuum to get pure product (0.100 g). $^1$H NMR (400 MHz, CDCl3) δ 7.215 (bs, 1H), 6.643-6.807 (m, 3H), 5.683-5.699 (d, 1H), 4.722 (s, 1H), 4.219 (s, 5H), 3.411-3.741 (t, 1H), 2.9-3.23 (bs, 2H), 2.641-2.663 (d, 1H), 2.31-245 (m, 4H), 1.9-2.28 (m, 4H), 1.19-1.41 (m, 10H), 0.102-1.139 (t, 3H), 0.857-0.921 (t, 3H). Yield: 96%

Example-7: Preparation of Hemitartrate Salt Compound of Formula (I-g)

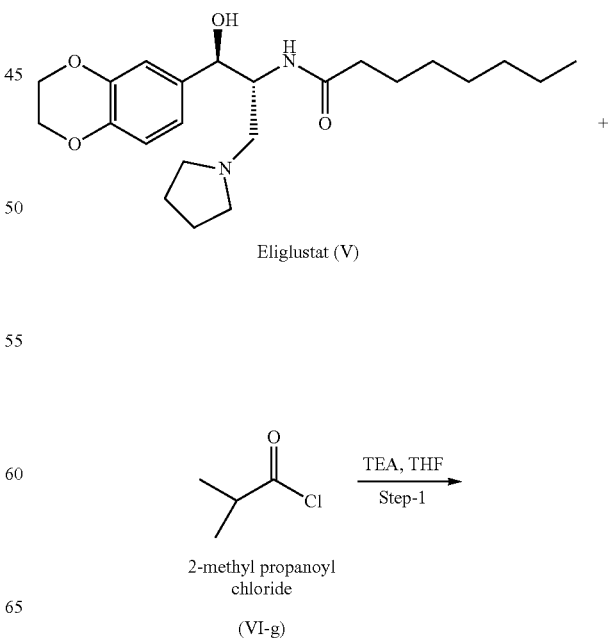

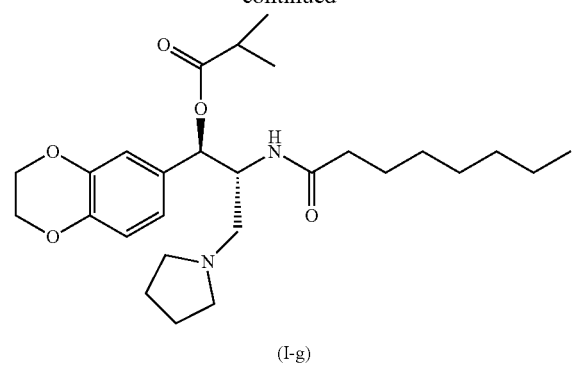

(I-g)

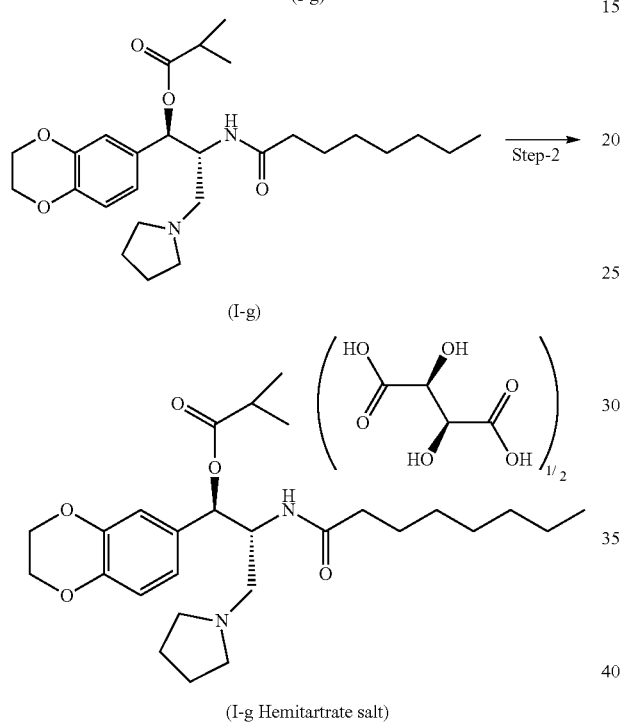

(I-g)

(I-g Hemitartrate salt)

Step-1: Preparation of Compound of Formula (I-g) ((1R,2R)-1-(2,3-dihydrobenzo[b][1,4]dioxin-6-yl)-2-octanamido-3-(pyrrolidin-1-yl)propyl isobutyrate)

Eliglustat (0.300 g) was dissolved in THF (6 ml) at room temperature under nitrogen atmosphere. TEA (0.186 g) was added and the reaction mass was cooled to 5-10° C. under nitrogen atmosphere. 2-methylpropanoyl chloride (0.120 g) in THF (1 ml) was drop wise added at 5-10° C., within 5-10 min light yellow colored suspension formed after completion of addition. The reaction mass was stirred at room temperature for 16-18 hrs. After completion of the reaction, the reaction mass was poured into water (20 ml) and product was extracted by dichloromethane (10 ml×2). The organic layer was separated, washed with saturated NaHCO$_3$ solution (10 ml×2). The organic layer was separated, dried over sodium sulphate and evaporated under vacuum at 40° C. to afford the crude product. The crude product was purified by column chromatography using silica gel (100-200 mesh) with elution of 3-4% MeOH in dichloromethane to get pure product (0.200 g). Mass (m/z): 475.3 [M+H]. Yield: 56%

Step-2: Preparation of Hemitartrate Salt of Compound of Formula (I-g)

Step-1 product (I-g, free base) (0.100 g) was dissolved in Acetone (1.18 ml) at room temperature under nitrogen atmosphere. L (+) tartaric acid (0.015 g) was dissolved in Acetone (0.5 ml) and added drop wise to the reaction mass at room temperature under nitrogen atmosphere. The reaction mass was stirred at 40° C. for 2 hrs and at room temperature for overnight. The reaction mass was concentrated and product was triturated with n-pentane. The solvent was decanted, solid product was dried under vacuum to get pure product (0.090 g). $^1$H NMR (400 MHz, DMSO-d6) δ 7.799-7.822 (d, 1H), 6.734-6.812 (m, 3H), 5.631-5.642 (d, 1H), 4.416 (s, 1H), 2.255 (s, 1H), 4.210 (s, 4H), 3.22-3.31 (m, 4H), 2.82-3.14 (m, 5H), 2.511-2.18 (m, 2H), 1.71-1.84 (m, 4H), 1.157-1.379 (m, 13H), 1.086-1.124 (t, 3H), 0.843-0.877 (t, 3H). Yield: 78%

Example-8: Preparation of Hemitartrate Salt Compound of Formula (I-h)

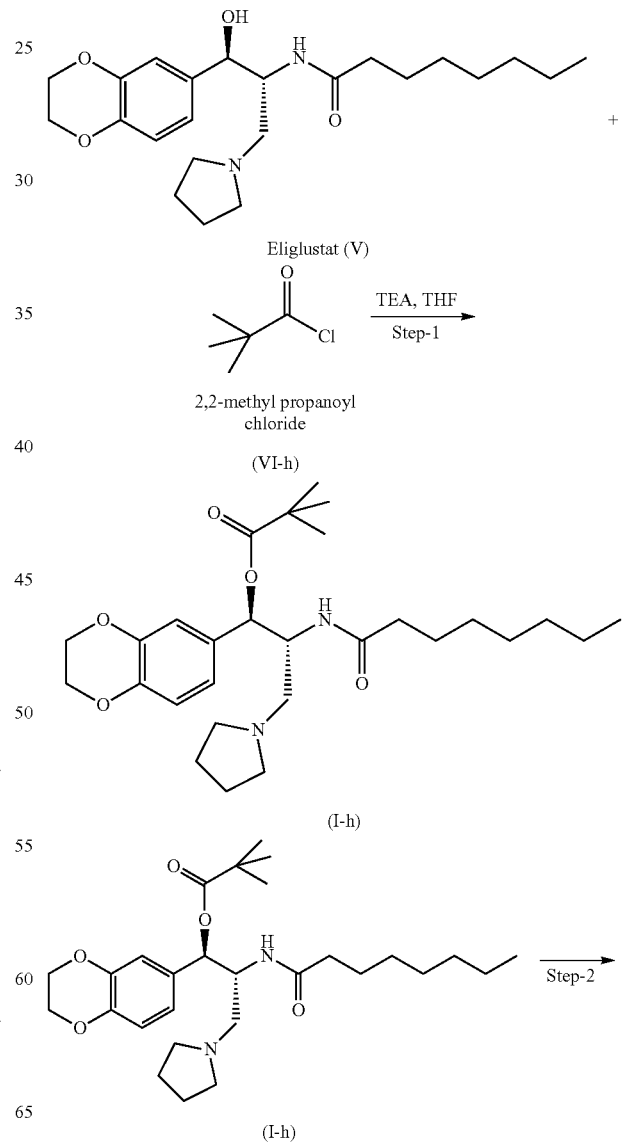

(I-h)

-continued

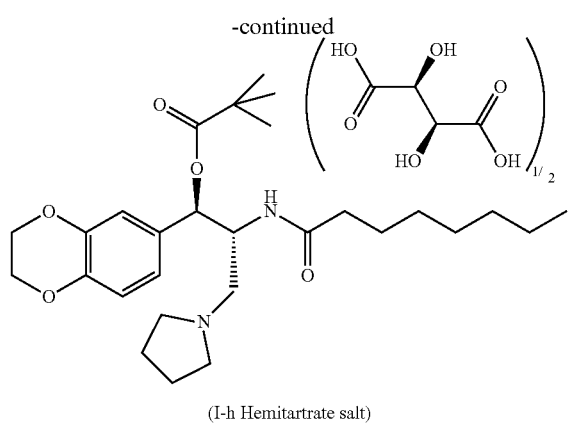

(I-h Hemitartrate salt)

Step-1: Preparation of Compound of Formula (I-h) ((1R,2R)-1-(2,3-dihydrobenzo[b][1,4]dioxin-6-yl)-2-octanamido-3-(pyrrolidin-1-yl)propyl pivalate)

Eliglustat (0.300 g) was dissolved in THF (6 ml) at room temperature under nitrogen atmosphere. TEA (0.186 g) was added and the reaction mass was cooled to 5-10° C. under nitrogen atmosphere. Pivaloyl chloride (0.130 g) in THF (1 ml) was drop wise added at 5-10° C., within 5-10 min light yellow colored suspension formed after completion of addition. The reaction mass was stirred at room temperature for 16-18 hrs. After completion of the reaction, the reaction mass was poured into water (15 ml) and product was extracted by dichloromethane (10 ml×2). The organic layer was separated, washed with saturated NaHCO$_3$ solution (5 ml×2). The organic layer was separated, dried over sodium sulphate and dried under vacuum at 40° C. for 30 minutes to afford the crude product. The crude product was purified by column chromatography using silica gel (100-200 mesh) with elution of 3-4% MeOH in dichloromethane to get pure product (0.180 g).

Mass (m/z): 489.3 [M+H]. Yield: 49%

Step-2: Preparation of Hemitartrate Salt of Compound of Formula (I-h)

Step-1 product (I-h, free bases) (0.108 g) was dissolved in Acetone (1.3 ml) at room temperature under nitrogen atmosphere. L (+) tartaric acid (0.016 g) was dissolved in acetone (0.5 ml) and drop wise added to the reaction mass at room temperature under nitrogen atmosphere. The reaction mass was stirred at 40° C. for 2 hrs and at room temperature for overnight. The reaction mass was concentrated and product was triturated with n-pentane. The solvent was decanted, solid product was dried under vacuum to get pure product (0.090 g). $^1$H NMR (400 MHz, DMSO-d6) δ 7.775-7.798 (d, 1H), 6.714-6.804 (m, 3H), 5.588-5.601 (d, 1H), 4.399 (bs, 1H), 4.201 (d, 5H), 3.22-3.31 (m, 4H), 2.73-3.0 (m, 5H), 2.13-2.15 (t, 2H), 1.791 (bs, 4H), 1.19-1.41 (m, 10H), 1.116 (s, 9H), 0.842-0.876 (t, 3H). Yield: 72%

Example-9: Preparation of Hemitartrate Salt Compound of Formula (I-i)

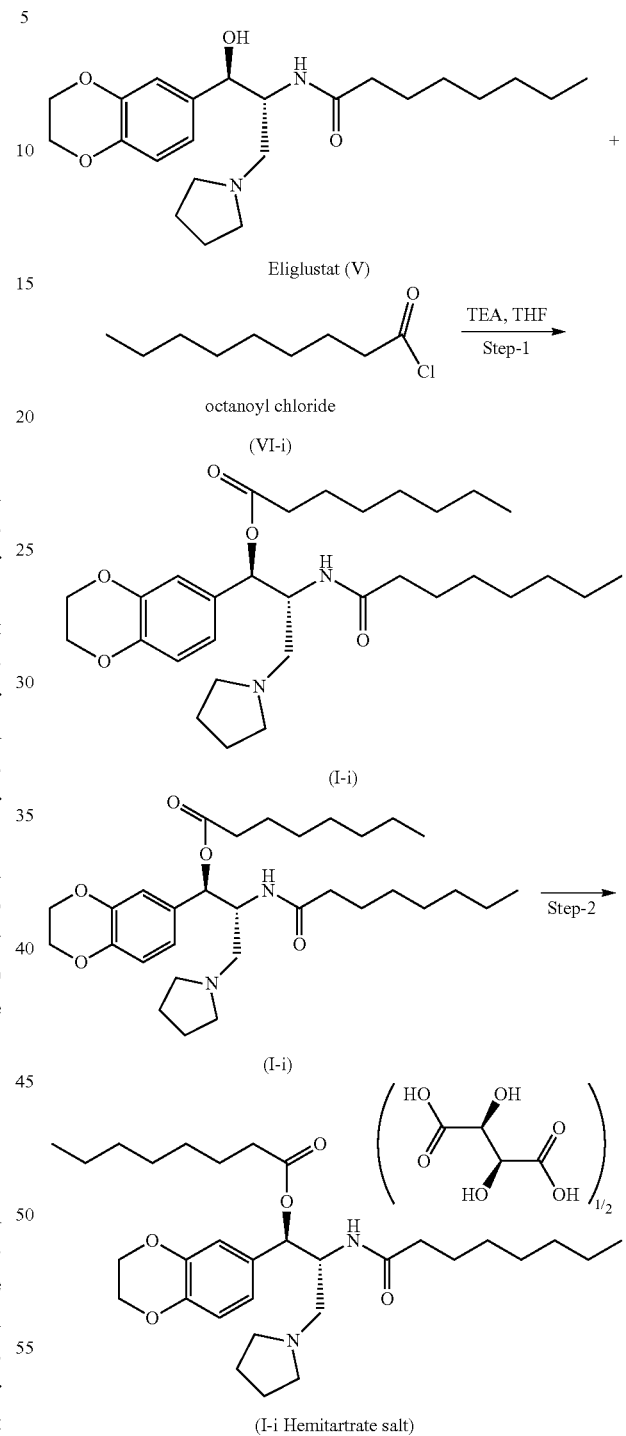

Step-1: Preparation of Compound of Formula (I-i) ((1R,2R)-1-(2,3-dihydrobenzo[b][1,4]dioxin-6-yl)-2-octanamido-3-(pyrrolidin-1-yl)propyl octanoate)

Eliglustat (0.300 g) was dissolved in THF (6 ml) at room temperature under nitrogen atmosphere. TEA (0.186 g) was added and the reaction mass was cooled to 5-10° C. under nitrogen atmosphere. Octanoyl chloride (0.179 g) in THF (1 ml) was drop wise added at 5-10° C., within 5-10 min light orange colored suspension formed after completion of addition. The reaction mass was stirred at room temperature for 16-18 hrs. After completion of the reaction, the reaction mass was poured into water (10 ml) and product was extracted by dichloromethane (5 ml×2). The organic layer was separated, washed with saturated NaHCO₃ solution (5 ml×2). The organic layer was separated, dried over sodium sulphate and dried under vacuum at 40° C. for 30 minutes to afford the crude product. The crude product was purified by column chromatography using silica gel (100-200 mesh) with elution of 3-4% MeOH in dichloromethane to get pure product (0.200 g). Mass (m/z): 503.3 [M+H]. Yield: 50%

Step-2: Preparation of Hemitartrate Salt of Compound of Formula (I-i)

Step-1 product (I-i, free base) (0.080 g) was dissolved in Acetone (1.5 ml) at room temperature under nitrogen atmosphere. L (+) tartaric acid (0.011 g) was dissolved in Acetone (0.5 ml) was drop wise added to the reaction mass at room temperature under nitrogen atmosphere. The reaction mass was stirred at 40° C. for 2 hrs and at room temperature for overnight. The reaction mass was concentrated and product was triturated with n-pentane. The solvent was decanted, solid product was dried under vacuum to get pure product (0.043 g). ¹H NMR (400 MHz, CDCl3) δ 8.6759 (bs, 1H), 7.577 (bs, 1H), 6.820-6.872 (d, 3H), 5.756-5.770 (d, 1H), 4.790 (bs, 1H), 4.320 (bs, 1H), 4.237 (s, 4H), 4.030-4.088 (t, 1H), 3.922 (bs, 1H), 2.7-3.0 (m, 3H), 2.672 (bs, 1H), 2.35-2.5 (m, 4H), 1.95-2.3 (m, 2H), 1.8-2.2 (m, 6H), 1.5-1.62 (m, 4H), 1.11-1.4 (m, 10H), 0.822-0.872 (m, 6H). Yield: 47%

Example-10: Preparation of Hemitartrate Salt Compound of Formula (I-j)

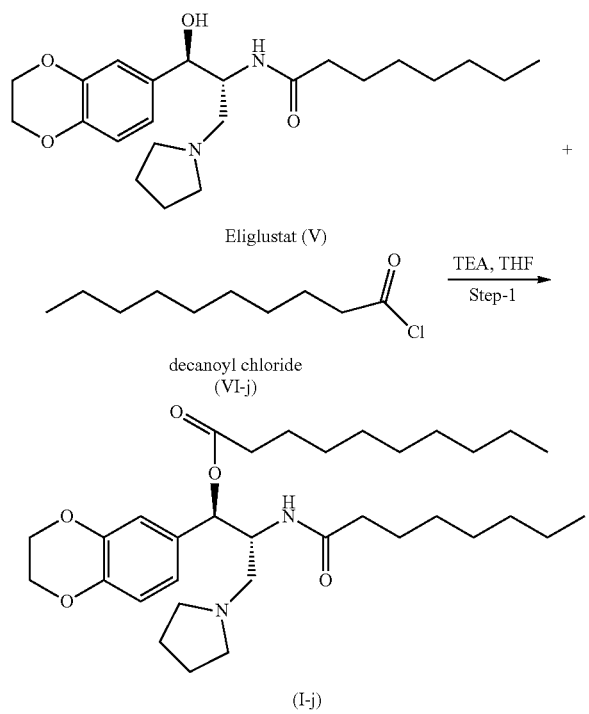

Step-1: Preparation of Compound of Formula (I-j) ((1R,2R)-1-(2,3-dihydrobenzo[b][1,4]dioxin-6-yl)-2-octanamido-3-(pyrrolidin-1-yl)propyl decanoate)

Eliglustat (0.300 g) was dissolved in THF (6 ml) at room temperature under nitrogen atmosphere. TEA (0.186 g) was added and the reaction mass was cooled to 5-10° C. under nitrogen atmosphere. Decanoyl chloride (0.211 g) in THF (1 ml) was drop wise added at 5-10° C., within 5-10 min off-white yellow colored suspension formed after completion of addition. The reaction mass was stirred at room temperature for 16-18 hrs. After completion of the reaction, the reaction mass was poured into water (10 ml) and product was extracted by dichloromethane (5 ml×2). The organic layer was separated, washed with saturated NaHCO₃ solution (5 ml×2). The organic layer was separated, dried over sodium sulphate and dried under vacuum at 40° C. for 30 minutes to afford the crude product. The crude product was purified by column chromatography using silica gel (100-200 mesh) with elution of 3-4% MeOH in dichloromethane to get pure product (0.190 g). Mass (m/z): 559.3 [M+H]. Yield: 45%

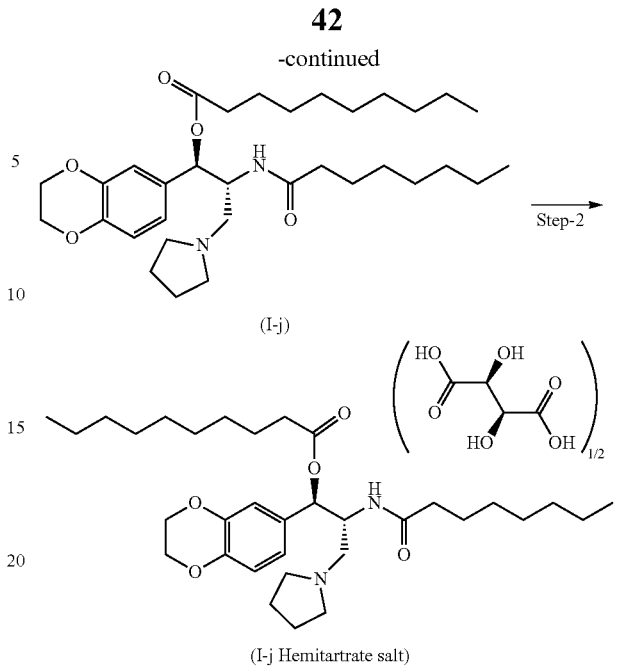

Step-2: Preparation of Hemitartrate Salt of Compound of Formula (I-i)

Step-1 product (I-j, free base) (0.16 g) was dissolved in Acetone (2.0 ml) at room temperature under nitrogen atmosphere. L (+) tartaric acid (0.021 g) was dissolved in Acetone (0.7 ml) and drop wise added to the reaction mass at room temperature under nitrogen atmosphere. The reaction mass was stirred at 40° C. for 2 hrs and at room temperature for overnight. The reaction mass was concentrated and product was triturated with n-pentane. The solvent was decanted, solid product was dried under vacuum to get pure product (0.10 g). ¹H NMR (400 MHz, CDCl3) δ 9.047 (bs, 1H), 7.288-7.314 (d, 1H), 6.793-6.849 (m, 3H), 5.684-5.701 (d, 1H), 4.7-4.81 (m, 1H), 4.36 (bs, 1H), 4.230 (s, 4H), 4.018-4.075 (t, 1H), 3.875-3.886 (bs, 1H), 2.7-2.9 (m, 2H), 2.58-2.64 (m, 1H), 1.7-2.5 (m, 10H), 1.519-1.589 (m, 4H), 1.18-1.31 (m, 14H), 0.837-0.870 (m, 6H). Yield: 55%

Example-11: Preparation of Hemitartrate Salt Compound of Formula (I-k)
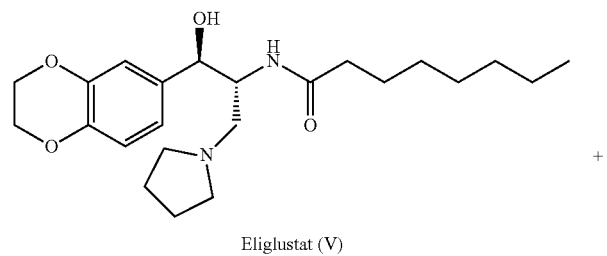
Eliglustat (V)
+
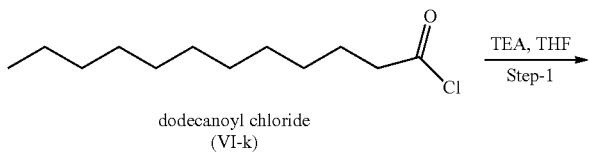
dodecanoyl chloride
(VI-k)
TEA, THF
———————→
Step-1
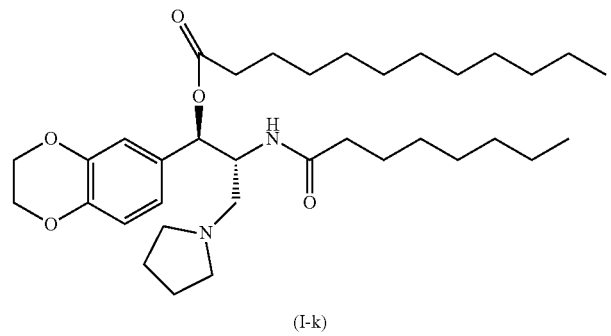
(I-k)
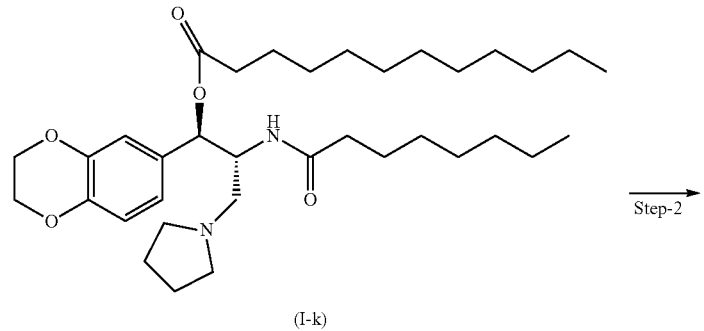
(I-k)
Step-2
————→
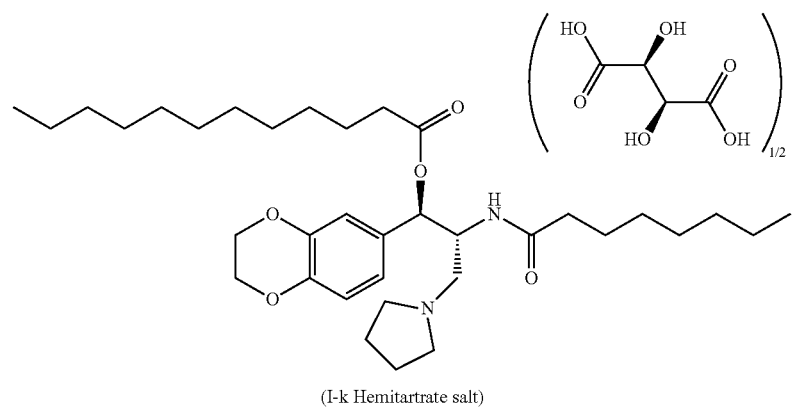
(I-k Hemitartrate salt)

Step-1: Preparation of Compound of Formula (I-k) ((1R,2R)-1-(2,3-dihydrobenzo[b][1,4]dioxin-6-yl)-2-octanamido-3-(pyrrolidin-1-yl)propyl dodecanoate)

Eliglustat (0.300 g) was dissolved in THF (6 ml) at room temperature under nitrogen atmosphere. TEA (0.186 g) was added and the reaction mass was cooled to 5-10° C. under nitrogen atmosphere. Dodecanoyl chloride (0.242 g) in THF (1 ml) was drop wise added at 5-10° C., within 5-10 min light orange colored suspension formed after completion of addition. The reaction mass was stirred at room temperature for 16-18 hrs. After completion of the reaction, the reaction mass was poured into water (20 ml) and product was extracted by dichloromethane (10 ml×2). The organic layer was separated, washed with saturated NaHCO$_3$ solution (10 ml×2). The organic layer was separated, dried over sodium sulphate and dried under vacuum at 40° C. for 30 minutes to afford the crude product. The crude product was purified by column chromatography using silica gel (100-200 mesh) with elution of 3-4% MeOH in dichloromethane to get pure product (0.250 g). Mass (m/z): 587.3 [M+H]. Yield: 57%

Step-2: Preparation of Hemitartrate Salt of Compound of Formula (I-k)

Step-1 product (I-k, free base) (0.15 g) was dissolved in Acetone (1.8 ml) at room temperature under nitrogen atmosphere. L (+) tartaric acid (0.019 g) was dissolved in Acetone (0.6 ml) and drop wise added to the reaction mass at room temperature under nitrogen atmosphere. The reaction mass was stirred at 40° C. for 2 hrs and at room temperature for overnight. The reaction mass was concentrated and product was triturated with n-pentane. The solvent was decanted, solid product was dried under vacuum to get pure product (0.10 g). $^1$H NMR (400 MHz, CDCl3) δ 7.075 (bs, 1H), 6.773-6.869 (m, 3H), 5.675-5.690 (d, 1H), 4.758 (bs, 1H), 4.291 (s, 5H), 3.727 (t, 1H), 2.265-2.654 (d, 1H), 2.28-2.42 (m, 5H), 1.9-2.2 (m, 7), 1.18-1.31 (m, 20H), 0.859-0.890 (m, 6H). Yield: 69%

Example-12: Preparation of Hydrochloride Salt Compound of Formula (I-l)

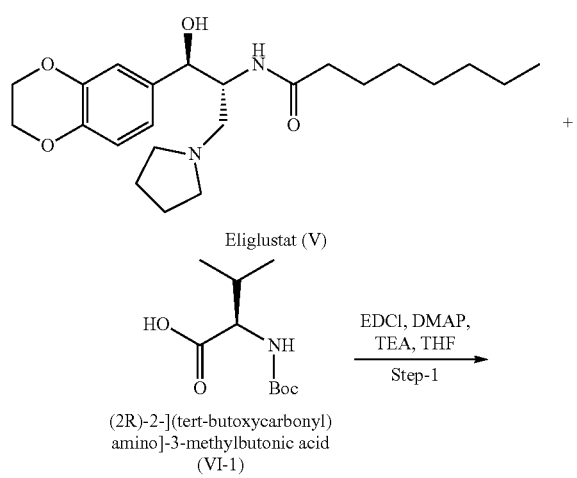

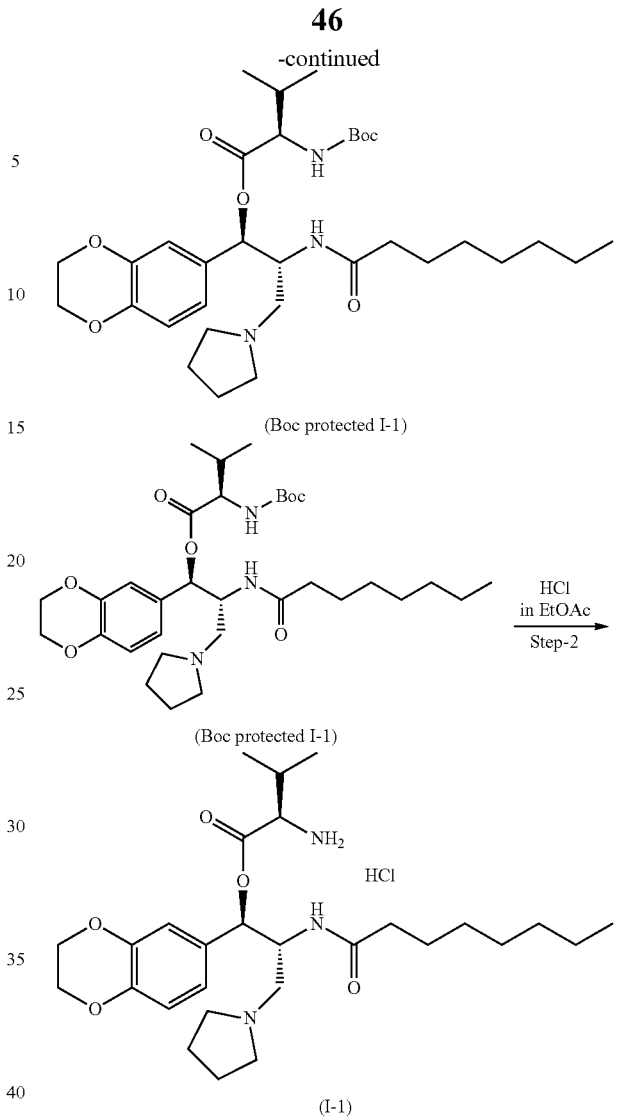

Step-1: Preparation of Boc-protected compound of formula (I-l) ((1R,2R)-1-(2,3-dihydrobenzo[b][1,4]dioxin-6-yl)-2-octanamido-3-(pyrrolidin-1-yl)propyl (tert-butoxycarbonyl)-D-valinate)

Eliglustate (0.400 g) was dissolved in THF (4 ml) at room temperature under nitrogen atmosphere. TEA (0.300 g) and DMAP (0.023 g) were added to the reaction mass at room temperature under nitrogen atmosphere. Boc-D-val-OH (0.640 g) and EDC.HCl (0.216 g) were added to the reaction mass to get off-white solid suspension. The reaction mass was stirred at room temperature for 16-18 hours under nitrogen atmosphere. After completion of the reaction, the reaction mass was poured into water (20 ml) and product was extracted by dichloromethane (10 ml×2). The organic layer was separated, washed with saturated NaHCO$_3$ solution (5 ml×2). The organic layer was separated, dried over sodium sulphate and dried under vacuum at 40° C. to afford the crude product. The crude product was purified by column chromatography using silica gel (100-200 mesh) with elution of 4-5% MeOH in dichloromethane to get pure product (0.350 g). Yield: 58%

Step-2: Preparation of Hydrochloride Salt of Compound of Formula (I-l)

Step-1 product (Boc-protected I-l) (0.150 g) was dissolved in Ethyl acetate (1.5 ml) at room temperature. 10% HCl in ethyl acetate (3 ml) was added to the reaction mass at 100 C. The reaction mass was stirred at room temperature for 3 hrs. After completion, the reaction mass was concentrated to get the residue. The residue was triturated with n-pentane (2 ml×3), solvent was decanted and solid was dried under vacuum to get the pure product as HCl salt (0.130 g). $^1$H NMR (400 MHz, DMSO-d6) δ 9.030 (bs, 2H), 8.141-8.438 (d, 1H), 6.856-6.921 (m, 2H), 6.757-6.778 (d, 1H), 5.815-5.822 (d, 1H), 4.466-4.514 (m, 1H), 4.204 (s, 4H), 3.838-3.851 (d, 1H), 3.417-3.519 (m, 4H), 3.088 (bs, 1H), 2.183-2.330 (m, 3H), 1.8-2.1 (bs, 4H), 1.3-1.43 (m, 11H), 0.968-0.985 (d, 3H), 0.844-0.900 (q, 6H). Yield: 97%

Example-13: Preparation of Hemitartrate Salt Compound of Formula (I-m)

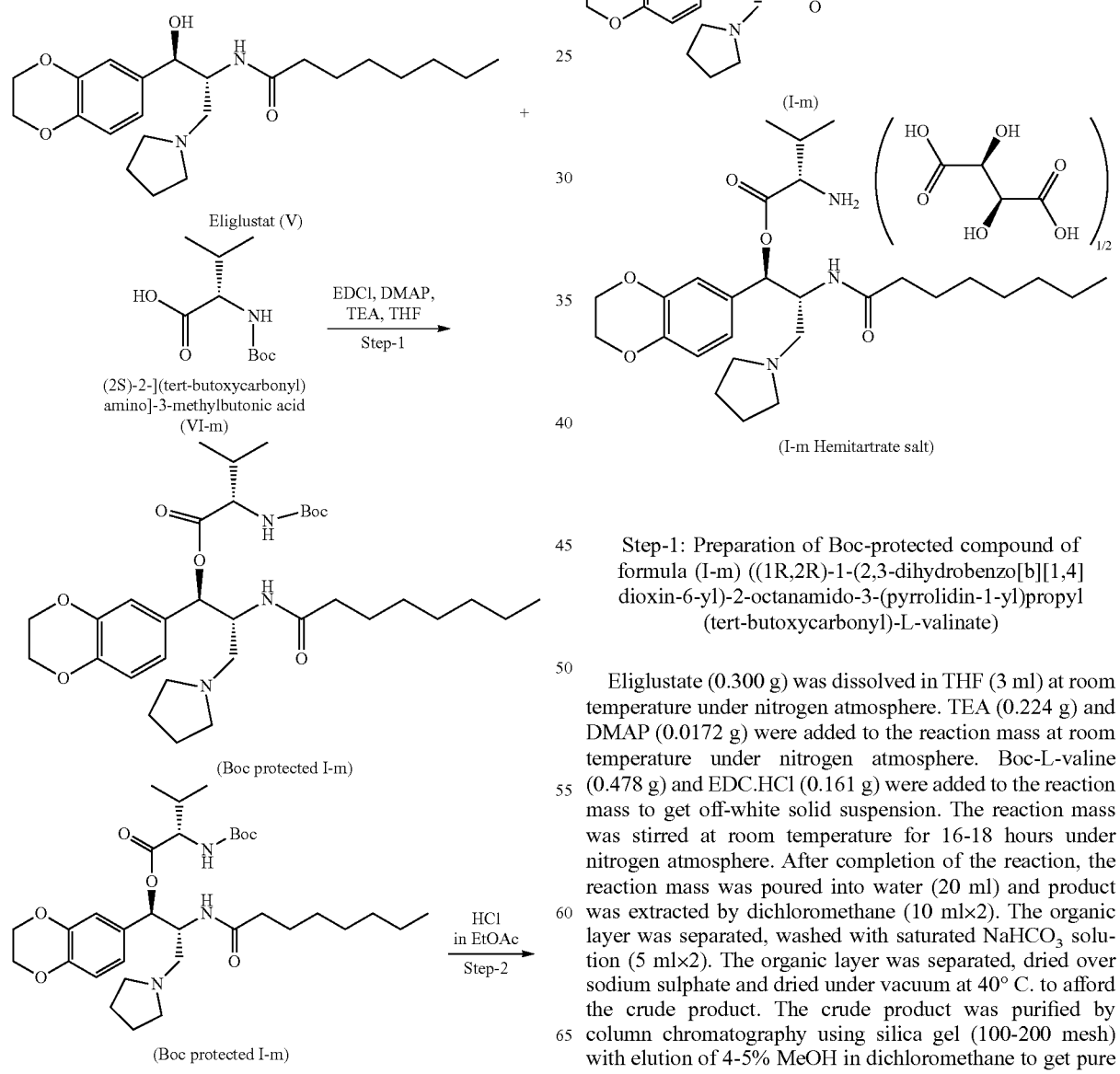

Step-1: Preparation of Boc-protected compound of formula (I-m) ((1R,2R)-1-(2,3-dihydrobenzo[b][1,4]dioxin-6-yl)-2-octanamido-3-(pyrrolidin-1-yl)propyl (tert-butoxycarbonyl)-L-valinate)

Eliglustate (0.300 g) was dissolved in THF (3 ml) at room temperature under nitrogen atmosphere. TEA (0.224 g) and DMAP (0.0172 g) were added to the reaction mass at room temperature under nitrogen atmosphere. Boc-L-valine (0.478 g) and EDC.HCl (0.161 g) were added to the reaction mass to get off-white solid suspension. The reaction mass was stirred at room temperature for 16-18 hours under nitrogen atmosphere. After completion of the reaction, the reaction mass was poured into water (20 ml) and product was extracted by dichloromethane (10 ml×2). The organic layer was separated, washed with saturated NaHCO₃ solution (5 ml×2). The organic layer was separated, dried over sodium sulphate and dried under vacuum at 40° C. to afford the crude product. The crude product was purified by column chromatography using silica gel (100-200 mesh) with elution of 4-5% MeOH in dichloromethane to get pure product (0.200 g). Yield: 44%

Step-2: Preparation of Compound of Formula (I-m)

Step-1 product (Boc-protected I-m) (0.200 g) was dissolved in Ethyl acetate (2 ml) at room temperature. 10% HCl in ethyl acetate (2 ml) was added to the reaction mass at 100 C. The reaction mass was stirred at room temperature for 3 hrs. After completion, the reaction mass was concentrated to get the residue. The residue was poured into saturated NaHCO₃ solution (10 ml) and product was extracted by dichloromethane (5 ml×2). The organic layer was separated, dried over sodium sulphate and dried under vacuum at 40° C. to afford the crude product. The product has been confirmed by mass (0.120 g). Mass (m/z): 504.2 [M+H]. Yield: 72%

Step-3: Preparation of Hemitartrate Salt of Compound of Formula (I-m)

Step-2 product (I-m, free base) (0.100 g) was dissolved in Acetonitrile (3 ml) at room temperature under nitrogen atmosphere. L (+) tartaric acid (0.015 g) was added to the reaction mass at room temperature under nitrogen atmosphere. The reaction mass was stirred at 40° C. for 2 hrs and at room temperature for overnight. The reaction mass was concentrated and product was triturated with n-pentane. The solvent was decanted, solid product was dried under vacuum to get pure product (0.092 g) ¹H NMR (400 MHz, DMSO-d6) δ 7.704 (bs, 1H), 6.764 (m, 3H), 4.1-4.4 (s, 4H), 4.071 (s, 3H), 2.066 (s, 4H), 1.711 (bs, 4H), 1.13-1.43 (m, 10H), 0.859 (bs, 9H). Yield: 80%

Example-14: Preparation of Hemitartrate Salt Compound of Formula (I-n)

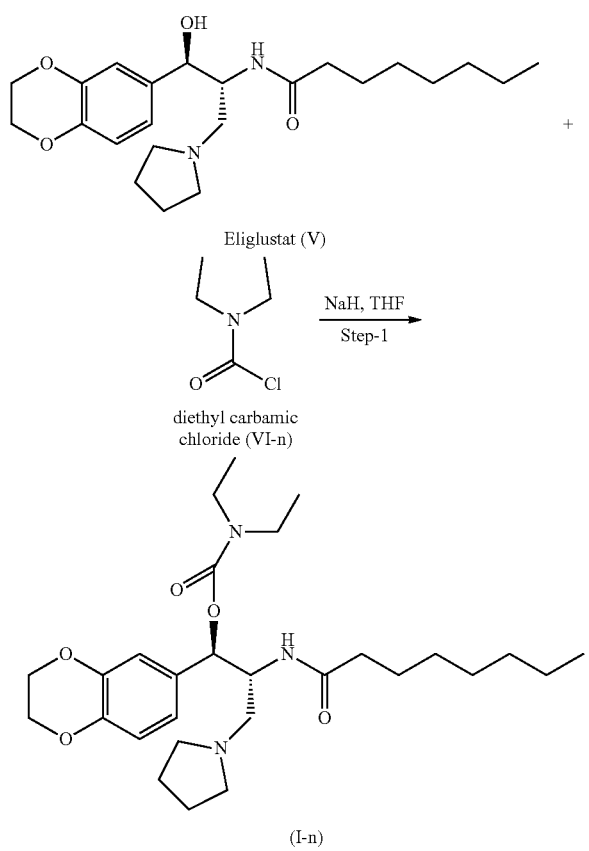

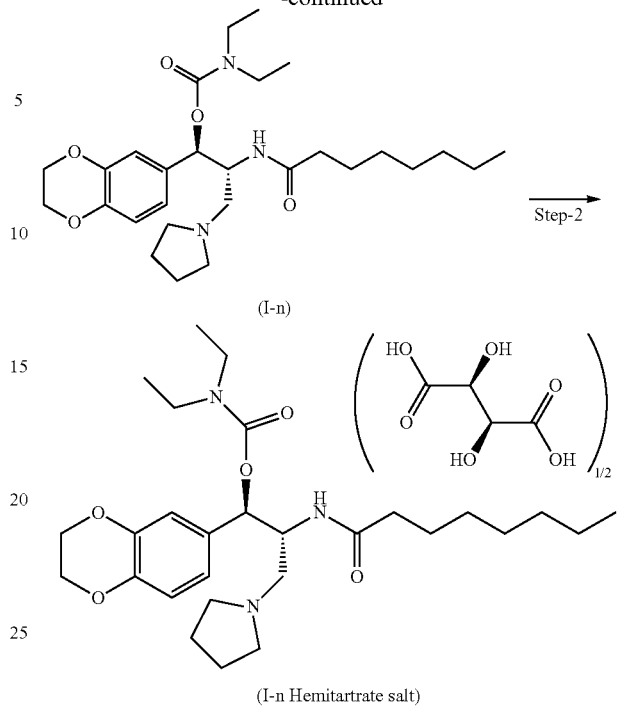

(I-n Hemitartrate salt)

Step-1: Preparation of Compound of Formula (I-n) ((1R,2R)-1-(2,3-dihydrobenzo[b][1,4]dioxin-6-yl)-2-octanamido-3-(pyrrolidin-1-yl)propyl diethylcarbamate)

Eliglustat (0.300 g) was dissolved into THF (10.5 ml) at room temperature under nitrogen atmosphere. The reaction mass was cooled to 5-10° C. under nitrogen atmosphere. NaH 55% (0.0388 g) was added to the reaction mass to get suspension and the reaction mass was stirred at 5-10° C. for 15-20 min. Diethyl carbamic chloride (0.120 g) in THF (1 ml) was drop wise added to the reaction mass and the reaction mass was stirred at room temperature for 16-18 hrs light grey colored suspension formed after completion of addition. completion of the reaction, the reaction mass was poured into water (20 ml) and product was extracted by dichloromethane (10 ml×2). The organic layer was separated, washed with saturated NaHCO₃ solution (5 ml×2). The organic layer was separated, dried over sodium sulphate and dried under vacuum at 40° C. to afford the crude product. The crude product was purified by column chromatography using silica gel (100-200 mesh) with elution of 4-5% MeOH in dichloromethane to get pure product (0.320 g). Mass (m/z): 504.3 [M+H]. Yield: 85%

Step-2: Preparation of Hemitartrate Salt of Compound of Formula (I-n)

Step-1 product (I-n, free base) (0.320 g) was dissolved in Acetone (3.7 ml) at room temperature under nitrogen atmosphere. L (+) tartaric acid (0.048 g) was dissolved in Acetone (1.5 ml) and drop wise added to the reaction mass at room temperature under nitrogen atmosphere. The reaction mass was stirred at 40° C. for 2 hrs and at room temperature for overnight. The reaction mass was concentrated and product was triturated with n-pentane. The solvent was decanted, solid product was dried under vacuum to get pure product (0.230 g). ¹H NMR (400 MHz, CDCl3) δ 7.351-7.376 (d, 1H), 6.800-6.852 (m, 3H), 5.600-5.618 (d, 1H), 4.750 (bs, 1H), 4.374 (s, 1H), 4.250 (s, 4H), 3.7-3.817 (m, 1H), 3.627-3.649 (t, 1H), 3.48-3.61 (m, 2H), 3.32-3.48 (m, 2H), 3.15-3.32 (m, 4H), 2.637-2.646 (d, 1H), 2.604-2.614 (d, 1H), 2.189-2.293 (m, 2H), 2.062 (bs, 4H), 1.48-1.58 (m, 2H), 1.18-1.32 (m, 10H), 1.131-1.166 (t, 3H), 1.073-1.107 (t, 3H), 0.853-0.883 (t, 3H).

Yield: 62%

Example-15: Preparation of Compound of Formula (I-o) (4-((1R,2R)-1-(2,3-dihydrobenzo[b][1,4]dioxin-6-yl)-2-octanamido-3-(pyrrolidin-1-yl)propoxy)-4-oxobutanoic acid)

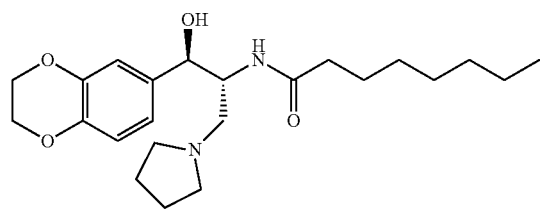

Eliglustat (V)

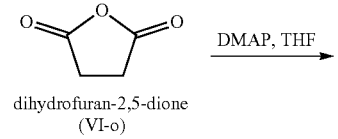

dihydrofuran-2,5-dione (VI-o)

DMAP, THF →

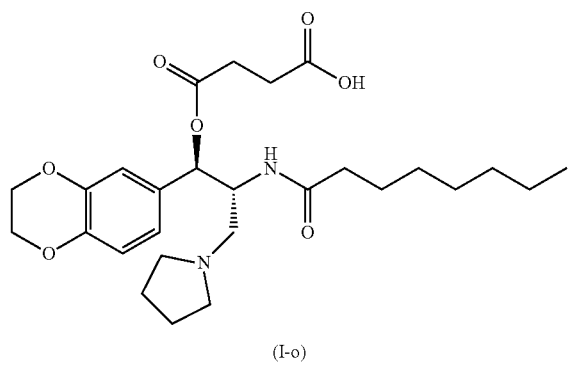

(I-o)

Eliglustat (0.250 g) was dissolved in THF (2.5 ml) at room temperature under nitrogen atmosphere. DMAP (0.0378 g) and dihydrofuran-2,5-dione (0.0927 g) were added and the reaction mass was stirred at 50° C. temperature for 2-3 hrs. After completion of the reaction, the reaction mass was poured into water (10 ml) and solid product was filtered and washed with water and dried under vacuum at 40° C. to afford the pure product (0.236 g). Mass (m/z): 505.3 [M+H]. ¹H NMR (400 MHz, DMSO-d6) δ 7.576-7.599 (d, 1H), 6.689-6.763 (m, 3H), 5.685-5.695 (d, 1H), 4.199 (s, 4H), 2.39-2.43 (m, 4H), 2.24-2.34 (m, 2H), 2.012-2.032 (t, 2H), 1.638 (bs, 4H), 1.135-1.481 (m, 10), 0.839-0.873 (t, 3H). Yield: 75%

Example-16: Preparation Hemitartrate Salt of Compound of Formula (I-p)

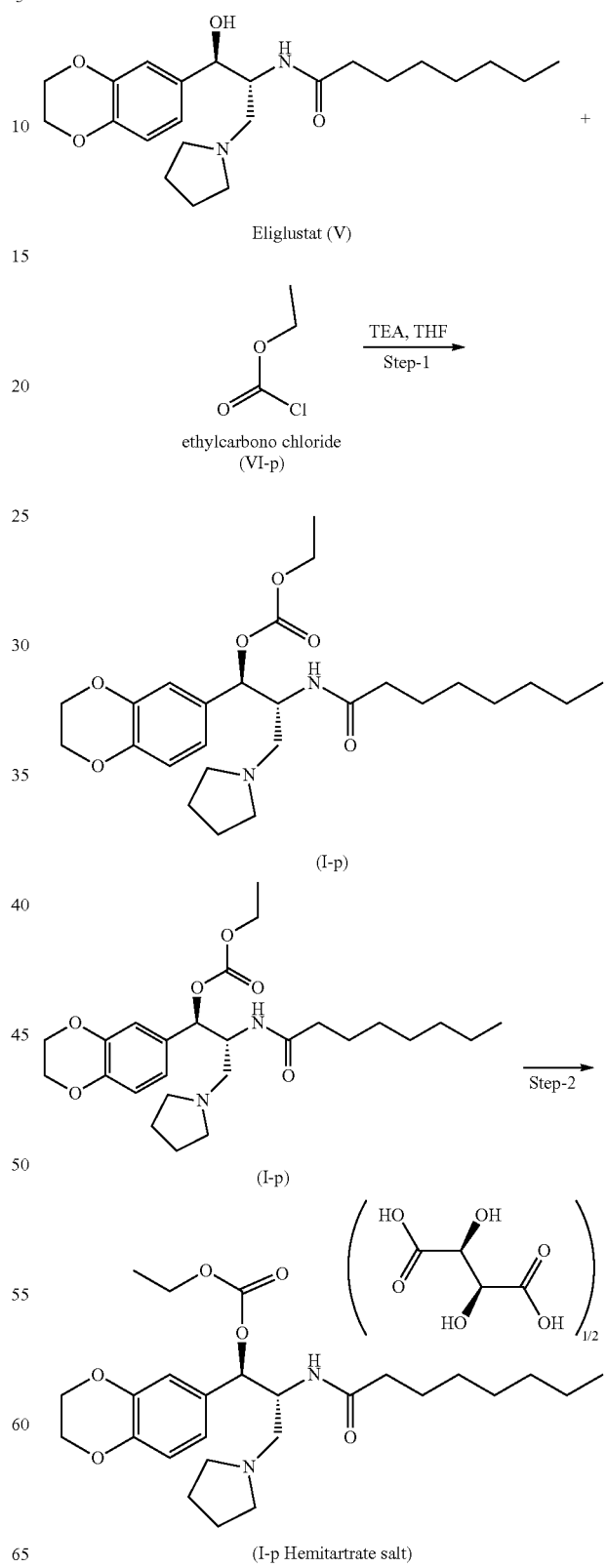

Step-1: Preparation of Compound of Formula (I-p) ((1R,2R)-1-(2,3-dihydrobenzo[b][1,4]dioxin-6-yl)-2-octanamido-3-(pyrrolidin-1-yl)propyl ethyl carbonate)

Eliglustat (0.300 g) was dissolved in THF (6 ml) at room temperature under nitrogen atmosphere. TEA (0.225 g) was added and the reaction mass was cooled to 5-10° C. under nitrogen atmosphere. Ethylcarbonochoride (0.120 g) in THF (1 ml) was drop wise added at 5-10° C., within 5-10 min light cream colored suspension formed after completion of addition. The reaction mass was stirred at room temperature for 16-18 hrs. After completion of the reaction, the reaction mass was poured into water (20 ml) and product was extracted by dichloromethane (10 ml×2). The organic layer was separated, washed with saturated NaHCO₃ solution (10 ml×2). The organic layer was separated, dried over sodium sulphate and dried under vacuum at 40° C. to afford the crude product. The crude product was purified by column chromatography using silica gel (100-200 mesh) with elution of 3-5% MeOH in dichloromethane to get pure product (0.080 g). Mass (m/z): 477.3 [M+H]. Yield: 22%

Step-2: Preparation of Hemitartrate Salt of Compound of Formula (I-p)

Step-1 product (I-p, free base) (0.072 g) was dissolved in Acetone (1 ml) at room temperature under nitrogen atmosphere. L (+) tartaric acid (0.011 g) was dissolved in Acetone (0.4 ml) and drop wise added to the reaction mass at room temperature under nitrogen atmosphere. The reaction mass was stirred at 40° C. for 2 hrs and at room temperature for overnight. The reaction mass was concentrated and product was triturate with n-pentane. The solvent was decanted, solid product was dried under vacuum to get pure product (0.067 g). ¹H NMR (400 MHz, DMSO-d6) δ 7.901-7.923 (d, 1H), 6.737-6.820 (m, 3H), 5.541-5.553 (d, 1H), 4.381 (bs, 1H), 4.215 (s, 5H), 4.065-4.117 (q, 2H), 2.853 (bs, 5H), 1.9-2.16 (m, 2H), 1.777 (bs, 4H), 1.09-1.41 (m, 10H), 0.843-0.878 (t, 3H). Yield: 80%

Example-17: Preparation of Compound of Formula (I-q)

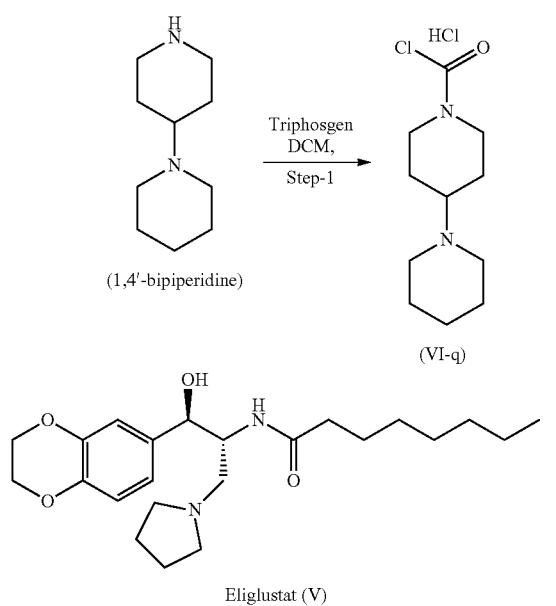

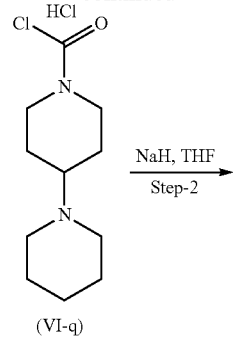

Step-1: Preparation of Compound of Formula (VI-q) ([1,4'-bipiperidine]-1'-carbonyl chloride hydrochloride)

Triphosgen (380 g) was dissolved into dichloromethane (4.86 ml) at room temperature for 30 minutes under nitrogen atmosphere. 4-piperidino piperidine-HCl (0.500 g) in dichloromethane (4.94 ml) was drop wise added at 5-10° C. within 30 minutes. The reaction mass was stirred at 5-10° C. for 2 hours and at 30° C. for 2 hours. After completion of the reaction, the reaction mass was dried under vacuum at 40° C. to afford the pure solid product (0.600 g). Yield: 87%

Step-2: Preparation of Compound of Formula (I-q) ((1R,2R)-1-(2,3-dihydrobenzo[b][1,4]dioxin-6-yl)-2-octanamido-3-(pyrrolidin-1-yl)propyl [1,4'-bipiperidine]-1'-carboxylate)

Eliglustat (0.200 g) was dissolved into THF (7 ml) at room temperature under nitrogen atmosphere. The reaction mass was cooled to 5-10° C. under nitrogen atmosphere. NaH (55%) (0.06 g) was added to the reaction mass to get suspension, the reaction mass was stirred at 5-10° C. for 15-20 min. Step-1 product (VI-q, 0.140 g) in THF (1 ml) was drop wise added to the reaction mass and stirred at room temperature for 16-18 hrs light yellow colored suspension formed after completion of addition. After completion of the reaction, the reaction mass was poured into water (10 ml) and product was extracted by dichloromethane (10 ml×2). The organic layer was separated, washed with saturated NaHCO₃ solution (10 ml×2). The organic layer was separated, dried over sodium sulphate and dried under vacuum at 40° C. to afford the crude product. The crude product was purified by column chromatography using silica gel (100-

200 mesh) with elution of 6-7% MeOH in dichloromethane to get pure product (0.080 g). Mass (m/z): 599.5 [M+H]. $^1$H NMR (400 MHz, DMSO-d6) δ 7.729 (bs, 1H), 6.701-6.795 (m, 3H), 5.497 (bs, 1H), 4.32 (bs, 1H), 4.206 (s, 4H), 3.991 (bs, 1H), 2.73-2.93 (bs, 3H), 2.043-2.077 (t, 2H), 1.83-1.91 (m, 2H), 1.59-1.8 (m, 8H), 1.31-1.54 (m, 6H), 1.15-1.31 (m, 10H), 0.843-0.877 (t, 3H). Yield: 27%

Example-18: Preparation of Compound of Formula (I-r) ((1R,2R)-1-(2,3-dihydrobenzo[b][1,4]dioxin-6-yl)-2-octanamido-3-(pyrrolidin-1-yl)propyl dimethylcarbamate)

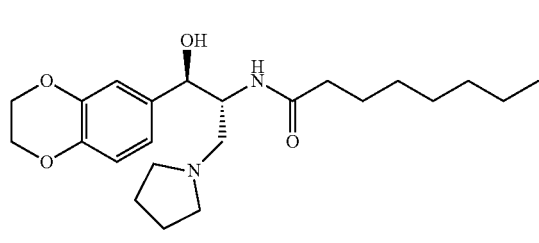

Eliglustat (V)

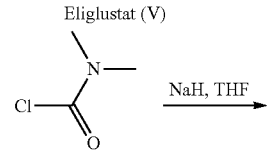

dimethylcarbamic chloride (VI-r)

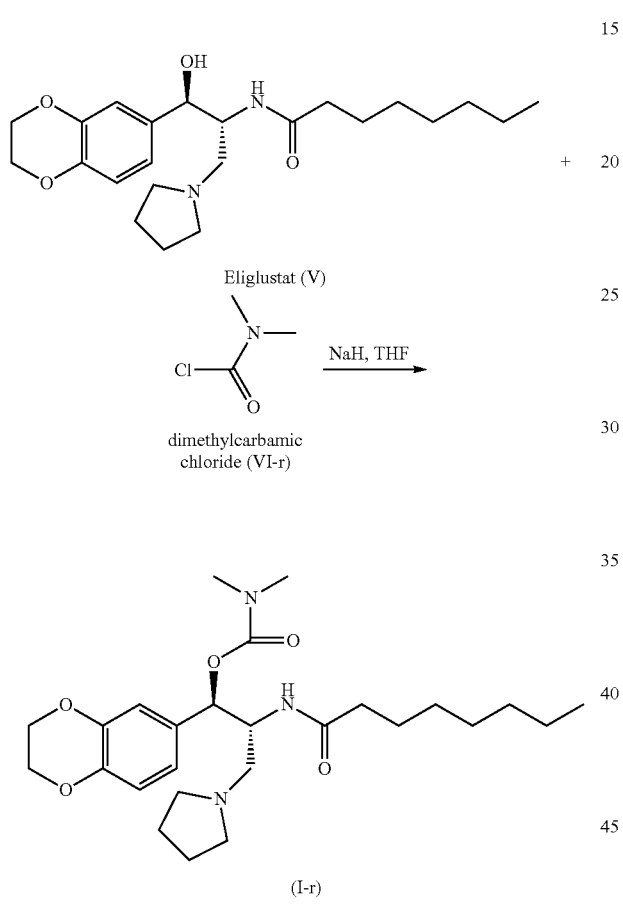

(I-r)

Eliglustat (0.200 g) was dissolved into THF (4 ml) at room temperature under nitrogen atmosphere. The reaction mass was cooled to 5-10° C. under nitrogen atmosphere. NaH (55%) (0.043 g) was added to the reaction mass to get suspension, the reaction mass was stirred at 5-10° C. for 15-20 min. Dimethyl carbamic chloride (0.100 g) in THF (1 ml) was drop wise added to the reaction mass and the reaction mass was stirred at room temperature for 16-18 hrs light grey colored suspension formed after completion of addition. After completion of the reaction, the reaction mass was poured into water (10 ml) and product was extracted by dichloromethane (10 ml×2). The organic layer was separated, washed with saturated NaHCO₃ solution (5 ml×2). The organic layer was separated, dried over sodium sulphate and dried under vacuum at 40° C. to afford the crude product. The crude product was purified by column chromatography using silica gel (100-200 mesh) with elution of 4-5% MeOH in dichloromethane to get pure product (0.115 g). $^1$H NMR (400 MHz, DMSO-d6) δ 9.933 (bs, 1H), 7.833-7.855 (d, 1H), 6.725-6.805 (m, 3H), 5.535-5.547 (d, 1H), 4.669-4.677 (d, 1H), 4.523 (bs, 1H), 4.208 (s, 4H), 3.36-3.5 (bs, 1H), 2.9-3.2 (m, 6H), 2.775 (bs, 2H), 2.689 (m, 1H), 2.092-2.129 (t, 2H), 1.865-1.932 (bs, 4H), 1.111-1.399 (m, 10H), 0.845-0.880 (t, 3H). Yield: 48%

Example-19: Preparation of Compound of Formula (I-s) ((E)-4-((1R,2R)-1-(2,3-dihydrobenzo[b][1,4]dioxin-6-yl)-2-octanamido-3-(pyrrolidin-1-yl)propoxy)-4-oxobut-2-enoic acid)

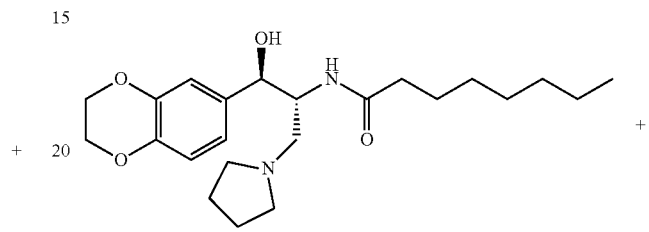

Eliglustat (V)

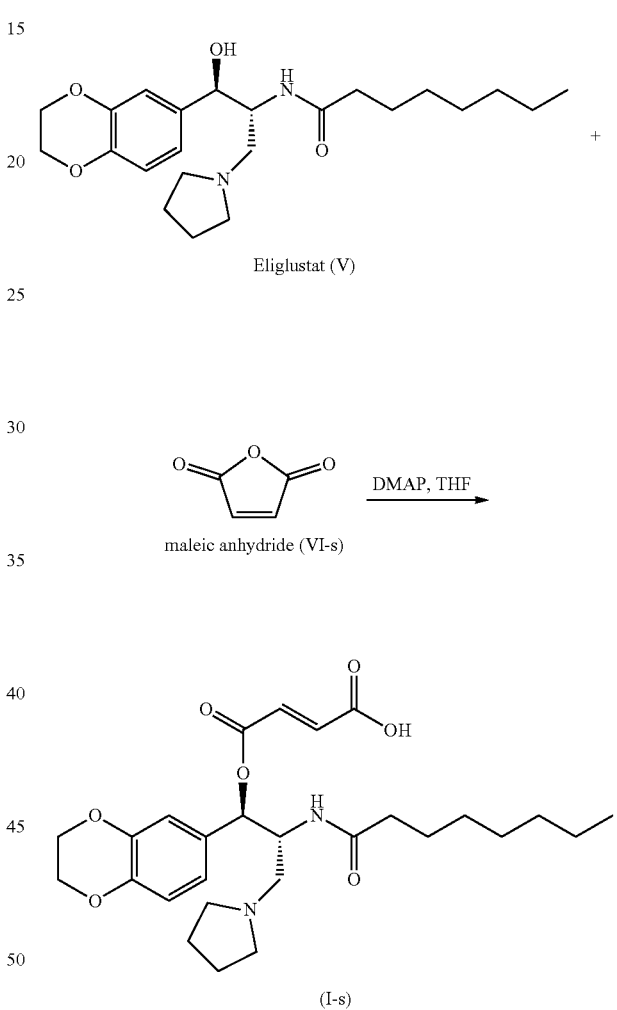

(I-s)

Eliglustat (0.200 g) was dissolved in THF (2.5 ml) at room temperature under nitrogen atmosphere. DMAP (0.0302 g) and maleic anhydride (0.0727 g) was added and the reaction mass was stirred at 50° C. temperature for 2-3 hrs. After completion of the reaction, the reaction mass was poured into water (10 ml) and solid product was filtered, washed with water and dried under vacuum at 40° C. to afford the pure product (0.135 g). Mass (m/z): 503.2 [M+H]. $^1$H NMR (400 MHz, DMSO-d6) 8.136-8.159 (d, 1H), 6.738-6.790 (t, 3H), 6.664-6.694 (d, 2H), 5.663 (d, 1H), 5.532-5.562 (d, 1H), 4.669-4.677 (d, 1H), 4.297 (bs, 1H), 4.195 (s, 4H), 2.8-3.2 (m, 6H), 1.990-2.164 (m, 2H), 1.785-1.854 (bs, 4H), 1.142-1.434 (m, 10H), 0.843-0.877 (t, 3H). Yield: 54%

Example-20: Preparation of Compound of Formula (I-t) (5-(((1R,2R)-1-(2,3-dihydrobenzo[b][1,4]dioxin-6-yl)-2-octanamido-3-(pyrrolidin-1-yl)propoxy)-5-oxopentanoic acid)

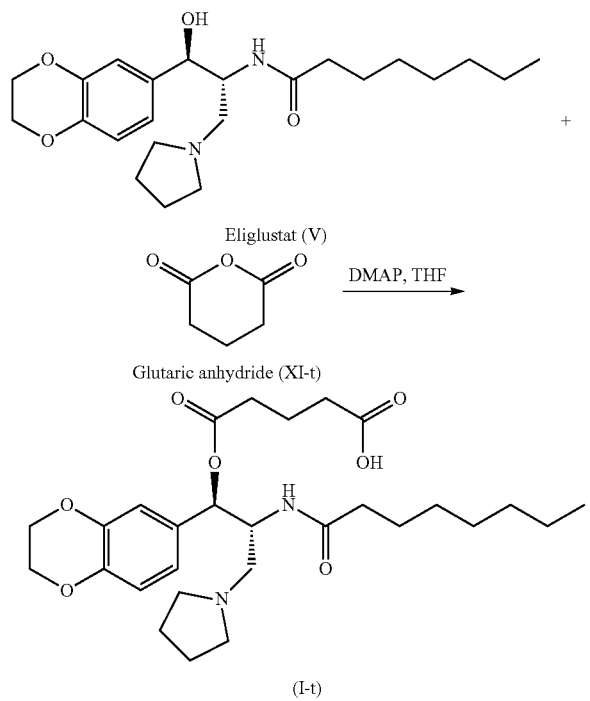

(I-t)

Eliglustat (0.200 g) was dissolved in THF (2.5) at room temperature under nitrogen atmosphere. DMAP (0.0302 g) and glutaric anhydride (0.084 g) were added and the reaction mass was stirred at 50° C. temperature for 2-3 hrs. After completion of the reaction, the reaction mass was poured into water (10 ml) and semi-solid product was filtered. Semi-solid product was dissolve in dichloromethane and concentrated under vacuum at 40° C. to afford the pure product as off white gum (0.100 g). Mass (m/z): 519.2 [M+H]. $^1$H NMR (400 MHz, DMSO-d6) δ 8.105 (s, 1H), 7.647-7.670 (d, 1H), 6.629-6.779 (m, 3H), 5.657-5.669 (d, 1H), 4.204 (s, 4H), 2.3-2.42 (m, 6H), 2.19-2.3 (m, 6H), 2.009-2.208 (m, 2H), 1.642-1.760 (m, 6H), 1.090-1.386 (m, 10H), 0.838-0.873 (t, 3H).

Yield: 39%

Example-21: Preparation of Hemitartrate Salt of Compound of Formula (I-u)

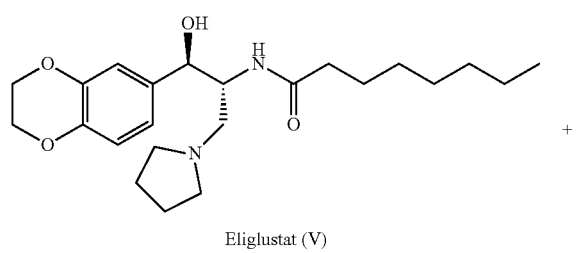

Eliglustat (V)

+

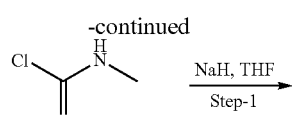

methylcarbamic chloride (VI-u)

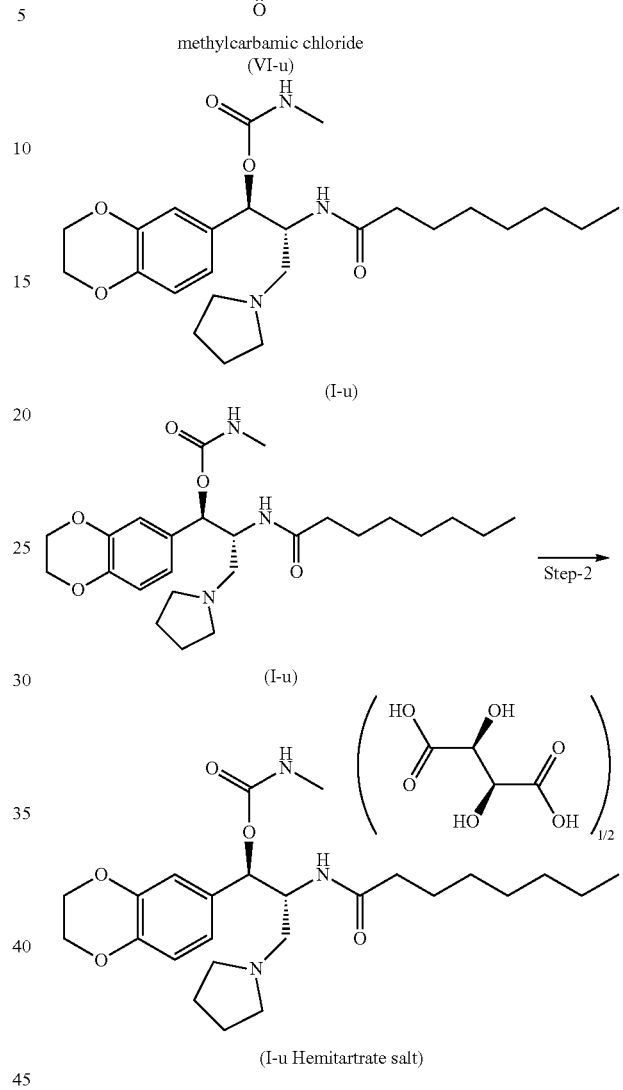

Step-1: Preparation of Compound of Formula (I-u) ((1R,2R)-1-(2,3-dihydrobenzo[b][1,4]dioxin-6-yl)-2-octanamido-3-(pyrrolidin-1-yl)propyl methylcarbamate)

Eliglustat (0.20 g) was dissolved into THF (3 ml) at room temperature under nitrogen atmosphere. The reaction mass was cooled to 5-10° C. and NaH (55%) (0.086 g) was added to the reaction mass suspension, the reaction mass was stirred at 5-10° C. for 15-20 min. methyl amino formayl chloride (0.096 g) in THF (1 ml) was drop wise added to the reaction mass and the reaction mass was stirred at room temperature for 16-18 hrs. After completion of the reaction, the reaction mass was poured into water (15 ml) and product was extracted by dichloromethane (10 ml×2). The organic layer was separated, washed with saturated NaHCO$_3$ solution (10 ml×2). The organic layer was separated, dried over sodium sulphate and dried under vacuum at 40° C. to afford the crude product. The crude product was purified by column chromatography using silica gel (100-200 mesh)

with elution of 4-5% MeOH in dichloromethane with 0.5% acetic acid to get pure product as acetic acid salt. The pure product was neutralized by saturated NaHCO₃ solution and product was extracted by dichloromethane. The solvent was concentrated to get the pure product as free base (0.055 g). Yield: 23%

Step-2: Preparation of Hemitartrate Salt of Compound of Formula (I-u)

Step-1 product (I-p, free base) (0.050 g) was dissolved in DCM (1 ml) at room temperature under nitrogen atmosphere. L (+) tartaric acid (0.008 g) was added to the reaction mass and add 3-4 drops of methanol to get clear solution at room temperature under nitrogen atmosphere. The reaction mass was stirred at 40° C. for 20 minutes. The reaction mass was concentrated and product was triturate with n-pentane. The solvent was decanted, solid product was dried under vacuum to get pure product (0.042 g). Yield: 72%

Example-22: Preparation of Compound of Formula (I-v) ((1R,2R)-1-(2,3-dihydrobenzo[b][1,4]dioxin-6-yl)-2-octanamido-3-(pyrrolidin-1-yl)propyl 2-nitrobenzoate)

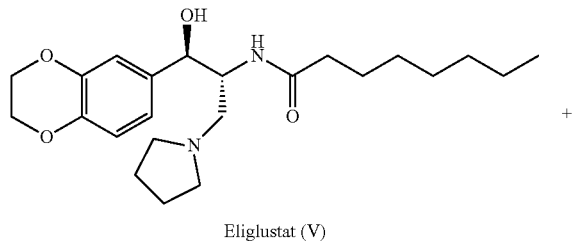

Eliglustat (V)

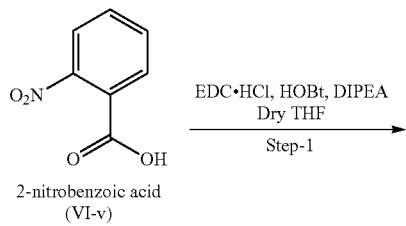

2-nitrobenzoic acid (VI-v)

EDC·HCl, HOBt, DIPEA
Dry THF
Step-1

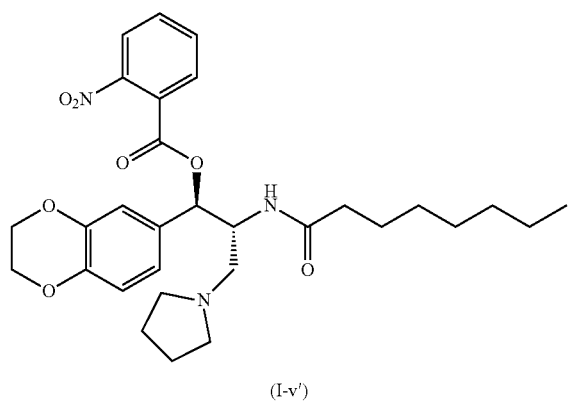

(I-v')

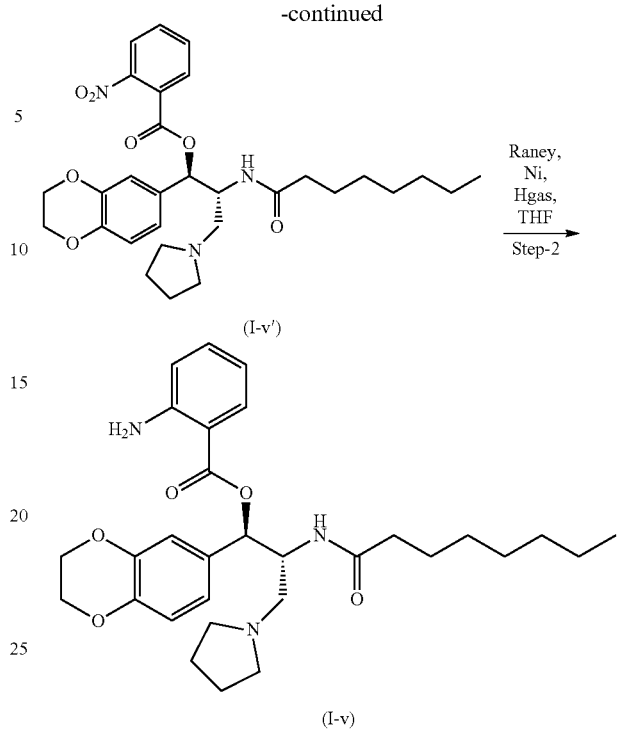

(I-v')

Raney, Ni, H gas, THF
Step-2

(I-v)

Step-1: Preparation of Compound of Formula (I-v') ((1R,2R)-1-(2,3-dihydrobenzo[b][1,4]dioxin-6-yl)-2-octanamido-3-(pyrrolidin-1-yl)propyl 2-nitrobenzoate)

To a stirred solution of 2-nitrobenzoic acid (0.18 g) in dry THF (4 ml) was added DIPEA (0.28 g), EDC.HCl (0.28 g) and HOBt (0.10 g) at 0° C. under nitrogen gas atmosphere. The reaction mixture was stirred for 1 h at 0° C. Eliglustat (0.30 g) was added at 0° C. The reaction mixture was stirred for 4 h at room temperature. After completion of reaction, the reaction mixture was diluted with 40 ml DM Water and the product was extracted in to Ethyl acetate (3×35 ml). The combined organic layer was dried over anhydrous sodium sulphate and organic layer was concentrated under reduced pressure to isolate the light yellow colored sticky liquid as crude product which was used directly in to next step. (0.45 g) Mass (m/z): 554.40 [M+H].

Step-2: Preparation of Compound of Formula (I-v) ((1R,2R)-1-(2,3-dihydrobenzo[b][1,4]dioxin-6-yl)-2-octanamido-3-(pyrrolidin-1-yl)propyl 2-aminobenzoate)

To a stirred solution of step-1 (I-v, free base) (0.40 g) in THF (10 ml) was added Raney nickel (0.080 g) at room temperature. The hydrogen gas was purged for 3 h. After completion of reaction, the reaction mixture was filtered off under vacuum filtration and solid was obtained. The preparative HPLC was performed in two mobile phases A) 5 mM ammonium bicarbonate+0.1% ammonia in water B) 100% acetonitrile. The product fraction was lyophilized to isolate the light brown colored solid as title compound. (0.039 g). Mass (m/z): 524.41 [M+H]. ¹H NMR (400 MHz, DMSO): δ 8.05 (d, 1H), 7.83 (d, 1H), 7.26 (t, 1H), 6.79 (s, 1H), 6.74 (d, 2H), 6.62-6.55 (m, 2H), 6.09 (s, 2H), 5.80 (d, 1H), 4.37 (d, 1H), 4.2 (s, 4H), 4.44-4.34 (m, 7H), 2.04 (t, 2H), 1.64 (s, 4H), 1.37 (d, 3H), 1.23-1.15 (m, 6H), 0.85 (t, 3H). Yield: 10%

Example-23: Preparation of Hemitartrate Salt of Compound of Formula (IV-b)

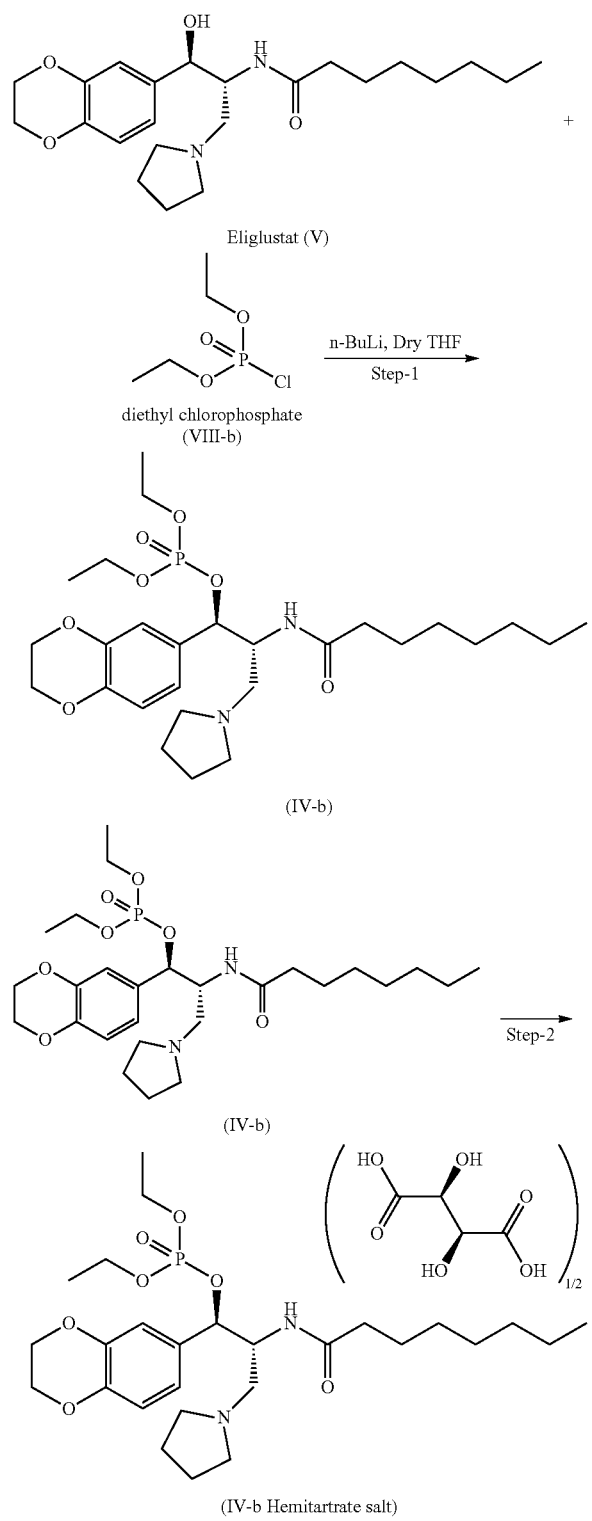

Step-1: Preparation of Compound of Formula (IV-b) ((1R,2R)-1-(2,3-dihydrobenzo[b][1,4]dioxin-6-yl)-2-octanamido-3-(pyrrolidin-1-yl)propyl diethyl phosphate)

To the −78° C. cooled stirred solution of Eliglustat (0.50 g) in Dry THF (5 ml), n-BuLi (0.74 ml) was added slowly drop wise under nitrogen gas atmosphere. The reaction mass was stirred at same temperature for 1 h. Diethyl chlorophosphate (0.28 g) was added slowly drop wise. The reaction mixture was stirred for 6 h at same temperature. After completion of the reaction, the reaction mixture was quenched with 0.5 ml DM Water. The preparative HPLC was performed in two mobile phases A) 5 mM ammonium bicarbonate+0.1% ammonia in water B) 100% acetonitrile. The product fraction was lyophilized to isolate the colorless to light brown colored liquid product as free base (0.45 g). Mass (m/z): 541.64 [M+H]. $^1$H NMR (400 MHz, DMSO): δ 7.731 (br s, 1H), 6.848-6.746 (m, 3H), 5.299-5.266 (q, 1H), 4.558-4.301 (s, 4H), 4.211 (s, 1H), 4.003-3.380 (m, 4H), 2.448 (br s, 4H), 2.310-2.274 (m, 1H), 2.061 (t, 2H), 1.673 (s, 4H), 1.441-1.349 (m, 1H), 1.283-1.210 (m, 12H), 1.097 (t, 3H), 0.753 (t, 3H). Yield: 67%

Step-2: Preparation of Hemitartrate Salt of Compound of Formula (IV-b)

To a stirred solution of step-1 (IV-b, free base) (0.025 g) in acetonitrile (1 ml) was added L(+) tartaric acid (0.0034 g). DM Water (0.5 ml) was added and sonicated for 2 min. The mixture was lyophilized to isolate off-white colored solid as title compound. (0.027 g). Mass (m/z): 541.64 [M+H]. $^1$H NMR (400 MHz, DMSO): δ 7.844 (d, 1H), 6.829-6.761 (m, 3H), 5.297-5.266 (q, 1H), 4.247-4.231 (s, 5H), 4.162 (s, 2H), 4.038-3.381 (m, 4H), 3.718 (t, 2H), 2.709 (br s, 4H), 2.079 (t, 2H), 1.752 (s, 4H), 1.403 (t, 3H), 1.286-1.095 (m, 14H), 0.876 (t, 3H). Yield: 95%

Example-24: Preparation of Compound of Formula (IV-c) ((1R,2R)-1-(2,3-dihydrobenzo[b][1,4]dioxin-6-yl)-2-octanamido-3-(pyrrolidin-1-yl)propyl sulfamate)

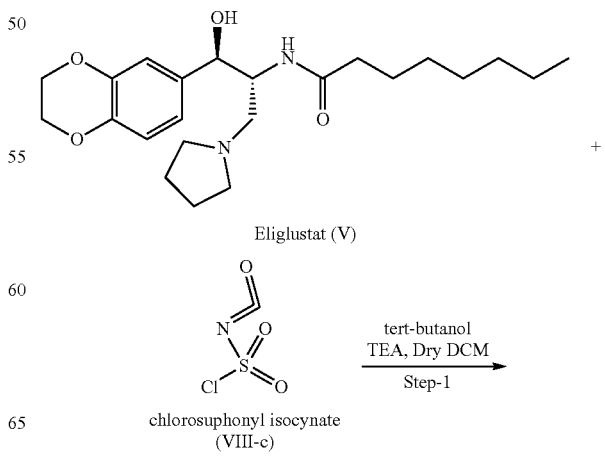

-continued

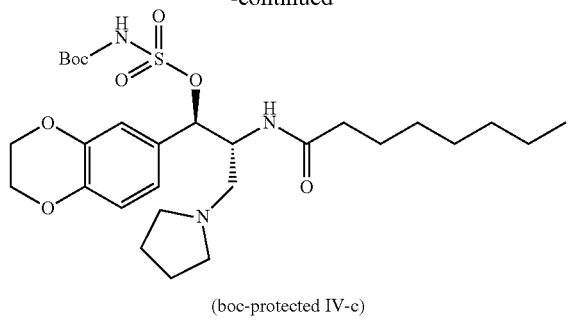

(boc-protected IV-c)

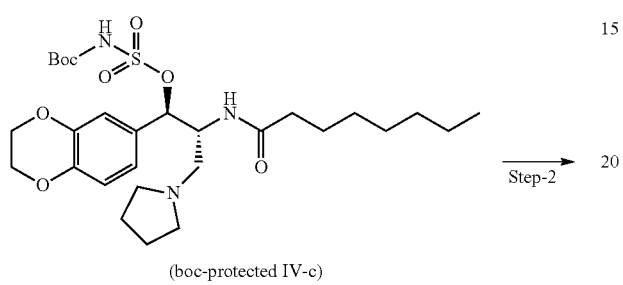

(boc-protected IV-c)

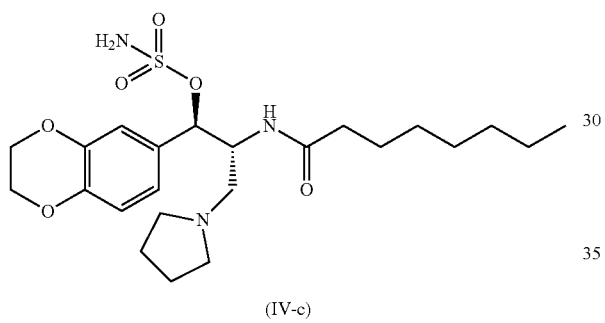

(IV-c)

Step-1: Preparation of Boc-Protected Compound of Formula (IV-c) ((1R,2R)-1-(2,3-dihydrobenzo[b][1,4]dioxin-6-yl)-2-octanamido-3-(pyrrolidin-1-yl)propyl (tert-butoxycarbonyl)sulfamate)

To the 0° C. cooled stirred solution of chlorosulphonyl isocynate (0.15 g) in Dry DCM (4 ml), tert-butanol (0.082 g) was added slowly drop wise under nitrogen gas atmosphere. The reaction mass was stirred at same temperature for 1 h till white colored solid precipitates out. Eliglustat (0.30 g) dissolved in to Dry dichlormethane (1 ml) was added slowly drop wise. The reaction mixture was stirred at 0° C. for 3 h. After completion of the reaction, the reaction mixture was concentrated under vacuum at 30° C. The preparative HPLC was performed in two mobile phases A) 5 mM ammonium bicarbonate+0.1% ammonia in water B) 100% acetonitrile. The product fraction was lyophilized to isolate the white colored solid (0.15 g). Mass (m/z): 584.71 [M+H]. Yield: 34%

Step-2: Preparation of Compound of Formula (IV-c)

To a stirred solution of step-1 (boc-protected compound, IV-c, 0.025 g) in dry dichloromethane (1.5 ml) was added 4M dioxane in HCl (0.25 ml). The reaction mixture was stirred at room temperature for 17 h. The reaction mixture was concentrated under reduced pressure to isolate the crude which was purified using preparative HPLC using two mobile phases A) 5 mM ammonium bicarbonate+0.1% ammonia in water B) 100% acetonitrile to obtain the title compound (0.040 g). Mass (m/z): 484.26 [M+H]. $^1$H NMR (400 MHz, DMSO): δ 6.796-6.757 (m, 3H), 6.627 (s, 2H), 6.434 (d, 1H), 5.753 (d, 1H), 4.222 (s, 4H), 3.601 (s, 1H), 2.386-2.328 (m, 6H), 1.661 (s, 4H), 1.542 (s, 2H), 1.236 (s, 10H), 0.855 (t, 3H). Yield: 40%

Example-25: Preparation of Compound of Formula (I-w) ((1R,2R)-1-(2,3-dihydrobenzo[b][1,4]dioxin-6-yl)-2-octanamido-3-(pyrrolidin-1-yl)propyl dimethylglycinate)

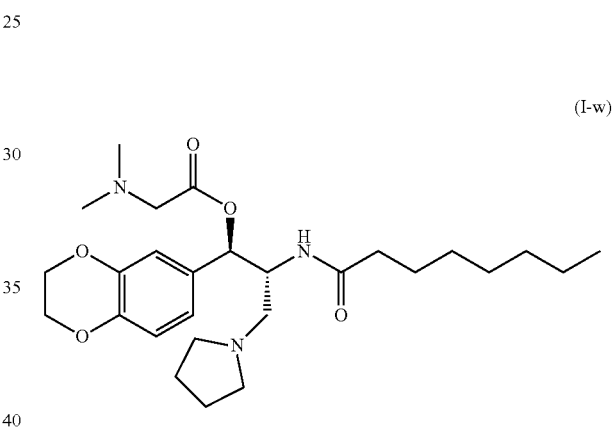

(I-w)

To a stirred solution of eliglustat (0.3 g) and dimethylglycine (0.11 g) in THF (4 mL) were added EDC.HCl (0.05 g) and HOBt (0.004 g) and stirred at 0° C. for 20 mins. Then N,N-diisopropylethylamine (DIPEA) (0.08 mL) was added drop wise to the reaction mixture and stirred at rt for 16 h. The reaction was monitored by TLC (mobile phase: 5% MeOH in DCM) and LCMS. After completion of reaction, the reaction mixture was evaporated in vacuum to obtain crude. The crude was purified by prep-HPLC purification using mobile phase A) 0.1% formic acid in Water B) 100% MeCN. The fractions were lyophilized to afford title compound.

Mass (m/z): 490.7 $^1$H NMR (400 MHz, DMSO): δ 7.56 (d, 1H), 6.72 (m, 3H), 5.28 (d, 1H), 5.10 (d, 1H), 4.73 (d, 1H), 4.19 (s, 4H), 4.04 (m, 1H), 2.58 (q, 1H), 2.42 (d, 4H), 2.22 (q, 1H), 2.01 (m, 2H), 1.66 (s, 4H), 1.37-1.10 (m, 10H), 1.03 (s, 9H), 0.86 (t, 3H).

Yield: 14.8%.

Example-26: Preparation of Compound of Formula I-x ((1R,2R)-1-(2,3-dihydrobenzo[b][1,4]dioxin-6-yl)-2-octanamido-3-(pyrrolidin-1-yl)propyl 3-morpholinopropanoate)

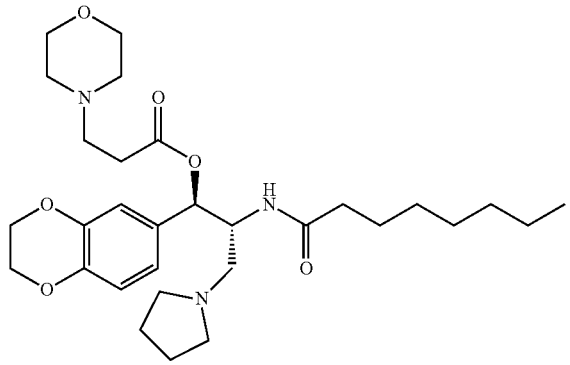

(I-x)

To a stirred solution of eliglustat (0.3 g) and 3-morpholinopropanoic acid (0.18 g) in THF (4 mL) were added EDC.HCl (0.05 g) and HOBt (0.004 g) and stirred at 0° C. for 20 mins. Then N,N-diisopropylethylamine (0.08 mL) was added drop wise to the reaction mixture and stirred at rt for 16 h. The reaction was monitored by TLC (mobile phase: 5% MeOH in DCM) and LCMS. After completion of reaction, the reaction mixture was evaporated in vacuum to obtain crude. The crude was purified by prep-HPLC purification using mobile phase A) 0.1% formic acid in Water B) 100% MeCN. The fractions were lyophilized to afford title compound (0.06 g) Mass (m/z): 546.7 $^1$H NMR (400 MHz, DMSO): δ 7.56 (d, 1H), 6.72 (m, 3H), 5.28 (d, 1H), 5.10 (d, 1H), 4.73 (d, 1H), 4.19 (s, 4H), 4.04 (m, 1H), 2.58 (q, 1H), 2.42 (d, 4H), 2.22 (q, 1H), 2.01 (m, 2H), 1.66 (s, 4H), 1.37-1.10 (m, 10H), 1.03 (s, 9H), 0.86 (t, 3H).

Yield: 14.8%.

Example-27: Preparation of Compound of Formula (I-y) ((1R,2R)-1-(2,3-dihydrobenzo[b][1,4]dioxin-6-yl)-2-octanamido-3-(pyrrolidin-1-yl)propyl pyrrolidine-1-carboxylate)

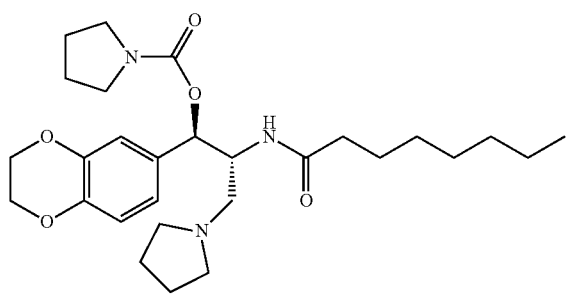

(I-y)

Step-1: Preparation of (1R,2R)-1-(2,3-dihydrobenzo[b][1,4]dioxin-6-yl)-2-octanamido-3-(pyrrolidin-1-yl)propyl (4-nitrophenyl) carbonate To a stirred solution of eliglustat (300 mg) in DCM (6 mL) were added 4-nitrophenyl carbonyl chloride (224.4 mg) and TEA (112.6 mg) at 0° C. and stirred for 2 h. The reaction was monitored by TLC (10% methanol & DCM) and LCMS. After completion of reaction, the reaction mixture was used for next step without workup.

Step-2: Preparation of Compound of Formula (I-y)

To solution of 1-methyl-1,4-diazepane 3 (37.6 mg) in DCM (3 mL) was added triethyamine (0.15 mL), followed by portion wise addition of prepared reaction mixture (step 1) at 0° C. and stirred at rt for 16 h. The reaction was monitored by TLC (10% Methanol in DCM) and LCMS. After completion of reaction the reaction, mixture was evaporated in vacuum to obtain crude. The crude was purified by prep-HPLC (purification method: A) 10 mM Ammonium Bicarbonate in water (B): 100% Acetonitrile. The fractions were lyophilized to afford (1R, 2R)-1-(2,3-dihydrobenzo[b] [1, 4] dioxin-6-yl)-2-octanamido-3-(pyrrolidin-1-yl) propyl pyrrolidine-1-carboxylate (72 mg, 19.18%, overall two steps) as an off white solid. Mass (m/z): 502.2 $^1$H NMR (400 MHz, DMSO): δ 7.51 (d, J=9.1 Hz, 1H), 6.77 (t, J=4.4 Hz, 1H), 6.70 (d, J=6.8 Hz, 2H), 5.47 (d, J=5.6 Hz, 1H), 4.20 (s, 5H), 3.40 (m, J=7.7 Hz, 2H), 3.19 (t, J=5.5 Hz, 2H), 2.36 (m, J=5.6 Hz, 6H), 2.03 (q, J=4.7 Hz, 2H), 1.78 (m, J=6.6 Hz, 4H), 1.62 (s, 4H), 1.40 (m, J=7.3 Hz, 2H), 1.22 (m, J=8.2 Hz, 8H), 0.86 (t, J=6.9 Hz, 3H).

Example-28: Preparation of Compound of Formula IV-d ((1R,2R)-1-(2,3-dihydrobenzo[b][1,4]dioxin-6-yl)-2-octanamido-3-(pyrrolidin-1-yl)propyl hydrogen sulfate)

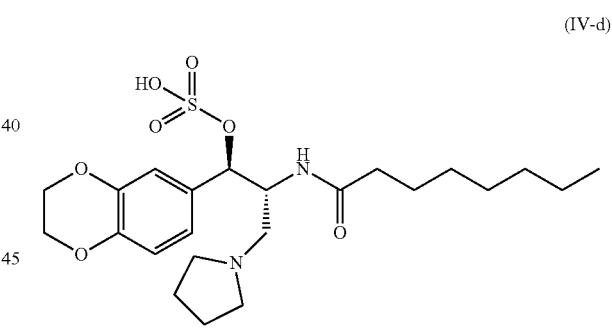

(IV-d)

To a stirred solution of eliglustat (0.10 g) in Dry THF (4 ml), n-BuLi (2.5M in n-hexane) (0.15 ml) was added slowly drop wise under nitrogen gas atmosphere. The reaction mixture was stirred for 30 min at −78° C. temperature. Pyridine-SO$_3$ complex (0.39 g) was added and the reaction was stirred at room temperature for 17 h. The reaction progress was monitored by LCMS and TLC. The reaction mixture was quenched with methanol to get clear solution and submitted to Prep HPLC for purification. The purification was by using mobile phase (A) 5 MM ammonium bicarbonate+0.1% formic acid in water (B) 100% MeCN. Product fraction was lyophilized to afford title compound (0.07 g) Mass (m/z): 483.25 $^1$H NMR (400 MHz, DMSO): δ 9.122 (s, 1H), 7.841 (d, 1H), 6.86 (d, 1H), 6.822-6.691 (m, 2H), 5.321 (d, 1H), 4.421 (s, 1H), 4.204 (s, 4H), 3.574 (s, 2H), 3.481 (s, 2H), 3.215-3.067 (s, 3H), 2.212-1.875 (m, 6H), 1.270-1.182 (m, 7H), 1.011 (d, 2H), 0.871 (t, 3H).

Yield: 58.4%.

Example-29: Preparation of Compound of Formula (II-a) ((1R,2R)-1-(2,3-dihydrobenzo[b][1,4]dioxin-6-yl)-2-octanamido-3-(pyrrolidin-1-yl)propyl 2-(2-(2-methoxyethoxy)ethoxy)acetate)

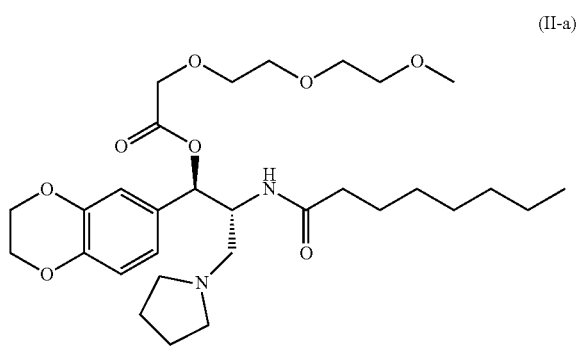 [SMILES: CCCCCCCC(=O)N[C@H](CN1CCCC1)[C@H](OC(=O)COCCOCCOC)c1ccc2c(c1)OCCO2]

(II-a)

To a stirred solution of 2-(2-(2-methoxyethoxy)ethoxy)acetic acid (0.26 g) in Dry THF (4 ml) was added DIPEA (0.51 g), EDC.HCl (0.38 g) and HOBt (0.030 g) at 0° C. under nitrogen gas atmosphere. The reaction mass was stirred for 30 min at 0° C. Eliglustat (0.40 g) was added at 0° C. The reaction was stirred for 4 h at room temperature. The reaction was monitored by TLC (mobile phase: 10% MeOH/DCM) and LCMS. After completion of reaction, the reaction mixture was diluted with 40 ml DM Water and the product was extracted in to Ethyl acetate (3×20 ml). The combined organic layer was dried over anhydrous sodium sulphate and organic layer was concentrated under reduced pressure to isolate the light yellow coloured sticky liquid as crude product which was purified by flash chromatography to elute product at 2.5% MeOH/DCM using combi-flash silica as title compound (0.04 g) Mass (m/z): 565.4 1H NMR (400 MHz, DMSO): δ 7.710 (t, 1H), 6.781 (dd, 3H), 5.801-5.722 (m, 1H), 4.211 (d, 5H), 3.631-3.482 (m, 5H), 3.432 (dd, 2H), 3.241 (s, 3H), 2.412 (s, 4H), 2.041 (d, 2H), 1.661 (s, 3H), 1.425-1.351 (m, 3H), 1.323-1.191 (m, 9H), 0.882 (t, 3H). Yield: 7.16%.

Example-30: Preparation of Compound of Formula (II-b) ((1R,2R)-1-(2,3-dihydrobenzo[b][1,4]dioxin-6-yl)-2-octanamido-3-(pyrrolidin-1-yl)propyl 3-(2-(2-aminoethoxy)ethoxy)propanoate)

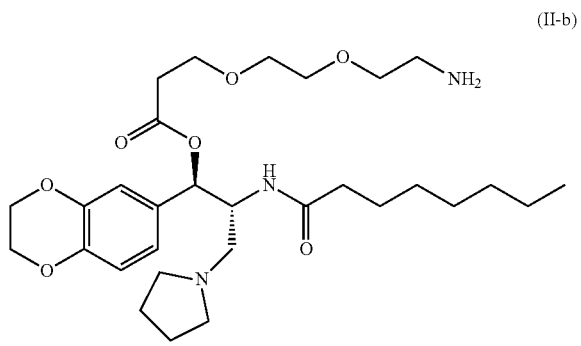 [SMILES: CCCCCCCC(=O)N[C@H](CN1CCCC1)[C@H](OC(=O)CCOCCOCCN)c1ccc2c(c1)OCCO2]

(II-b)

To a stirred solution of 2,2-dimethyl-4-oxo-3,8,11-trioxa-5-azatetradecan-14-oic acid (0.21 g) in Dry DCM (4 ml) was added eliglustat (0.28 g), and DMAP (0.017 g). The reaction mixture was stirred for 5 min. DCC (0.21 g) was added in to reaction mixture at room temperature. The reaction was stirred for 2 h at room temperature. The reaction was monitored by TLC (mobile phase: 10% MeOH/DCM) and LCMS. After completion of reaction, the reaction mixture was filtered off under vacuum filtration to remove solid DCU. The filtrate ML was concentrated under reduced pressure to isolate the sticky oily mass which was purified by flash chromatography using combi-flash silica to elute product at 4.5% MeOH/DCM as title compound (AN01027 Int-27) Mass (m/z): 564.82 1H NMR (400 MHz, DMSO): δ 7.656 (d, 1H), 6.792-6.715 (m, 3H), 5.714 (d, 1H), 4.214 (s, 5H), 3.681 (t, 3H), 3.465 (s, 4H), 3.065 (m, 2H), 2.600 (t, 2H), 2.412 (s, 4H), 2.042 (q, 2H), 1.815-1.516 (m, 5H), 1.383 (s, 9H), 0.871 (s, 3H).

Yield: Quantitative yield

Example-31: Preparation of Compound of Formula I-z (3-(((1R,2R)-1-(2,3-dihydrobenzo[b][1,4]dioxin-6-yl)-2-octanamido-3-(pyrrolidin-1-yl)propoxy)-3-oxopropanoic acid)

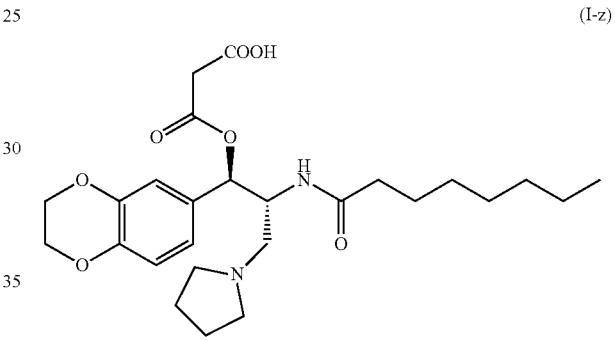

(I-z)

Step-1: Preparation of 3-(tert-butoxy)-3-oxopropanoic acid

To a stirred solution of malonic acid (0.50 g) in Dry THF (3 ml), Pyridine (1 ml) and tert-butanol (0.64 g) was added at 0° C. under nitrogen gas atmosphere. Mesyl chloride (0.55 g) was added in to reaction mixture at room temperature. The reaction was stirred for 2 h at room temperature. The reaction was monitored by TLC (mobile phase: 5.0% MeOH/DCM) and LCMS. After completion of reaction, the reaction mixture was filtered off under vacuum filtration and the filtrate ML was diluted with 15 ml chilled DM Water and then basified with 4N NaOH solution up to 11 pH. The aqueous layer was washed with DCM (2×10 ml). The aqueous layer was acidified with 33% HCl solution in water. The product was extracted in to DCM (3×20 ml). The combined organic layer was washed with brine solution (2×15 ml) and then dried over anhydrous sodium sulphate and then it was concentrated under reduced pressure below 35° C. to isolate the crude 3-(tert-butoxy)-3-oxopropanoic acid (Int-A) (0.40 g, 51.98%)

Step-2: Preparation of tert-butyl ((1R,2R)-1-(2,3-dihydrobenzo[b][1,4]dioxin-6-yl)-2-octanamido-3-(pyrrolidin-1-yl)propyl) malonate To a stirred solution of eliglustat (0.40 g) in Dry DCM (8 ml), DMAP (0.024 g) was added. The reaction mixture was stirred for 5 min at 0° C. DCC (0.30 g) was added slowly lot wise. The reaction was stirred at room temperature for 3 h. The reaction progress was monitored by TLC. After completion of the reaction, the reaction mixture was filtered off under vacuum filtration to remove DCU. The filtrate ML was concentrated under reduced pressure at 40° C. to isolate the crude which was purified by flash chromatography using combi-flash silica as mobile phase 3.5% MeOH/DCM to give a title compound (0.48 g, 88.80%)

Step-3: Preparation of 3-((1R,2R)-1-(2,3-dihydrobenzo[b][1,4]dioxin-6-yl)-2-octanamido-3-(pyrrolidin-1-yl)propoxy)-3-oxopropanoic acid To a stirred solution of tert-butyl ((1R,2R)-1-(2,3-dihydrobenzo[b][1,4]dioxin-6-yl)-2-octanamido-3-(pyrrolidin-1-yl)propyl) malonate (Int-39) (0.18 g) in Dry DCM (5 ml), Trifluoroacetic acid (0.37 g) was added. The reaction was stirred at room temperature for 17 h. The reaction progress was monitored by TLC and LCMS. The reaction mixture was concentrated under reduced pressure to isolate the crude which was submitted to prep. HPLC. The prep. HPLC was performed in to mobile phase A) 0.1% formic acid in water B) 100% ACN. The fraction was lyophilized to isolate title compound. Mass (m/z): 491.51 1H NMR (400 MHz, DMSO): δ 7.731 (d, 1H), 6.806-6.755 (m, 3H), 5.759 (d, 1H), 4.205 (d, 5H), 3.391-3.262 (m, 2H), 2.743-2.508 (s, 8H), 2.043 (d, 2H), 1.696 (d, 2H), 1.381 (t, 2H), 1.267-1.217 (m, 8H), 1.131 (s, 2H), 0.861 (t, 2H).

Yield: 35%

Example-32: Preparation of Compound of Formula I-Aa ((1R,2R)-1-(2,3-dihydrobenzo[b][1,4]dioxin-6-yl)-2-octanamido-3-(pyrrolidin-1-yl)propyl hexanoate)

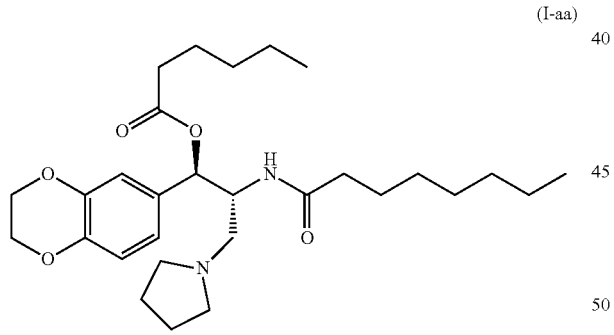

(I-aa)

Step-1: Preparation of (1R,2R)-1-(2,3-dihydrobenzo[b][1,4]dioxin-6-yl)-2-octanamido-3-(pyrrolidin-1-yl)propyl hexanoate Eliglustat (0.300 g) was dissolved in THF (6 ml) at room temperature under nitrogen atmosphere. Triethylamine (0.186 g) was added and the reaction mass was cooled to 5-100 C under nitrogen atmosphere. Hexanoyl chloride (0.149 g) in THF (1 ml) was drop wise added at 5-100 C within 5-10 min light off-white coloured suspension formed after completion of addition. The reaction mass was stirred at room temperature for 16-18 hrs. The reaction progress was checked by TLC. (TLC Mobile phase: 5% Methanol in DCM with ammonia atmosphere). After completion of the reaction, the reaction mass was poured into water (15 ml) and product was extracted by DCM (10 ml×2). The organic layer was separated, washed with saturated NaHCO$_3$ solution (10 ml×2). The organic layer was separated, dried over sodium sulphate and dried under vacuum at 40° C. for 30 minutes to afford the crude product. The crude product was purified by column chromatography using silica gel (100-200 mesh) with elution of 3-4% MeOH in MDC to get pure product. The product has been confirmed by mass.

Practical weight: –0.250 g
% of yield: –67.20%

Step-2: Preparation of rac-(1R,2R)-1-(2,3-dihydrobenzo[b][1,4]dioxin-6-yl)-2-octanamido-3-(pyrrolidin-1-yl)propyl hexanoate Step-1 product (rac-(1R,2R)-1-(2,3-dihydrobenzo[b][1,4]dioxin-6-yl)-2-octanamido-3-(pyrrolidin-1-yl)propyl hexanoate) (0.180 g) was dissolved in Acetone (2.4 ml.) at room temperature under nitrogen atmosphere. L (+) Tartaric acid (0.026 g) was dissolved in Acetone (0.9 ml, 32 vol.) was drop wise added to the reaction mass at room temperature under nitrogen atmosphere. The reaction mass was stirred at 400 C for 2 h. and at room temperature for overnight. The reaction mass was concentrated and product was triturate with n-pentane. The solvent was decanted; solid product was dried under vacuum to get title compound.

Practical weight: –0.160 g
% of yield: –77.66% Mass (m/z): 502.34 1H NMR (400 MHz, CDCl$_3$): δ 8.676 (bs, 1H), 7.521 (bs, 1H), 6.868-6.828 (d, 3H), 5.742-5.726 (d, 1H), 4.779 (bs, 1H), 4.237 (s, 4H), 4.030-4.088 (t, 1H), 3.922 (bs, 1H), 2.7-3.0 (m, 3H), 2.35-2.5 (m, 4H), 1.95-2.3 (bs, 8H), 1.5-1.47 (m, 4H), 1.11-1.4 (m, 10H), 0.822-0.872 (m, 6H).

Example-33: Preparation of Compound of Formula IX-a ((1R,2R)-1-(2,3-dihydrobenzo[b][1,4]dioxin-6-yl)-2-octanamido-3-(pyrrolidin-1-yl)propoxy)methyl pivalate)

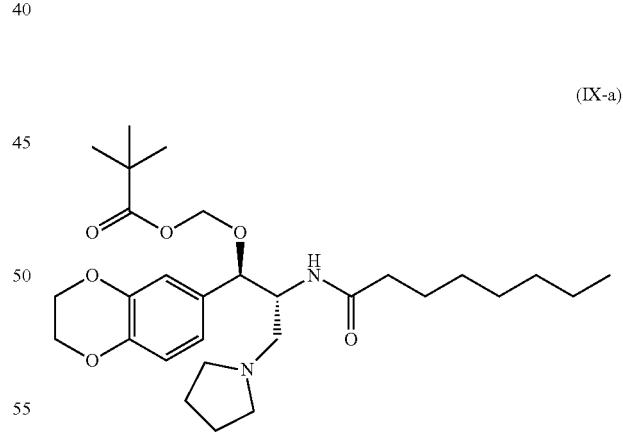

(IX-a)

To a stirred solution of N-((1R, 2R)-1-(2,3-dihydrobenzo[b][1,4]dioxin-6-yl)-1-hydroxy-3-(pyrrolidin-1-yl) propan-2-yl) octanamide (500 mg) in THF was added sodium hydride (74 mg) at 0° C. and stirred for 10 min. Chloromethyl pivalate (222 mg) was added to reaction mixture at 0° C. The resulting reaction mixture was stirred at rt for 24 h. The reaction was monitored by TLC (mobile phase: 100% EtOAc) and LCMS. Reaction mass was poured in to ice cold water and extracted by ethyl acetae (2×20 mL). Combined organic layers were washed with saturated brine solution (10 mL), dried over Na$_2$SO$_4$ and evaporated in vacuum to obtain crude. The reaction mixture was concentrated under reduced pressure to isolate the crude which was purified using preparative HPLC using two mobile phases A) 5 mM ammonium bicarbonate B) 100% acetonitrile to obtain the title compound (0.050 g) Mass (m/z): 519.2 $^1$H NMR (400 MHz, DMSO): δ 7.56 (d, 1H), 6.72 (m, 3H), 5.28 (d, 1H), 5.10 (d, 1H), 4.73 (d, 1H), 4.19 (s, 4H), 4.04 (m, 1H), 2.58 (q, 1H), 2.42 (d, 4H), 2.22 (q, 1H), 2.01 (m, 2H), 1.66 (s, 4H), 1.37-1.10 (m, 10H), 1.03 (s, 9H), 0.86 (t, 3H).

Yield: 8%.

Example-34: Metabolic Stability of Prodrugs in Human Liver Microsomes

Stock solution of the test compounds was prepared in DMSO and incubated in presence of Human Liver microsomes, Nicotinamide adenine dinucleotide phosphate (NADPH) and Dulbecco's phosphate-buffered saline (DPBS), pH-7.4 at different time point. At each time point, samples were withdrawn, and reactions were stopped using chilled acetonitrile or methanol containing suitable internal standard. The samples were centrifuged, and the supernatants were analysed in duplicate by LC-MS/MS. The percent compound remaining at each time point was calculated with respect to that of the first time point of the reaction. The data are then analysed to calculate half-life and intrinsic clearance (CLint) using following formula.

Half-life (t½) (min)=0.693/K, where k=Elimination rate constant

Intrinsic clearance (CL$_{int}$) (μL/min/mg protein)=[Volume of incubation (μL)/protein in the incubation (mg)× 0.693]/t$_{1/2}$.

| Sr No | Compound of formula | HLM stability (half-life, minutes) |
|---|---|---|
| 1 | Eliglustat | 30 |
| 2 | I-a Hemitartrate salt | <30 |
| 3 | I-b Hemitartrate salt | <30 |
| 4 | I-c Hemitartrate salt | <30 |
| 5 | I-d Hemitartrate salt | <30 |
| 6 | I-e Hemitartrate salt | <30 |
| 7 | I-f Hemitartrate salt | <30 |
| 8 | I-g Hemitartrate salt | <30 |
| 9 | I-h Hemitartrate salt | <30 |
| 10 | I-i Hemitartrate salt | <30 |
| 11 | I-j Hemitartrate salt | 63 |
| 12 | I-k Hemitartrate salt | 70 |
| 13 | I-l Hydrochloride salt | <30 |
| 14 | I-m Hemitartrate salt | <30 |
| 15 | I-n Hemitartrate salt | <30 |
| 16 | I-o | >90 |
| 17 | I-p Hemitartrate salt | <30 |
| 18 | I-q | <30 |
| 19 | I-r | <30 |
| 20 | I-s | 64 |
| 21 | I-t | 65 |
| 22 | I-u Hemitartrate salt | <30 |
| 23 | I-v | <30 |
| 24 | IV-b Hemitartrate salt | <30 |
| 25 | IV-c | <30 |
| 26 | I-w | <30 |
| 27 | I-x | <30 |
| 28 | I-y | ND |
| 29 | IV-d | >90 |
| 30 | II-a | <30 |
| 31 | II-b | >90 |
| 32 | I-z | >90 |
| 33 | I-aa | <30 |
| 34 | IX-a | ND |

We claim:

1. A compound of formula A:

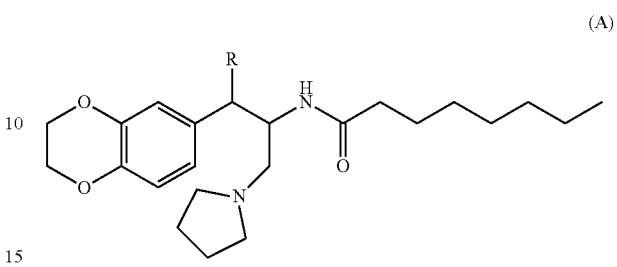

(A)

the geometric isomer, enantiomers, diastereomers, racemates, pharmaceutically acceptable salts or solvates thereof, wherein R is selected from group consisting of:

a)

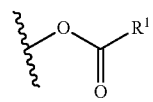

wherein, R$^1$ is selected from group consisting of optionally substituted aryl, optionally substituted heteroaryl, optionally substituted cycloalkyl, cycloheteroalkyl, amine, alkoxy, carboxylic acid, alkyl substituted with cycloheteroalkyl; alkyl substituted amine, alkyl substituted carboxylic acid, alkene substituted carboxylic acid;

b)

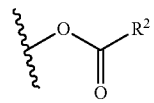

wherein, R$^2$ is

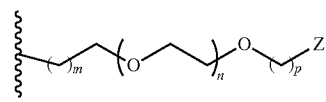

or

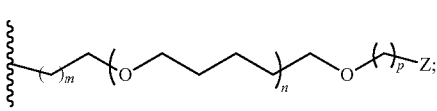

wherein m and p are independently selected from 0 to 3, n is selected from less than 10, about 50, about 100, about 150 or about 200 and Z is alkyl or amine;

c) R³ wherein, R³ is selected from group consisting of boron species;

d)

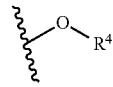

wherein, R⁴ is selected from group consisting of alkyl substituted with cycloheteroalkyl, optionally substituted with phosphoryl, alkyl substituted phosphoryl, sulfuryl, sulfonamide; and e)

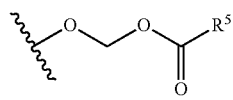

wherein, R⁵ is selected from group consisting of optionally substituted aryl, optionally substituted heteroaryl, optionally substituted cycloalkyl, cycloheteroalkyl, alkyl, amine, alkoxy, carboxylic acid, alkyl substituted with cycloheteroalkyl, alkyl substituted amine.

2. The compound of formula A according to claim 1, which is represented by the following formula I:

(I)

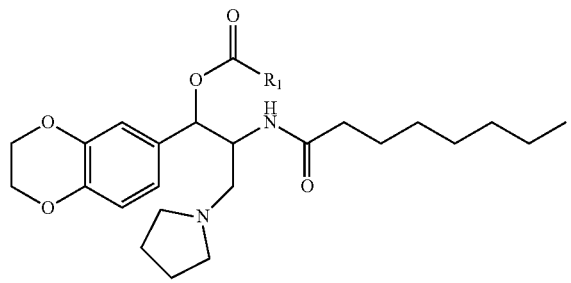

the geometric isomers, enantiomers, diastereomers, racemates, pharmaceutically acceptable salts or solvates thereof;

wherein, R¹ is selected from group consisting of optionally substituted aryl, optionally substituted heteroaryl, optionally substituted cycloalkyl, cycloheteroalkyl, amine, alkoxy, carboxylic acid, alkyl substituted with cycloheteroalkyl, alkyl substituted amine, alkyl substituted carboxylic acid, alkene substituted carboxylic acid.

3. The compound of formula A according to claim 1, which is represented by the following formula II:

(II)

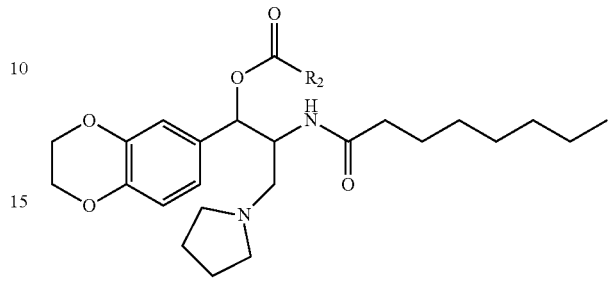

the geometric isomers, enantiomers, diastereomers, racemates, pharmaceutically acceptable salts or solvates thereof;

wherein R² is

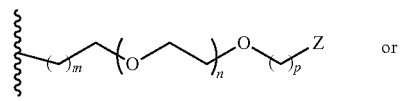 or

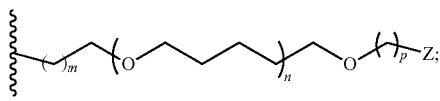

wherein m and p are independently selected from 0 to 3, n is selected from less than 10, about 50, about 100, about 150 or about 200 and Z is alkyl or amine.

4. The compound of formula A according to claim 1, which is represented by the following formula III:

(III)

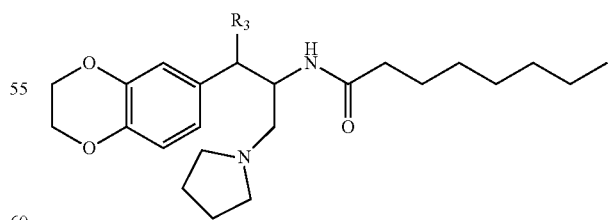

the geometric isomers, enantiomers, diastereomers, racemates, pharmaceutically acceptable salts or solvates thereof;

wherein R³ is selected from group consisting of boron species.

5. The compound of formula A according to claim 1, which is represented by the following formula IV:

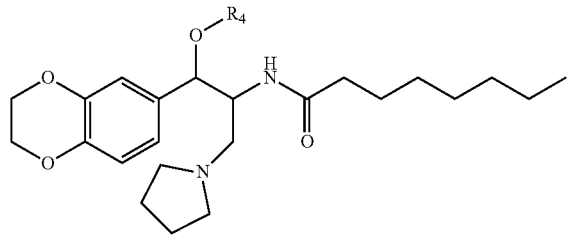

(IV)

the geometric isomers, enantiomers, diastereomers, racemates, pharmaceutically acceptable salts or solvates thereof;
wherein $R^4$ is selected from group consisting of alkyl substituted with cycloheteroalkyl, optionally substituted phosphoryl, alkyl substituted phosphoryl, sulfuryl, sulfonamide.

6. The compound of formula A according to claim 1, which is represented by the following formula IX:

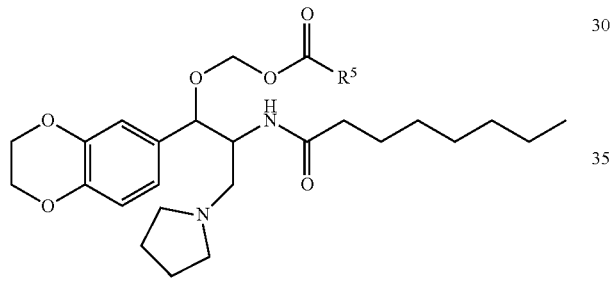

(IX)

the geometric isomers, enantiomers, diastereomers, racemates, pharmaceutically acceptable salts or solvates thereof;
wherein $R^5$ is selected from group consisting of optionally substituted aryl, optionally substituted heteroaryl, optionally substituted cycloalkyl, cycloheteroalkyl, alkyl, amine, alkoxy, carboxylic acid, alkyl substituted with cycloheteroalkyl, alkyl substituted amine.

7. The compound of formula A according to claim 1, represented by the following formula:

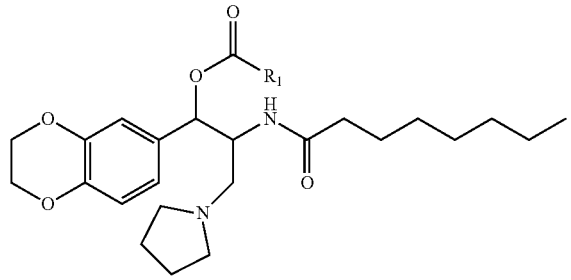

(I)

the geometric isomers, enantiomers, diastereomers, racemates, pharmaceutically acceptable salts or solvates thereof;
wherein $R^1$ is selected from group consisting of:

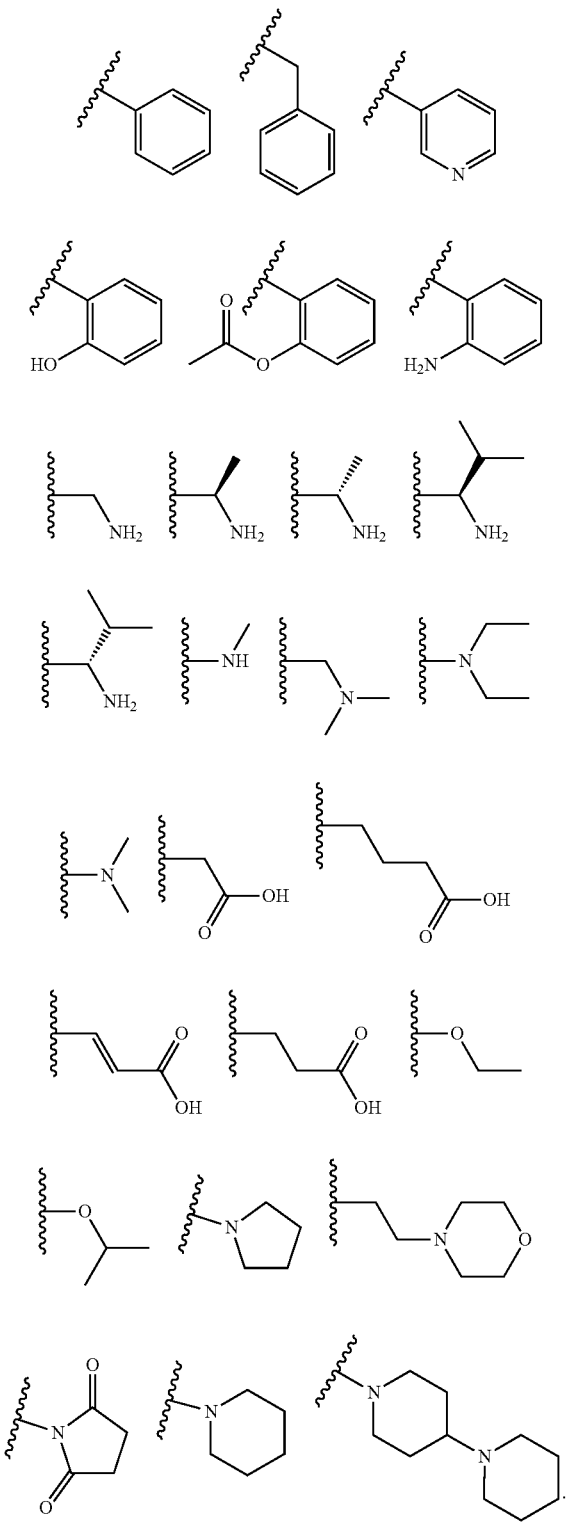

.

8. The compound of formula A according to claim 1, represented by the following formula II:

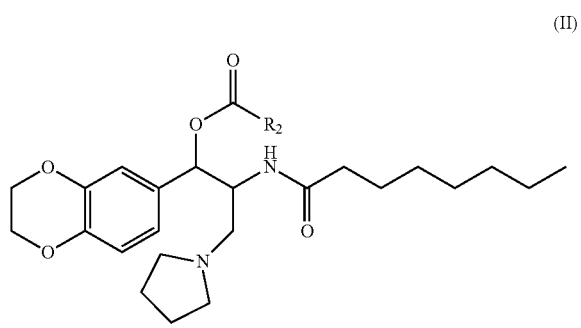
(II)

the geometric isomers, enantiomers, diastereomers, racemates, pharmaceutically acceptable salts or solvates thereof;

wherein $R^2$ is selected from group consisting of:

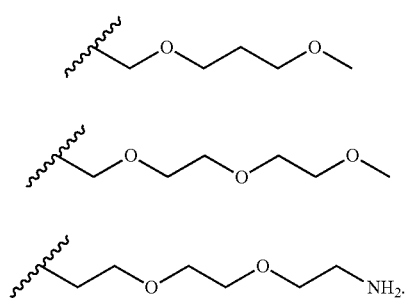

9. The compound of formula A according to claim 1, represented by the following formula III:

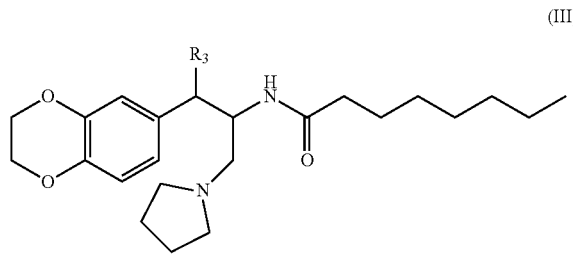
(III)

the geometric isomers, enantiomers, diastereomers, racemates, pharmaceutically acceptable salts or solvates thereof;

wherein, $R^3$ is selected from group consisting of:

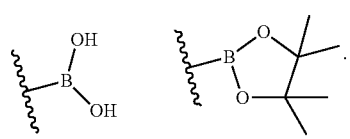

10. The compound of formula A according to claim 1, represented by the following formula IV:

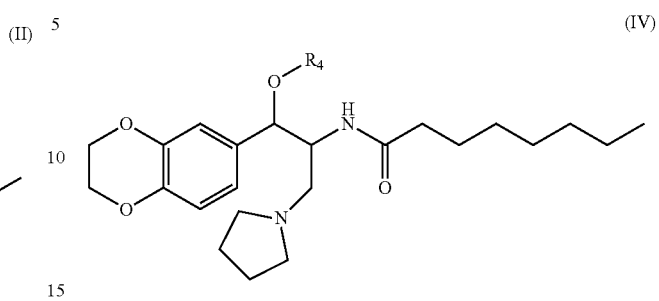
(IV)

the geometric isomers, enantiomers, diastereomers, racemates, pharmaceutically acceptable salts or solvates thereof;

wherein $R^4$ is selected from group consisting of:

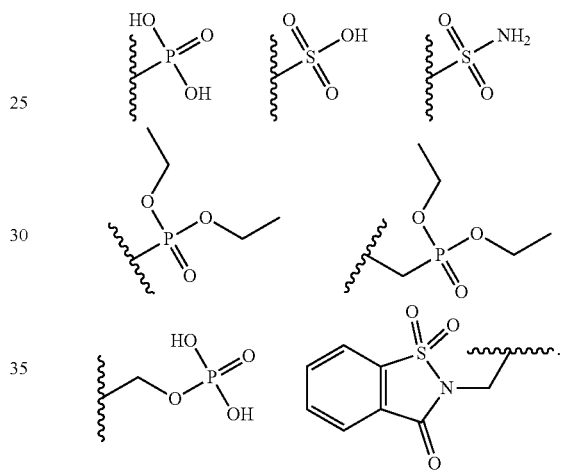

11. The compound of formula A according to claim 1, represented by the following formula IX:

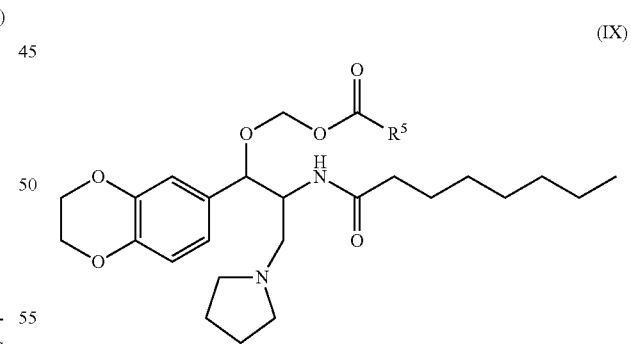
(IX)

the geometric isomers, enantiomers, diastereomers, racemates, pharmaceutically acceptable salts or solvates thereof;

wherein $R^5$ is selected from group consisting of:

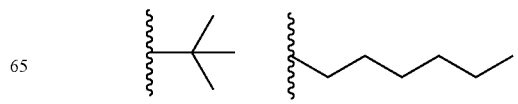

-continued
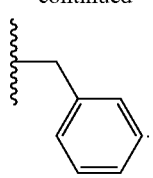
12. A compound selected from group consisting of
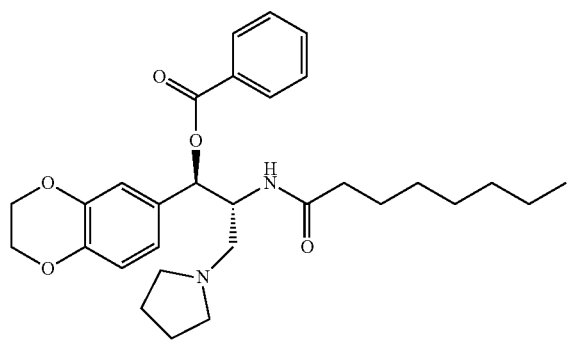
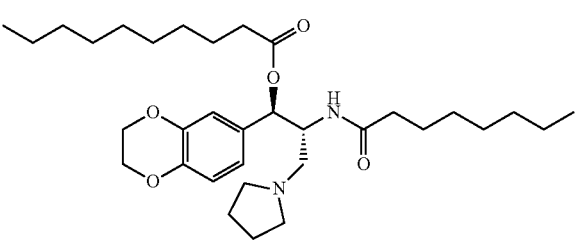
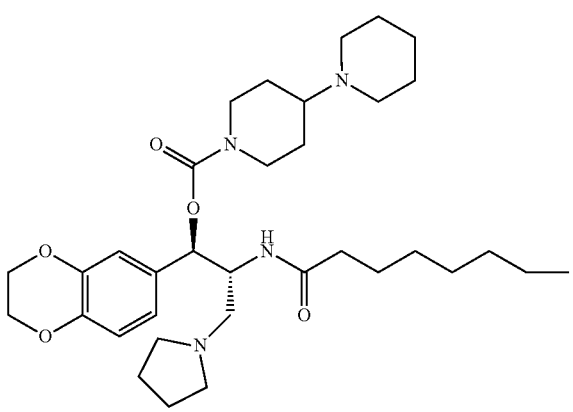
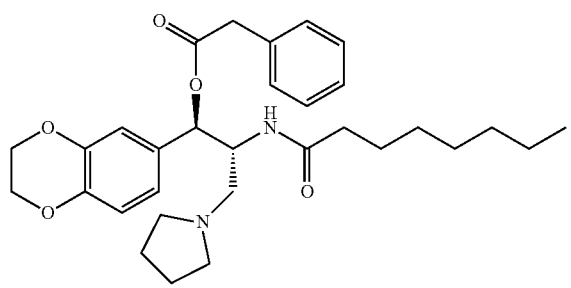
-continued
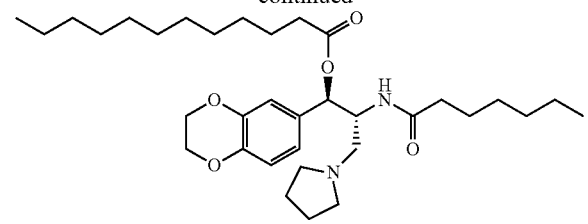
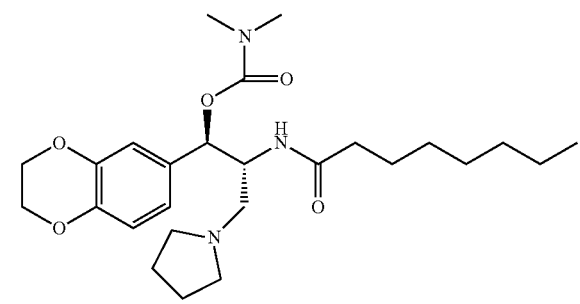
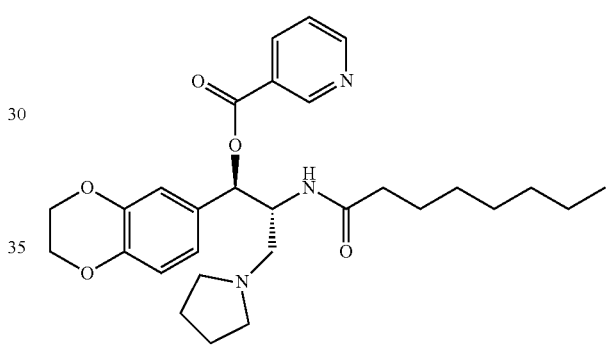
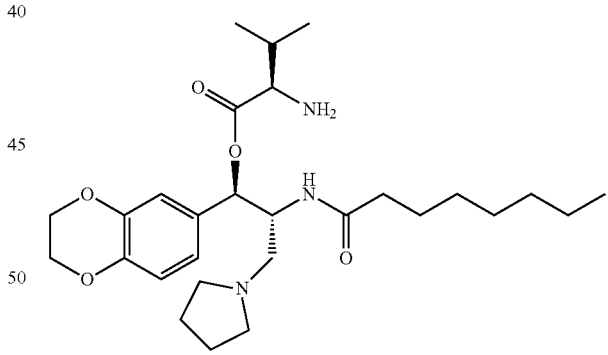
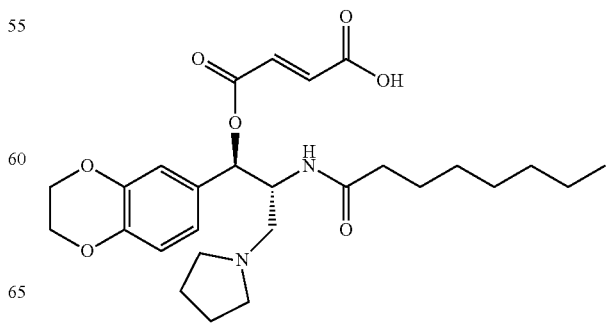

-continued
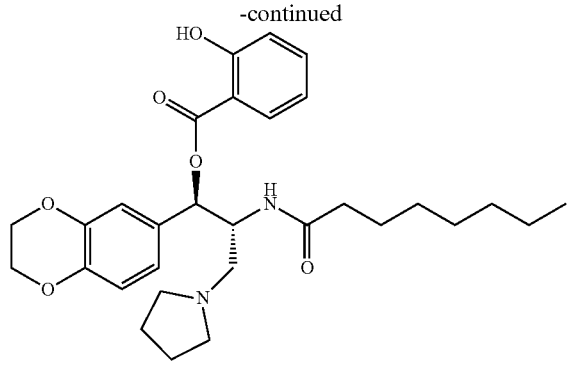
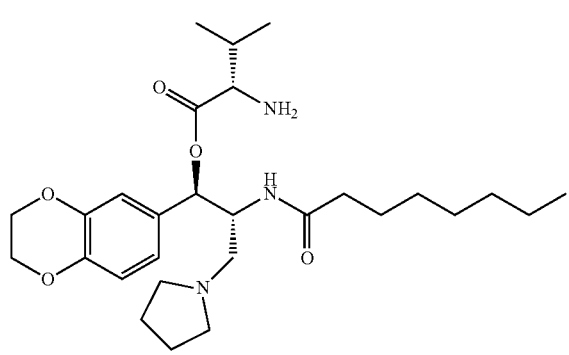
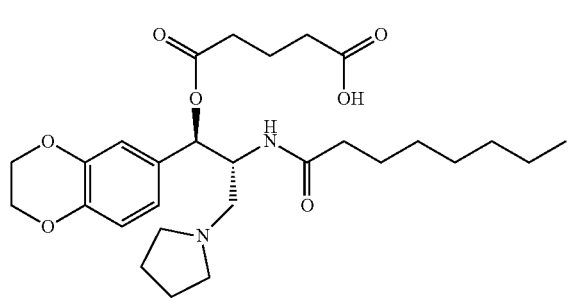
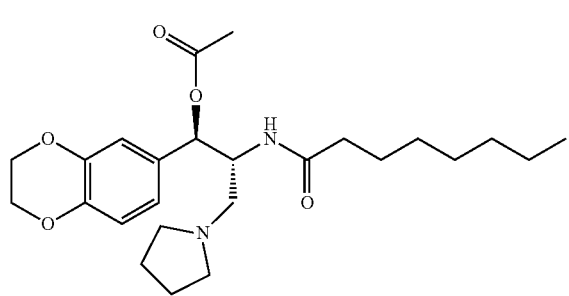
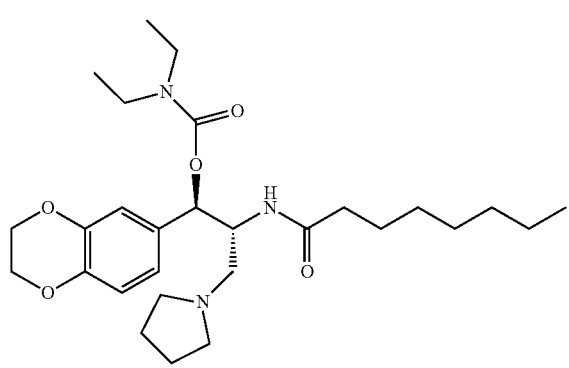
-continued
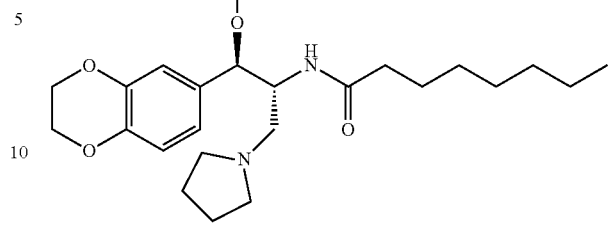
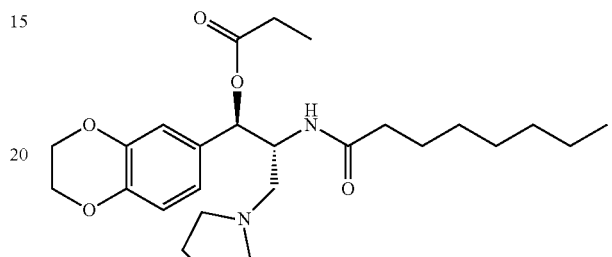
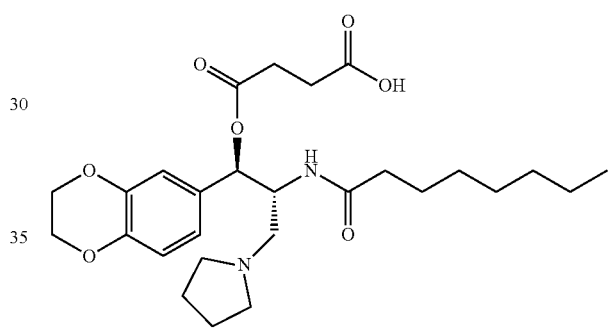
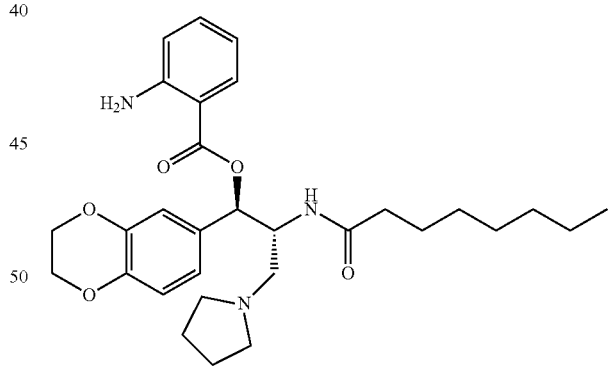
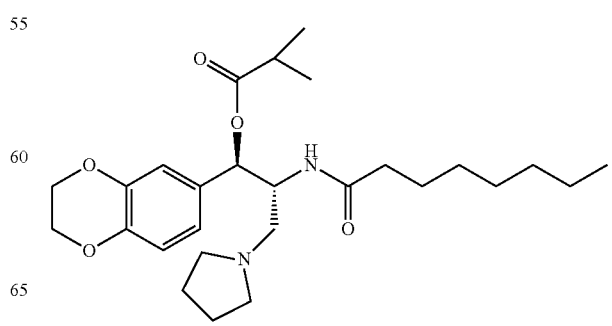

83
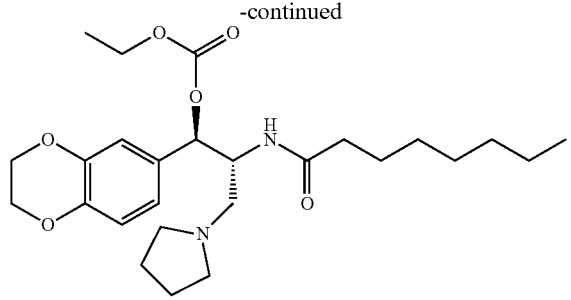
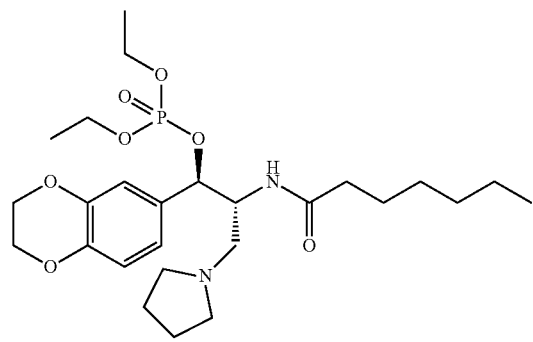
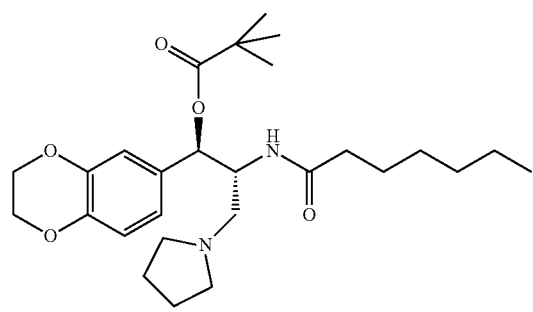
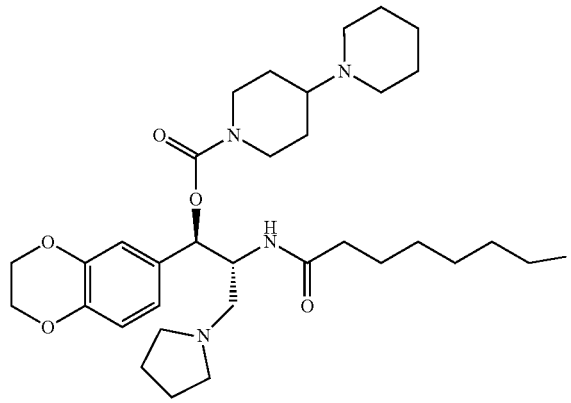
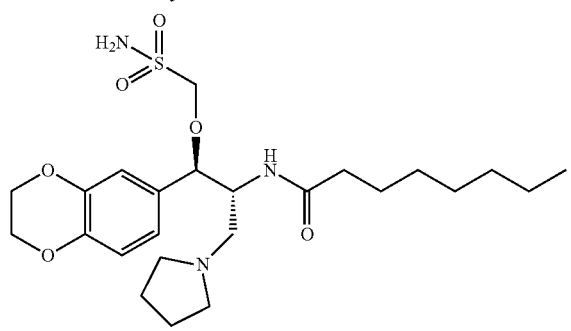
84
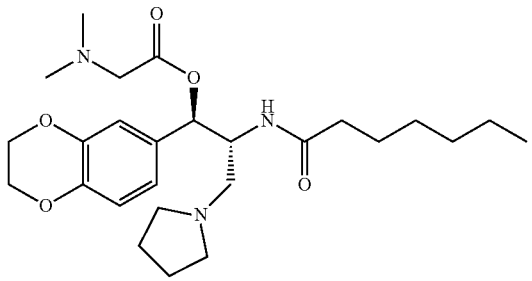
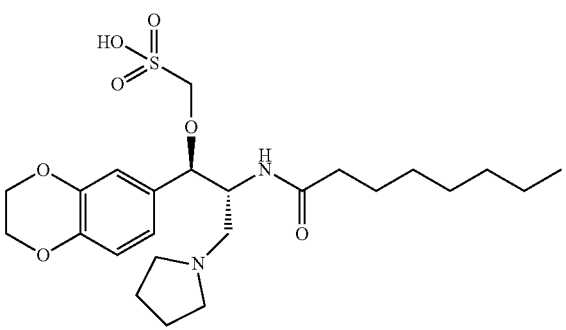
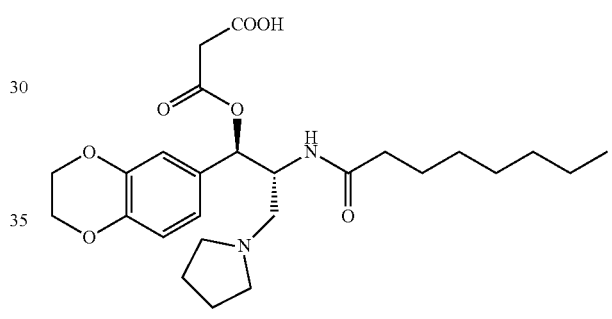
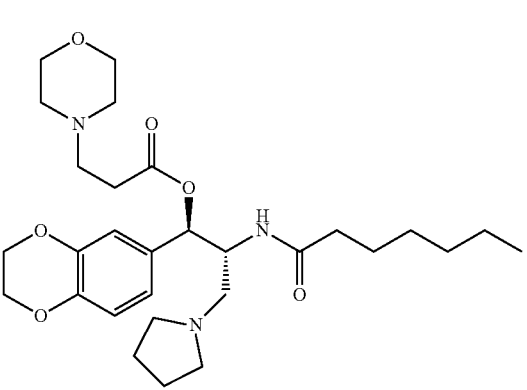
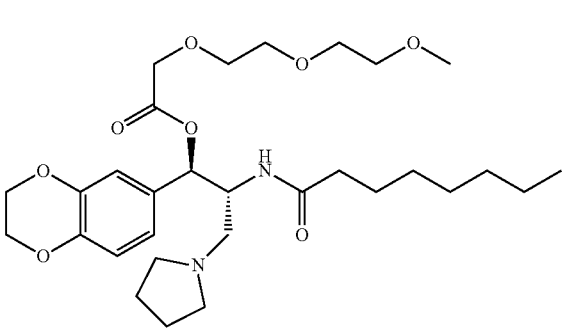

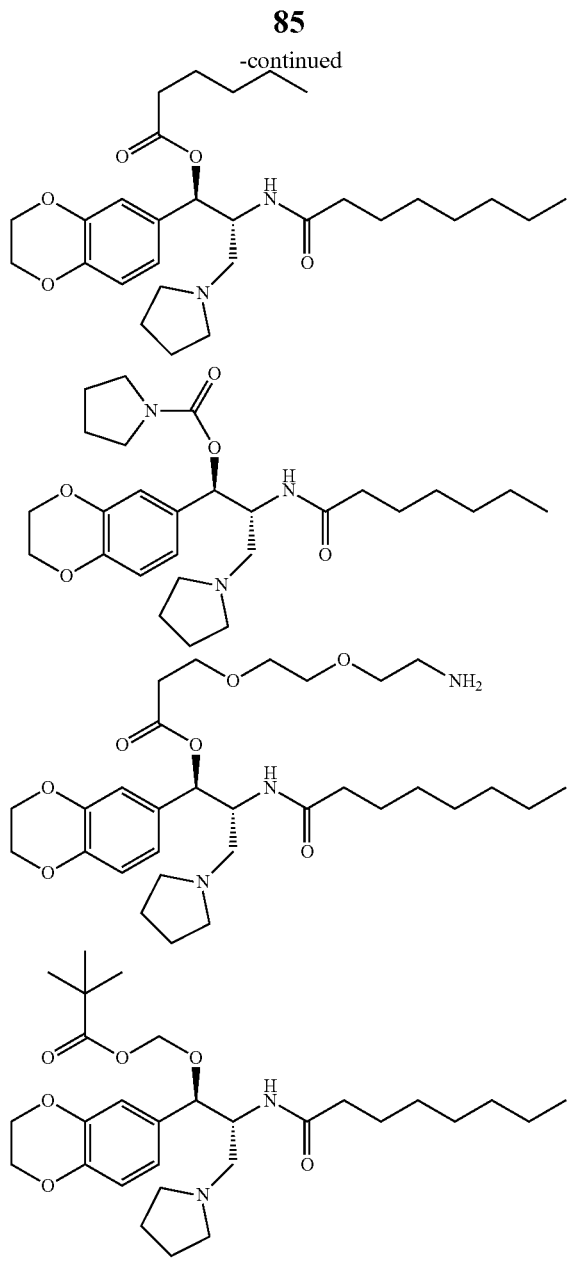

or pharmaceutically acceptable salt thereof.

13. A pharmaceutical composition comprising compound of formula A represented by following structural formula:

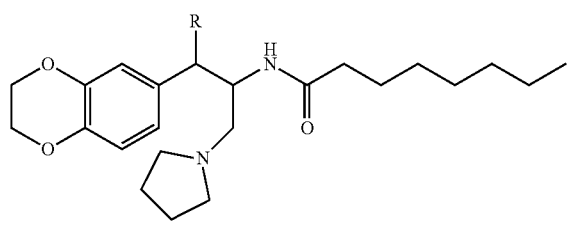

(A)

the geometric isomer, enantiomers, diastereomers, racemates, pharmaceutically acceptable salts or solvates thereof; and a pharmaceutically acceptable carrier or an excipient, wherein:

R is selected from group consisting of:

a)

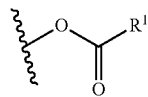

wherein, $R^1$ is selected from group consisting of optionally substituted aryl, optionally substituted heteroaryl, optionally substituted cycloalkyl, cycloheteroalkyl, amine, alkoxy, carboxylic acid, alkyl substituted with cycloheteroalkyl; alkyl substituted amine, alkyl substituted carboxylic acid, alkene substituted carboxylic acid;

b)

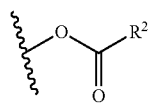

wherein, $R^2$ is

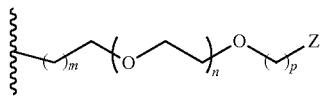

or

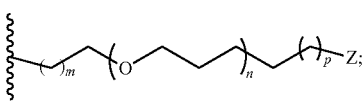

wherein m and p are independently selected from 0 to 3, n is selected from less than 10, about 50, about 100, about 150 or about 200 and Z is alkyl or amine;

c) $R^3$ wherein, $R^3$ is selected from group consisting of boron species;

d)

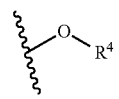

wherein, $R^4$ is selected from group consisting of alkyl substituted with cycloheteroalkyl, optionally substituted phosphoryl, alkyl substituted phosphoryl, sulfuryl, sulfonamide; and e)

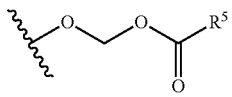

wherein, $R^5$ is selected from group consisting of optionally substituted aryl, optionally substituted heteroaryl, optionally substituted cycloalkyl, cycloheteroalkyl, alkyl, amine, alkoxy, carboxylic acid, alkyl substituted with cycloheteroalkyl; alkyl substituted amine.

* * * * *